US012728171B2

(12) United States Patent
Dreismann et al.

(10) Patent No.: US 12,728,171 B2
(45) Date of Patent: Sep. 8, 2026

(54) COMPLEMENT FACTOR I AND COMPLEMENT FACTOR I COFACTOR, VECTORS ENCODING THEREFOR AND THERAPEUTIC USE

(71) Applicant: NOVARTIS PHARMACEUTICALS UK LIMITED, London (GB)

(72) Inventors: Anna Dreismann, Stevenage (GB); Scott Ellis, Stevenage (GB); Josephine Heather Lucienne Joel, Stevenage (GB)

(73) Assignee: NOVARTIS PHARMACEUTICALS UK LIMITED, London (GB)

( * ) Notice: Subject to any disclaimer, the term of this patent is extended or adjusted under 35 U.S.C. 154(b) by 1322 days.

(21) Appl. No.: 17/415,860

(22) PCT Filed: Dec. 23, 2019

(86) PCT No.: PCT/GB2019/053698

§ 371 (c)(1),
(2) Date: Jun. 18, 2021

(87) PCT Pub. No.: WO2020/128535

PCT Pub. Date: Jun. 25, 2020

(65) Prior Publication Data

US 2022/0072157 A1 Mar. 10, 2022

(30) Foreign Application Priority Data

Dec. 21, 2018 (GB) ..................................... 1821082

(51) Int. Cl.

| | |
|---|---|
| ***A61K 48/00*** | (2006.01) |
| ***A61P 27/02*** | (2006.01) |
| ***C07K 14/47*** | (2006.01) |
| ***C12N 9/64*** | (2006.01) |
| ***C12N 15/86*** | (2006.01) |

(52) U.S. Cl.

CPC .......... *A61K 48/0058* (2013.01); *A61P 27/02* (2018.01); *C07K 14/472* (2013.01); *C12N 9/6424* (2013.01); *C12N 15/86* (2013.01); *C12Y 304/21045* (2013.01); *C12N 2750/14143* (2013.01)

(58) Field of Classification Search

CPC .............. A61K 48/0058; A61K 9/0048; A61K 48/0075; A61K 38/00; A61K 48/005; A61P 27/02; C07K 14/472; C12N 9/6424; C12N 15/86; C12N 2750/14143; C12N 9/48; C12Y 304/21045

See application file for complete search history.

(56) References Cited

U.S. PATENT DOCUMENTS

2019/0255193 A1* 8/2019 Groendahl ......... A61K 48/0075
2021/0145933 A1* 5/2021 Bishop .................... A61P 27/02
2021/0338838 A1* 11/2021 Hageman ........... A61K 48/0075

FOREIGN PATENT DOCUMENTS

| | | | |
|---|---|---|---|
| WO | WO 2014/194213 | A1 | 12/2014 |
| WO | WO 2015/055991 | A1 | 4/2015 |
| WO | WO 2017/053732 | A2 | 3/2017 |
| WO | WO 2017/072515 | A1 | 5/2017 |
| WO | WO 2017/194912 | A1 | 11/2017 |
| WO | WO 2018/170152 | A1 | 9/2018 |
| WO | 2018/224663 | A1 | 12/2018 |
| WO | WO 2019/138137 | A1 | 7/2019 |

OTHER PUBLICATIONS

Parret et al. "Critical reflections on synthetic gene design for recombinant protein expression." Current Opinion in Structural Biology 38 (2016): 155-162 (Year: 2016).*
Milker et al. "Kinetic modeling of an enzymatic redox cascade in vivo reveals cofactor-caused bottlenecks." ChemCatChem 9.17 (2017): 3420-7 (Year: 2017).*
Ausubel et al., 1999, Short Protocols in Molecular Biology, Ch. 18.
Ausubel et al., 1995, Short Protocols in Molecular Biology, Ch. 9, 13, 16.
Gait, M.J., 1984, "Oligonucleotide Synthesis: A Practical Approach" IRL Press.
Peden et al., 2011, "Ab-Externo AAV-Mediated Gene Delivery to the Suprachoroidal Space Using a 250 Micron Flexible Microcatheter," PLoS One 6(2):e17140.
Skerka et al., 2007, "Defective complement control of Factor H (Y402H) and FHL-1 in age-related macular degeneration," Molecular Therapy 14:316-327.
Krilisa et al., 2018, "Dual roles of different redox forms of complement factor H in protecting against age related macular degeneration" Free Radical Biology and Medicine 129:237-246.
Choi et al., "Optimization of AAV expression cassettes to improve packaging capacity and transgene expression in neurons," Molecular Brain, vol. 7, No. 17, Mar. 11, 2014, pp. 1-10.
Clark et al., "Identification of factor H-like protein 1 as the predominant complement regulator in Bruch's membrane: implications for age-related macular degeneration," J Immunol., vol. 193, No. 10, Nov. 15, 2014, pp. 4962-4970.
Hellwage et al., "The human complement regulatory factor-H-like protein 1, which represents a truncated form of factor H, displays cell-attachment activity," Biochemical Journal., vol. 326, Oct. 1997, pp. 321-327.
Naama et al., "Prevention of immune precipitation by purified components of the alternative pathway," Clin. exp. Immunol., vol. 60, 1985 (Accepted Oct. 31, 1984), pp. 169-177.
Ricklin et al., "The renaissance of complement therapeutics," Nature Reviews Nephrology, vol. 14, No. 1, 2017 (Published Jan. 2018), pp. 26-47.

(Continued)

*Primary Examiner* — Alexander W Nicol
(74) *Attorney, Agent, or Firm* — Biospark Intellectual Property Law

(57) ABSTRACT

A product comprising (i) a Complement Factor I (CFI) cofactor; and (ii) Complement Factor I (CFI), or nucleotide sequences encoding therefor, as a combined preparation for simultaneous, separate or sequential use in therapy.

13 Claims, 11 Drawing Sheets

Specification includes a Sequence Listing.

(56) References Cited

OTHER PUBLICATIONS

Office Action and Search Report issued May 5, 2023 in Russian application No. 2021119359, including unofficial English translation of Office Action.
Dlin et al., 2016, "Nephropathies associated with complement system pathology," Ros Vestn Perinatol I Pediatr 61(6):21-31.
Allocca et al., 2007, "Novel Adno-Associated Virus Serotypes Efficiently Tranduce Murine Photoreceptors," J. Virol., 81:11372-80.
Altschul et al., 1990, "Basic local alignment search tool," J Mol Biol, 215(3):403-410.
Ausubel et al., 1995, "Current Protocols in Molecular Biology", John Wiley & Sons, pp. iii-xxii.
Bainbridge et al., 2008, "Effect of Gene Therapy on Visual Function in Leber's Congenital Amaurosis," N. Engl. J. Med., 358:2231-2239.
Bressler et al., 1999, "Photodynamic Therapy of Subfoveal Choroidal Neovascularization in Age-related Macular Degeneration with Verteporfin," Arch Ophthalmol 117: 1329-1345.
Cai et al., 2014, "Targeted genome editing by lentiviral protein transduction of zinc-finger and TAL-effector nucleases," ELIFE, 3:01911.
Cashman et al., 2015, "Adenovirus-mediated delivery of Factor H attenuates complement C3 induced pathology in the murine retina: a potential gene therapy for age-related macular degeneration," J. Gene Medicine, 17:229-243.
Choi et al., 2005, "AAV Hybrid Serotypes: Improved Vectors for Gene Delivery" Current Gene Therapy, 5(3):299-310.
Clark et al., 2015, "Role of Factor H and Related Proteins I Regulating Complement Activation in the Macula, and Relevance to Age-Related Macular Degeration," J Clin Med, 4:18-31.
Degn et al., 2011, "Disease-causing mutations in genes of the complement system," Am J Hum Genet, 88:689-705.
Devereux et al., 1984, "A comprehensive set of sequence analysis programs for the VAX," Nucleic Acids Res 12(1):387-395.
Dong et al., 1996, "Quantitative Analysis of the Packaging Capacity of Recombinant Adeno-Associated Virus," Human Gene Therapy, 7(17):2101-2112.
Dos Santos Coura R and Nardi N B, 2007, "The state of the art of adeno-associated virus-based vectors in gene therapy," Virology Journal, 4:99.
Esumi et al., 2004, "Analysis of the VMD2 Promoter and Implication of E-box Binding Factors in Its Regulation," J. Biol. Chem., 279:19064-19073.
Gaj et al., 2012, "Targeted gene knockout by direct delivery of zinc-finger nuclease proteins," Nature Methods, 9(8):805-807.
Goldberger et al., 1987, "Human Complement Factor I: Analysis of cDNA-derived Primary Structure and Assignment of its Gene to Chromosome 4," J Biol. Chem., 262(21):10065-10071.
Harrison R A, 1996, Purification, Assay, and Characterization of Comlement Proteins from Plasma, in : "Herzenberg L A & Weir D M (eds)" "Weir's Handbook of Experimental Immunology", 5(75):36-37.
Hsiung et al., 1982, "Purification of human C3b inactivator by monoclonal-antibody affinity chromatography," Biochem J., 203:293-298.
Kavanagh et al., 2015, "Rare genetic variants in the CFI gene are associated with advanced age-related macular degeneration and commonly result in reduced serum factor I levels," Human Mol Genet, 24:3861-3870.
Lachmann P J & Hobart M J, 1978, "Handbook of Experimental Imunology", chapter 5A "Complement Technology", 17 pages.
Lachmann P J, 2009, "The amplification loop of the complement pathways," Adv. Immunol., 104:115-149.
Laughlin et al., 1979, "Spliced adenovirus-associated virus RNA," Proc. Natl. Acad. Sci. USA, 5567-5571.
Lilley et al., 1992, "Methods in Enzymology, vol. 211 DNA Structures", Part A "Synthesis and Physical Analysis of DNA", Academic Press.
Liu D and Niu Z-X, 2009, "The structure, genetic polymorphisms, expression and biological functions of complement receptor type 1 (CR1/CD35)," Immunopharmacology and Immunotoxicology, 31:524-535.
Maerzig et al., 2012, "Retroviral Protein Transfer: Falling Apart to Make an Impact," Current Gene Therapy, 12:389-409.
Mancuso et al., 2009, "Gene therapy for red-green colour blindness in adult primates," Nature, 461(7265):784-787.
Morgan and Harris, 2015, "Complement, a target for therapy in inflammatory and degenerative diseases," Nature Reviews Drug Discovery, 14: 857-877.
Naso et al., 2017, "Adeno-Associated Virus (AAV) as a Vector for Gene Therapy" BioDrugs, 31:317-334.
Nilsson et al., 2011, "Complement factor I in health and disease" Molecular Immunology, 48:1611-1620.
Polak, 1990, "Situ Hybridization: Principles and Practice", Oxford University Press.
Roe and Khan, 1996, "DNA Isolation and Sequencing: Essential Techniques", John Wiley & Sons.
Roversi et al., 2011, "Structural basis for complement factor I control and its disease-associated sequence polymorphisms," Proc Nat Acad Sci, 108:12839-12844.
Sambrook and Maniatis, 1989, "Molecular Cloning: A Laboratory Manual", Cold Spring Harbor Laboratory Press.
Schmidt et al., 2008, "A New Map of Glycosaminoglycan and C3b Binding Sites on Factor H," Journal of Immunology, 181:2610-2619.
Seddon, J.M., 2001, "Epidemiology of age-related macular degeneration." In: Ogden, T.E., et al., eds. Ryan S.J., ed-in-chief. Retina vol. II. 3rd ed. St. Louis, Mo.: Mosby:1039-1050.
Tatusova et al., 1999, "Blast 2 Sequences, a new tool for comparing protein and nucleotide sequences," FEMS Microbiology Letters, 174(2):247-250.
"UniProtKB", Database accession No. P08603, Jan. 16, 2019.
Wu et al., 2006, "Adeno-associated virus serotypes: vector toolkit for human gene therapy," Molecular Therapy, 14: 316-27.
Hallam et al., 2024, "Ocular biomarker profiling after complement factor I gene therapy in geographic atrophy secondary to age-related macular degenerations," eLife, doi.org/10.7554/eLife.99806.1, pp. 1-66.
*Homo sapiens* complement factor I (CFI), transcript variant 2, mRNA, Genbank NCBI Reference Sequence: NM_000204.4, 2020.

* cited by examiner

A
FHL1 titration
A450
neg control
FI:FHL1 3:1
FI:FHL1 2:1
FI:FHL1 1:1
FI:FHL1 1:2
FI:FHL1 1:3
FI:FHL1 1:4
FH titration
ug/ml iC3b
neg ctrl
FI:FH 3:1
FI:FH 2:1
FI:FH 1:1
FI:FH 1:2
FI:FH 1:3
FI:FH 1:4
B
FI supplementation
+27.8μg/ml FI
(0.32μM FI)
A450nm (C3d deposition)
Ratio FI:cofactor
FH supplementation
+53.5μg/ml FH
(0.35μM FH)
A450nm (C3d deposition)
Ratio FI:cofactor
FHL1 supplementation
+7.8μg/ml FHL1
(0.16μM FHL1)
A450nm (C3d deposition)
Ratio FI:cofactor Plasma: Exsera 'normal range' (n=80)
Vitreous: GTX 'SL' normal samples (n=11)
+ Exsera 'non-diabetic normal'(n=18)

B

A

COMPLEMENT FACTOR I AND COMPLEMENT FACTOR I COFACTOR, VECTORS ENCODING THEREFOR AND THERAPEUTIC USE

FIELD OF THE INVENTION

The present invention relates to agents for use in gene therapy. In particular, the invention relates to combinations of Complement Factor I (CFI) and CFI cofactors, such as Complement Factor H-like Protein 1 (FHL1), polynucleotides encoding therefor, and their uses in the treatment or prevention of complement-mediated and complement-associated disorders, including complement-mediated eye diseases, such as age-related macular degeneration (AMD).

BACKGROUND TO THE INVENTION

The macula is a small area in the retina of the eye, approximately 3 to 5 millimetres in size, adjacent to the optic nerve. It is the most sensitive area of the retina and contains the fovea, a depressed region that allows for high visual acuity and contains a dense concentration of cones, the photoreceptors that are responsible for colour vision.

Age-related macular degeneration (AMD) is the most common cause of functional blindness in developed countries for persons over 50 years of age (Seddon, J. M., Epidemiology of age-related macular degeneration. In: Ogden, T. E., et al., eds. Ryan S. J., ed-in-chief. Retina Vol II. 3rd ed. St. Louis, Mo.: Mosby; 2001:1039-1050). AMD is associated with neovascularisation originating from the choroidal vasculature and extending into the subretinal space. In addition, AMD is characterised by progressive degeneration of the retina, retinal pigment epithelium (RPE), and underlying choroid (the highly vascular tissue that lies beneath the RPE, between the retina and the sclera).

A variety of factors including oxidative stress, inflammation with a possible autoimmune component, genetic background (e.g. mutations), and environmental or behavioural factors such as smoking and diet may contribute to the pathogenesis of AMD.

The clinical progression of AMD is characterised in stages according to changes in the macula. The hallmark of early AMD is the appearance of drusen, which are accumulations of extracellular debris underneath the retina and appear as yellow spots in the retina during clinical examination and on fundus photographs. Drusen are categorised by size as small (<63 μm), medium (63-124 μm) and large (>124 μm). They are also considered as hard or soft depending on the appearance of their margins on ophthalmological examination. While hard drusen have clearly defined margins, soft drusen have less defined, fluid margins. The Age-related Eye Disease Study (AREDS) fundus photographic severity scale is one of the main classification systems used for this condition.

Intermediate AMD is diagnosed by large drusen and/or any retinal pigment abnormalities. Intermediate AMD may cause some vision loss, but, like early AMD, it is usually asymptomatic.

Late-stage AMD has been classified into "dry" and "wet" (exudative or neovascular) forms. Dry AMD is more common than wet AMD, but the dry form can progress to the wet form, and the two occur simultaneously in a significant number of cases. Dry AMD is typically characterised by progressive apoptosis of cells in the RPE layer and overlying photoreceptor cells, and frequently also the underlying cells in the choroidal capillary layer. Confluent areas of RPE cell death accompanied by overlying photoreceptor atrophy are referred to as geographic atrophy (GA). Patients with this form of AMD (advanced dry form) experience a slow and progressive deterioration in central vision.

Wet AMD is characterised by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularisation (CNV) and its secondary complications. A subtype of neovascular AMD is termed retinal angiomatous proliferation (RAP). Here, angiomatous proliferation originates from the retina and extends posteriorly into the subretinal space, eventually communicating in some cases with choroidal new vessels.

The complement system (CS) has been implicated in early AMD pathogenesis based on the identification of CS components in drusen from eyes of AMD patients. In AMD, at least 129 types of drusen-deposited proteins have been identified, including different apolipoprotein types (E, B or A-I), several amyloid peptides (P, Aβ or SA-1), TIMP-3, serum albumin, and certain proteins associated with cellular function (e.g. ATP synthase β subunit, scavenger receptor B2 and retinol dehydrogenase). AMD-derived drusen also contain almost all of the complement proteins, including regulatory proteins (CFH, complement receptor 1 (CR1), vitronectin and clusterin), the products of CS activation and degradation (C1q, C3, C3a, C3b and C5a), and members of the terminal CS pathway comprising the MAC components (i.e. 5, 6, 8 (α, β and γ) and 9) in the separated and complex form. Accumulating drusen may activate the CS, trigger the local production of inflammatory mediators, and attract leukocytes that in turn augment the local inflammatory state present in AMD.

Current treatment options for AMD include photodynamic therapy with benzoporphyrin (Arch Ophthalmol (1999) 117: 1329-1345) and a number of therapies which target the Vascular Endothelial Growth Factor (VEGF) pathway. Examples of such VEGF-targeted therapies include antibodies such as ranibizumab (marketed as Lucentis™, Genentech, Inc.) and bevacizumab (Avastin™, Genentech, Inc.) and aflibercept (Eylea™, Bayer). However, although these anti-VEGF antibody therapies have been very effective, they are only approved for treatment of the wet or neovascular form of AMD, which accounts for approximately 10-15% of all AMD patients. Antibody therapies are administered by monthly intravitreal injection, in an operating theatre or clean-room, which places a burden on patients, who are typically elderly.

There are currently no approved treatments for the early stage or advanced (dry) forms of AMD.

The complement system is a well-documented target for the treatment of many inflammatory diseases. Overactive or improperly-functioning complement system has been implicated in the pathology of many chronic inflammatory conditions, including AMD (Nature Reviews (2015) 14: 857-877). As a consequence, several complement-targeted therapeutics have been proposed, or are currently in development, which target the alternative pathway amplification loop/C3b feedback cycle as a means of decreasing C3b feedback or increasing C3b breakdown (FIG. 1).

Lampalizumab (Genentech/Roche) is a humanised monoclonal antibody that inhibits Complement Factor D, administered by monthly intravitreal injection to stop the rate of progression of geographic atrophy. Lampalizumab showed some reduction in the rate of geographic atrophy enlargement in a Phase 2 clinical trial. However, in Phase III randomised clinical trials involving 906 participants, lampalizumab failed to reduce GA enlargement when compared with sham over 48 weeks. Results showed substantial and consistent enlargement of GA, at a mean of approximately 2 $mm^2$ per year.

However, there remains a need for alternative therapies for the treatment of complement mediated or complement associated diseases, in particular ocular diseases, such as AMD, in particular treatments that are effective in broad AMD populations and not limited to particular genotypes that may predispose an individual to AMD and other complement-related disorders.

SUMMARY OF THE INVENTION

The applicant has identified therapeutic combinations of Complement Factor I (CFI) and CFI cofactors (proteins that have cofactor activity in the CFI-mediated cleavage of C3b, such as Complement Factor H Like Protein 1 (FHL1), Complement Factor H (CFH), Complement Receptor type 1 (CR1) and Membrane Cofactor Protein (MCP)) for delivery to a patient for restoration or rebalancing of overactive complement C3b feedback cycle. The combinations provide CFI and CFI cofactor at molar ratios that ensure the cofactor is provided in stoichiometric excess to CFI to ensure maximum activity of CFI in C3b breakdown (and downregulation of overactive complement system). This is important for patients who may have genetic deficiencies in certain complement system proteins and/or for treatments that are administered to tissue or organs in which co-factor levels may be reduced in comparison to systemic levels, for example, in the eye or kidney.

In addition, the applicant has provided bicistronic vectors that can be used for the delivery and co-expression of both CFI and CFI cofactor (e.g. FHL1) to a patient. In particular, the applicant has successfully designed functional AAV vectors that can be produced at good titres and comprise nucleotide sequences encoding both CFI and cofactor, thus overcoming challenges posed by the limited capacity of AAV. The bicistronic vectors of the invention also advantageously enable good expression of both CFI and cofactor; and co-expression of CFI and cofactor at ratios that have been identified herein as beneficial.

In one aspect, the invention provides a product comprising (i) a Complement Factor I (CFI) cofactor; and (ii) Complement Factor I (CFI), or nucleotide sequences encoding therefor, as a combined preparation for simultaneous, separate or sequential use in therapy.

In another aspect, the invention provides a product comprising (i) Complement Factor H Like Protein 1 (FHL1) or Complement Factor H (CFH); and (ii) Complement Factor I (CFI), or nucleotide sequences encoding therefor, as a combined preparation for simultaneous, separate or sequential use in therapy.

In particular embodiments, the product is used in the treatment of complement-mediated disorders, particularly chronic inflammatory conditions and even more particularly, those which are associated with overactivity of the complement C3b feedback cycle.

In another aspect, the invention provides a product comprising (i) a Complement Factor I (CFI) cofactor; and (ii) Complement Factor I (CFI), or nucleotide sequences encoding therefor, as a combined preparation for simultaneous, separate or sequential use in treating or preventing a complement-mediated disorder, preferably a complement-mediated disorder of the eye.

In another aspect, the invention provides a product comprising (i) Complement Factor H Like Protein 1 (FHL1) or Complement Factor H (CFH); and (ii) Complement Factor I (CFI), or nucleotide sequences encoding therefor, as a combined preparation for simultaneous, separate or sequential use in treating or preventing a complement-mediated disorder of the eye.

In some embodiments, the Complement Factor I (CFI) cofactor is selected from the group consisting of Complement Factor H Like Protein 1 (FHL1); Complement Factor H (CFH); Complement Receptor 1 (CR1) or a fragment thereof; and Membrane Cofactor Protein (MCP) or a fragment thereof.

In some embodiments, the Complement Factor I (CFI) cofactor is Complement Factor H (CFH). In some embodiments, the Complement Factor I (CFI) cofactor is Complement Receptor 1 (CR1) or a fragment thereof. In some embodiments, the Complement Factor I (CFI) cofactor is Membrane Cofactor Protein (MCP) or a fragment thereof.

In preferred embodiments, the Complement Factor I (CFI) cofactor is Complement Factor H Like Protein 1 (FHL1).

In preferred embodiments, the product comprises (i) Complement Factor H Like Protein 1 (FHL1); and (ii) Complement Factor I (CFI), or nucleotide sequences encoding therefor. In other embodiments, the product comprises (i) Complement Factor H (CFH); and (ii) Complement Factor I (CFI), or nucleotide sequences encoding therefor. In other embodiments, the product comprises (i) Complement Receptor 1 (CR1) or a fragment thereof; and (ii) Complement Factor I (CFI), or nucleotide sequences encoding therefor. In other embodiments, the product comprises (i) Membrane Cofactor Protein (MCP) or a fragment thereof; and (ii) Complement Factor I (CFI), or nucleotide sequences encoding therefor.

In some embodiments, the disorder is associated with over-activity of the complement C3b feedback cycle and/or under-activity of the C3b breakdown cycle (see FIG. 1).

In some embodiments, the disorder is a chronic complement-mediated inflammatory condition of the eye.

In some embodiments, the disorder is age-related macular degeneration (AMD) or diabetic retinopathy. In other embodiments, the disorder is glaucoma, Stargardt's disease, central serous chorioretinopathy or retinitis pigmentosa.

In preferred embodiments, the disorder is AMD. In some embodiments, the AMD is dry AMD.

In some embodiments, the product provides (i) and (ii) to a subject in a (i): (ii) molar ratio of at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 40:1, at least 50:1 or at least 60:1.

In some embodiments, the product provides (i) and (ii) to a subject in a (i): (ii) molar ratio of at least 2:1. In some embodiments, the product provides (i) and (ii) to a subject in a (i): (ii) molar ratio of at least 3:1. In preferred embodiments, the product provides (i) and (ii) to a subject in a (i): (ii) molar ratio of at least 8:1.

In some embodiments, the product provides (i) and (ii) to a subject in a (i): (ii) molar ratio of between 2:1 and 34:1, between 2:1 and 25:1, between 2:1 and 15:1, between 2:1 and 12:1, between 3:1 and 10:1.

In preferred embodiments, the product provides (i) and (ii) to a subject in a (i): (ii) molar ratio of between 3:1 and 10:1.

The provided molar ratios may be achieved through, for example, delivery of protein, polynucleotide or vector to a subject. Protein levels may be readily measured by the skilled person using techniques known in the art, such as ELISA, for example as described herein. Likewise, amounts of proteins expressed from polynucleotides or vectors encoding therefor may be measured using similar approaches.

In another aspect, the invention provides an isolated polynucleotide comprising nucleotide sequences encoding (i) a Complement Factor I (CFI) cofactor; and (ii) Complement Factor I (CFI).

In another aspect, the invention provides an isolated polynucleotide comprising nucleotide sequences encoding (i) Complement Factor H Like Protein 1 (FHL1) or Complement Factor H (CFH); and (ii) Complement Factor I (CFI).

In some embodiments, the Complement Factor I (CFI) cofactor is selected from the group consisting of Complement Factor H Like Protein 1 (FHL1); Complement Factor H (CFH); Complement Receptor 1 (CR1) or a fragment thereof; and Membrane Cofactor Protein (MCP) or a fragment thereof.

In some embodiments, the Complement Factor I (CFI) cofactor is Complement Factor H (CFH). In some embodiments, the Complement Factor I (CFI) cofactor is Complement Receptor 1 (CR1) or a fragment thereof. In some embodiments, the Complement Factor I (CFI) cofactor is Membrane Cofactor Protein (MCP) or a fragment thereof.

In preferred embodiments, the Complement Factor I (CFI) cofactor is Complement Factor H Like Protein 1 (FHL1).

In preferred embodiments, the polynucleotide comprises nucleotide sequences encoding (i) Complement Factor H Like Protein 1 (FHL1); and (ii) Complement Factor I (CFI). In other embodiments, the polynucleotide comprises nucleotide sequences encoding (i) Complement Factor H (CFH); and (ii) Complement Factor I (CFI). In other embodiments, the polynucleotide comprises nucleotide sequences encoding (i) Complement Receptor 1 (CR1) or a fragment thereof; and (ii) Complement Factor I (CFI). In other embodiments, the polynucleotide comprises nucleotide sequences encoding (i) Membrane Cofactor Protein (MCP) or a fragment thereof; and (ii) Complement Factor I (CFI).

In some embodiments, the polynucleotide further comprises a nucleotide sequence encoding a CMV promoter. Preferably, the CMV promoter is upstream of the nucleotide sequences encoding the (i) and (ii).

In some embodiments, the polynucleotide further comprises a nucleotide sequence encoding a WPRE regulatory element. Preferably, the WPRE regulatory element is downstream of the nucleotide sequences encoding the (i) and (ii).

In some embodiments, the polynucleotide further comprises a nucleotide sequence encoding a poly-A signal. Preferably, wherein the poly-A signal is downstream of the nucleotide sequences encoding the (i) and (ii).

In some embodiments, the polynucleotide further comprises a nucleotide sequence encoding a Bovine Growth Hormone poly-A signal. Preferably, wherein the Bovine Growth Hormone poly-A signal is downstream of the nucleotide sequences encoding the (i) and (ii).

In some embodiments, the polynucleotide further comprises nucleotide sequences encoding:

(a) a CMV promoter, wherein the CMV promoter is upstream of the nucleotide sequences encoding the (i) and (ii); and (b) a Bovine Growth Hormone poly-A signal, wherein the Bovine Growth Hormone poly-A signal is downstream of the nucleotide sequences encoding the (i) and (ii).

In other embodiments, the polynucleotide further comprises nucleotide sequences encoding:

(a) a CMV promoter, wherein the CMV promoter is upstream of the nucleotide sequences encoding the (i) and (ii);

(b) a WPRE regulatory element, wherein the WPRE regulatory element is downstream of the nucleotide sequences encoding the (i) and (ii); and (c) a Bovine Growth Hormone poly-A signal, wherein the Bovine Growth Hormone poly-A signal is downstream of the nucleotide sequences encoding the (i) and (ii).

In preferred embodiments, the WPRE regulatory element is a WPRE3 regulatory element.

In preferred embodiments, the nucleotide sequence encoding (i) is upstream of the nucleotide sequence encoding (ii).

In other embodiments, the nucleotide sequence encoding (ii) is upstream of the nucleotide sequence encoding (i).

In some embodiments, the nucleotide sequences encoding the (i) and (ii) are operably linked by a linker. In some embodiments, the linker is a Furin, GSG, 11aa1D or F2A linker. In preferred embodiments, the linker contains a self-cleaving 2A peptide sequence, for example P2A or a sequence which comprises or is defined by a Furin cleavage site, GSG, 11a1D and an F2A sequence.

In some embodiments, the polynucleotide further comprises one or more adeno-associated virus (AAV) inverted terminal repeats (ITRs). In preferred embodiments, the polynucleotide further comprises two AAV ITRs.

In some embodiments, the polynucleotide comprises an AAV ITR at its 5' end and an AAV ITR at its 3' end.

In some embodiments, the polynucleotide comprises:

(a) a 5' AAV ITR;

(b) a CMV promoter;

(c) a nucleotide sequence encoding a Complement Factor I (CFI) cofactor, preferably FHL1;

(d) a linker, optionally wherein the linker comprises a Furin cleavage site, GSG, 11a1D and an F2A sequence;

(e) a nucleotide sequence encoding CFI;

(f) a poly-A signal, preferably a Bovine Growth Hormone poly-A signal; and (g) a 3' AAV ITR.

In some embodiments, the polynucleotide comprises:

(a) a 5' AAV ITR;

(b) a CMV promoter;

(c) a nucleotide sequence encoding a Complement Factor I (CFI) cofactor, preferably FHL1;

(d) a linker, optionally wherein the linker comprises a Furin cleavage site, GSG, 11a1D and an F2A sequence;

(e) a nucleotide sequence encoding CFI;

(f) a WPRE regulatory element, preferably wherein the WPRE regulatory element is a WPRE3 regulatory element;

(g) a poly-A signal, preferably a Bovine Growth Hormone poly-A signal; and (h) a 3' AAV ITR.

In preferred embodiments, the polynucleotide comprises:

(a) a 5' AAV ITR;

(b) a CMV promoter;

(c) a nucleotide sequence encoding FHL1;

(d) a linker comprising a Furin cleavage site, GSG, 11a1D and an F2A sequence;

(e) a nucleotide sequence encoding CFI;

(f) a WPRE3 regulatory element;

(g) a poly-A signal, preferably a Bovine Growth Hormone poly-A signal; and (h) a 3' AAV ITR.

In some embodiments, the Complement Factor I (CFI) cofactor is selected from the group consisting of Complement Factor H Like Protein 1 (FHL1); Complement Factor H (CFH); Complement Receptor 1 (CR1) or a fragment thereof; and Membrane Cofactor Protein (MCP) or a fragment thereof.

In some embodiments, the Complement Factor I (CFI) cofactor is Complement Factor H (CFH). In some embodiments, the Complement Factor I (CFI) cofactor is Complement Receptor 1 (CR1) or a fragment thereof. In some embodiments, the Complement Factor I (CFI) cofactor is Membrane Cofactor Protein (MCP) or a fragment thereof.

In preferred embodiments, the Complement Factor I (CFI) cofactor is Complement Factor H Like Protein 1 (FHL1).

In some embodiments, the AAV ITRs are AAV2 or AAV8 ITRs. In preferred embodiments, the AAV ITRs are AAV2 ITRs.

In some embodiments, the nucleotide sequences encoding the Complement Factor I (CFI) cofactor, such as FHL1 or CFH, are codon optimised. In some embodiments, the nucleotide sequence encoding CFI is codon optimised. In preferred embodiments, the nucleotide sequences encoding the Complement Factor I (CFI) cofactor, such as FHL1 or CFH, and CFI are codon optimised.

In some embodiments, the nucleotide sequence encoding FHL1 has at least 75%, 80%, 85%, 86%, 87%, 88%, 89%, 90%, 91%, 92%, 93%, 94%, 95%, 96%, 97%, 98% or 99% identity to SEQ ID NO: 12.

In preferred embodiments, the nucleotide sequence encoding FHL1 is SEQ ID NO: 12.

In some embodiments, the nucleotide sequence encoding CFI has at least 75%, 80%, 85%, 86%, 87%, 88%, 89%, 90%, 91%, 92%, 93%, 94%, 95%, 96%, 97%, 98% or 99% identity to SEQ ID NO: 10.

In preferred embodiments, the nucleotide sequence encoding CFI is SEQ ID NO: 10.

In preferred embodiments, the nucleotide sequence encoding FHL1 is SEQ ID NO: 12 and the nucleotide sequence encoding CFI is SEQ ID NO: 10.

In some embodiments, the polynucleotide comprises the nucleotide sequence of SEQ ID NO: 22, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

In some embodiments, the polynucleotide comprises the nucleotide sequence of SEQ ID NO: 23, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

In some embodiments, the polynucleotide is less than or equal to 5.2, 5.1, 5.0, 4.9, 4.8 or 4.7 kb. In preferred embodiments, the polynucleotide is less than or equal to 4.7 kb.

In another aspect, the invention provides a vector comprising the polynucleotide of the invention.

In some embodiments, the vector is an adeno-associated viral (AAV), retroviral, lentiviral or adenoviral vector.

In preferred embodiments, the vector is an AAV vector.

In some embodiments, the vector is in the form of a viral vector particle.

In some embodiments, the AAV vector particle comprises an AAV2 or AAV8 genome.

In some embodiments, the AAV vector particle comprises AAV2 or AAV8 capsid proteins.

In some embodiments, the AAV vector particle comprises an AAV2 genome and AAV2 capsid proteins (AAV2/2). In other embodiments, the AAV vector particle comprises an AAV2 genome and AAV8 capsid proteins (AAV2/8). In other embodiments, the AAV vector particle comprises an AAV8 genome and AAV8 capsid proteins (AAV8/8).

In another aspect, the invention provides a cell comprising the polynucleotide of the invention.

In another aspect, the invention provides a cell transduced with the vector of the invention.

In another aspect, the invention provides a pharmaceutical composition comprising the polynucleotide, vector or cell of the invention in combination with a pharmaceutically acceptable carrier, diluent or excipient.

In preferred embodiments, the pharmaceutical composition is for intraocular administration.

In another aspect, the invention provides the polynucleotide, vector or cell of the invention for use in therapy.

In another aspect, the invention provides the polynucleotide, vector or cell of the invention for use in treating or preventing an ocular disorder.

In another aspect, the invention provides the polynucleotide, vector or cell of the invention for use in treating or preventing a complement-mediated or a complement-associated disorder.

In another aspect, the invention provides the polynucleotide, vector or cell of the invention for use in treating or preventing a complement-mediated disorder of the eye.

In another aspect, the invention provides the polynucleotide, vector or cell of the invention for use in treating or preventing a complement-mediated or complement-associated renal disorder or complement-mediated or complement-associated disorder of the central nervous system (CNS).

In another aspect, the invention provides a method of treating or preventing a complement-mediated or complement associated disorder of the eye comprising administering the polynucleotide, vector or cell of the invention to a subject in need thereof.

In another aspect, the invention provides a method of providing (i) a Complement Factor I (CFI) cofactor; and (ii) Complement Factor I (CFI) to a subject, comprising delivering the polynucleotide, vector or cell of the invention to the subject, preferably to the eye of the subject.

In another aspect, the invention provides a method of providing (i) Complement Factor H Like Protein 1 (FHL1) or Complement Factor H (CFH); and (ii) Complement Factor I (CFI) to a subject, comprising delivering the polynucleotide, vector or cell of the invention to the eye of the subject.

In some embodiments, the disorder is associated with over-activity of the complement C3b feedback cycle and/or under-activity of the C3b breakdown cycle (see FIG. 1).

In some embodiments, the disorder is a chronic complement-mediated or chronic complement-associated inflammatory condition.

In some embodiments, the disorder is a chronic complement-mediated inflammatory condition of the eye.

In some embodiments, the disorder is age-related macular degeneration (AMD) or diabetic retinopathy. In other embodiments, the disorder is glaucoma, Stargardt's disease, central serous chorioretinopathy, retinitis pigmentosa or uveitis. Preferably, the uveitis is posterior uveitis.

In preferred embodiments, the disorder is AMD. In some embodiments, the AMD is dry AMD.

In some embodiments, a subject has been diagnosed with AMD or is at risk of acquiring AMD.

In some embodiments, the use is for treating or preventing a disorder in a subject:

(a) having lower than normal Complement Factor I activity or concentration in the eye and/or serum, preferably having a concentration of, or activity equivalent to, 0-30, 0-20 or 0-10 μg/mL in serum; and/or (b) being heterozygous or homozygous for an age-related macular degeneration (AMD)-associated SNP, preferably a rare Complement Factor I variant.

In some embodiments, the use is for treating or preventing a disorder in a subject:

(a) having a normal level of Complement Factor I activity or concentration in the eye and/or serum, preferably at least 30 μg/mL, such as 30-40 μg/mL in serum; and/or (b) not carrying a rare Complement Factor I variant allele.

In another aspect, the invention provides the polynucleotide, vector or cell of the invention for use in treating or preventing age-related macular degeneration (AMD). In preferred embodiments, the AMD is dry AMD.

In another aspect, the invention provides the polynucleotide, vector or cell of the invention for use in treating or preventing diabetic retinopathy.

In some embodiments, the formation of geographic atrophy is prevented or reduced, and/or the amount of geographic atrophy is reduced.

In some embodiments, the progression of geographic atrophy is slowed.

In some embodiments, there is at least a 10% reduction in the increase in geographic atrophy area over the 12 months following administration to a treated eye of a subject, relative to an untreated eye over the same period. In other embodiments, there is at least 20%, 30%, 40%, 50%, 60%, 70%, 80% or 90% reduction in the increase in geographic atrophy area over the 12 months following administration to a treated eye of a subject, relative to an untreated eye over the same period In some embodiments, administration of the polynucleotide, vector or cell increases the level of C3b-inactivating and iC3b-degradation activity in a subject, or in an eye, such as in the retinal pigment epithelium (RPE), of a subject, optionally to a level that exceeds a normal level in a subject, or eye or RPE thereof.

In another aspect, the invention provides the polynucleotide, vector or cell of the invention for use in improving or restoring vision or visual acuity, for example in a subject suffering from an eye disorder, such as an eye disorder disclosed herein. In another aspect, the invention provides the polynucleotide, vector or cell of the invention for use in mitigating loss of vision or visual acuity, for example a loss of vision or visual acuity associated with an eye disorder, such as an eye disorder disclosed herein.

In another aspect, the invention provides the polynucleotide, vector or cell of the invention for use in improving or restoring reading speed in a subject, for example in a subject suffering from an eye disorder, such as an eye disorder disclosed herein. In another aspect, the invention provides the polynucleotide, vector or cell of the invention for use in mitigating reduction in reading speed in a subject, for example a reduction in reading speed associated with an eye disorder, such as an eye disorder disclosed herein.

In another aspect, the invention provides the polynucleotide, vector or cell of the invention for use in reducing or preventing loss of photoreceptors and/or the retinal pigment epithelium (RPE), for example a loss of photoreceptors and/or the RPE associated with an eye disorder, such as an eye disorder disclosed herein.

In some embodiments, the polynucleotide, vector or cell is administered intraocularly.

In some embodiments, the polynucleotide, vector or cell is administered to the eye of a subject by subretinal, direct retinal, suprachoroidal or intravitreal injection.

In some embodiments, the polynucleotide, vector or cell is administered to the eye of a subject by subretinal injection.

In some embodiments, the polynucleotide or vector of the invention does not comprise a hAAT promoter. In some embodiments, the polynucleotide or vector of the invention does not comprise an ApoR enhancer. In other embodiments, the polynucleotide or vector of the invention does not comprise two ApoR enhancers.

In some embodiments, the vector of the invention does not comprise an AAV2 genome and an AAV8 capsid protein, i.e. the vector of the invention is not an AAV2/8 vector.

In some embodiments, the polynucleotide, vector or cell of the invention is not administered systemically. In other embodiments, the polynucleotide, vector or cell of the invention is not administered intravenously.

It will be understood by those skilled in the art that the descriptions above relating to the treatment of AMD are based on a theory of modulating hyperactivated complement system (either as a result of overactive C3b feedback cycle and/or underactive C3b breakdown cycle) and therefore (with the exception of text specifically relating to intraocular administration) the description applies equally to other chronic inflammatory conditions in which the complement system is implicated. Such disorders may be treated by administration of the products, proteins, vectors, cells and compositions described herein by systemic administration (for example via peripheral vein infusion), local administration (for example intrathecally) or direct delivery to targeted tissue or organs (for example, liver, kidney).

Figure 1:
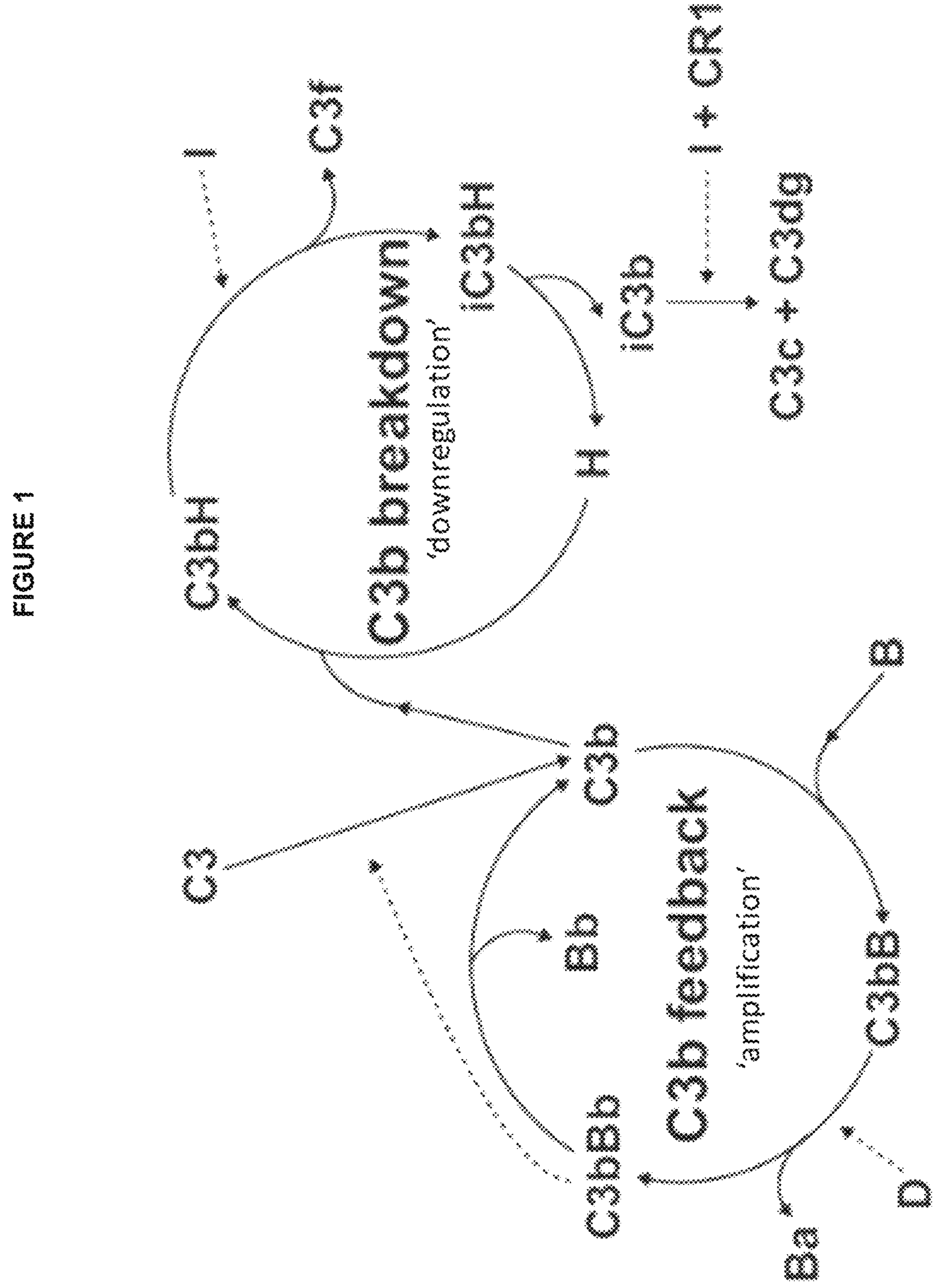
FIG. 1

C3b feedback (amplification) and breakdown (down-regulation) cycles of the alternative pathway of vertebrate complement ("I"=Complement Factor I; "H"=Complement Factor H; "B"=Complement Factor B; and "D"=Complement Factor D).

FIG. 2

(A) Cofactor assay based on ELISA-based measurement of cleavage of C3b to iC3b. Concentrations of CFI and C3b were fixed, and titrations of CFH or FHL1 in specified ratios were carried out.

(B) LPS deposition assay based on supplementation of normal serum with Complement Factor I (FI), Complement Factor H (FH) or Complement Factor H-like Protein 1 (FHL1).

FIG. 3

Western blot analyses of supernatants from vector transduction of HEK293 cells (RC001, control vector comprising wild-type FHL1; GT005, control vector comprising wild-type CFI).

FIG. 4

ELISA analyses of supernatants from vector transduction of HEK293 cells (RC001, control vector comprising wild-type FHL1; GT005, control vector comprising wild-type CFI).

FIG. 5

Alkaline gel analyses of vector genome packaging (top panel). Comparison of the ratio of full: empty viral particles determined by qPCR and capsid ELISA (bottom panel). (RC001, control vector comprising wild-type FHL1; GT005, control vector comprising wild-type CFI).

FIG. 6

C3b cleavage assays using Western blot analysis (top panel) and ELISA (bottom panel). (RC001, control vector comprising wild-type FHL1; GT005, control vector comprising wild-type CFI).

FIG. 7

Comparison of Complement Factor I (FI): Complement Factor H (FH) ratios in blood plasma (n=80) and vitreous humour (n=29).

FIG. 8

LPS deposition assay to measure C3 deposition. FI=Complement Factor I, sCR1=soluble complement receptor 1, FH=Complement Factor H, FHL1=Factor H-like protein 1. Number above each bar shows the % of reduction in C3 deposition compared to serum only.

FIG. 9

Western blot analysis of supernatant of in vitro transduced HEK-293 cells. UTC=untransduced cells, GT005=AAV expressing CFI, GT007=AAV expressing CFI and FHL1, RC001=AAV expressing FHL1.

FIG. 10

C3b Western blot and iC3b ELISA of cofactor assay to test functional activity of constructs. (A) Western blot of C3b cofactor assay. (B) iC3b ELISA of C3b cofactor assay. C3b=Complement C3b, CFI=Complement Factor I, FHL1=Complement Factor H-like protein 1, UTD=untransduced cells.

FIG. 11

Isolectin-stained area in choroidal flatmounts. Isolectin stained area data were non-normally distributed as assessed by Kolmogorov-Smirnov test and statistical significance of the observed differences was determined using Generalised Linear Model analysis. *=$P<0.05$; *=$P<0.0001$, **=$P<0.00001$. Dots represent results from individual laser burns, the line represents the mean value.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Complement System

The complement system is an integral part of the humoral immune system and is involved in tissue inflammation, cell opsonisation, and cytolysis. It provides protection against microorganisms and mediates the clearance of exogenous and endogenous cellular debris from the host tissues.

The complement system cascade is comprised of three activation pathways. All of the pathways ultimately end in the central cleavage of C3 factor and in the generation of its active fragments C3a and C3b. C3a is the anaphylatoxin that triggers a range of chemotactic and proinflammatory responses, such as recruitment of inflammatory cells and increased microvasculature permeability, whereas C3b is responsible for opsonisation of foreign surfaces covalently attached to C3b. Opsonisation with activated C3 fragments (C3b and iC3b) fulfils three major functions: (i) cell debris elimination by phagocytic cells (e.g. macrophages or microglia) and the stimulation of the adaptive immune system (B and T cells); (ii) amplification of complement activation via the formation of a surface-bound C3 convertase; and (iii) assemblage of the C5 convertase.

Assemblage of the C5 convertase is responsible for C5 cleavage, which results in the formation of the cytolytic membrane attack complex (MAC) capable of generating perforations in the cell membrane, thereby promoting cell lysis and the elimination of unnecessary cells. Through all of these activities, the innate complement cascade supports and promotes the function of downstream mechanisms of the immune system that protect the integrity of the host tissue. Overall, complement system pathway activation results in a proinflammatory response, including MAC generation, which mediates cell lysis, the release of chemokines to attract inflammatory cells to the site of damage, and the enhancement of capillary permeability to promote extravasation of infiltrating leukocytes. Under physiological conditions, complement activation is effectively controlled by the coordinated action of soluble and membrane-associated complement regulatory molecules (CRMs). Soluble complement regulators, such as C1-inhibitor, anaphylatoxins inhibitor, C4b binding protein (C4BP), Complement Factor H (CFH), Complement Factor I (CFI), clusterin and vitronectin, restrict the action of complement in human tissues at multiple sites of the cascade reaction. In addition, each individual cell is protected against the attack of homologous complement by surface proteins, such as the Complement Receptor 1 (CR1, CD35), the membrane cofactor protein (CD46), and glycosylphosphatidylinositol-anchored proteins, such as decay-accelerating factor (CD55) or CD59 molecule. Of note, host cells and tissues that are inadequately protected from complement attack might be subjected to bystander cell lysis.

The invention relates to the treatment or prevention of a complement-mediated disorder, for example of the eye. For example, the complement-mediated disorder may be a disorder associated with a defect in alternative pathway regulation, and in particular with over-activity of the complement C3b feedback cycle and/or under-activity of the C3b breakdown cycle.

In some embodiments, prior to administration of the product, polynucleotide, vector, cell or pharmaceutical composition of the invention, the subject has low levels (e.g. lower than normal levels) of Complement Factor I activity, for example low levels of Complement Factor I activity in the eye and/or low serum levels of Complement Factor I activity. The sub-normal level of Complement Factor I activity may be due to sub-normal expression of normally-functioning Complement Factor I, or at least partial (e.g. heterozygous) expression (at normal or sub-normal levels) of a non- or sub-functional variant of Complement Factor I. (Such a subject may carry one or more copies of an AMD-associated SNP, for example the subject may be homo- or heterozygous for one of the rare Complement Factor I variants discussed further below). Thus, the subject may have a low concentration (e.g. a lower than normal concentration) of Complement Factor I in the eye and/or serum. For a human subject, the normal level of Complement Factor I activity (C3b-inactivating and iC3b-degradation activity) may be equivalent to that provided by 30-40 μg/mL Complement Factor I in the serum of the subject. Thus, in a subject with low Complement Factor I activity, the Complement Factor I activity in the serum may correspond to less than 30 μg/mL and greater than 0 μg/mL Complement Factor I, such as 0-20 or 0-10 μg/mL (these being ranges of Complement Factor I serum concentration which may encompass a subject having a low Complement Factor I concentration).

Thus, the subject to be treated by the invention may suffer from a complement-mediated disorder of the eye such as AMD, more particularly dry AMD (e.g. characterised by geographic atrophy), or may be at risk of developing such a disorder. For example, the subject may be homozygous or heterozygous susceptible for one or more SNPs associated with the complement-mediated disorder.

In some embodiments, the subject is at risk of developing AMD. For example, the subject may be homozygous or heterozygous susceptible for one or more SNPs associated with AMD, for example rare mutations in Complement Factor I associated with advanced AMD which commonly result in reduced serum Complement Factor I levels (Kavanagh et al. (2015) Hum Mol Genet 24:3861-3870). In particular the subject may carry one or two copies of one or more of the following rare Complement Factor I variants: rs144082872 (encoding P50A); 4:110687847 (encoding P64L); rs141853578 (encoding G119R); 4:110685721 (encoding V152M); 4:110682846 (encoding G162D); 4:110682801 (encoding N1771); rs146444258 (encoding A240G); rs182078921 (encoding G287R); rs41278047 (encoding K441R); and rs121964913 (encoding R474).

The invention may further comprise determining whether the subject is at risk of developing a complement-mediated disorder (for example, AMD), for example by determining whether the subject is homozygous or heterozygous susceptible for one or more SNPs associated with the complement-mediated disorder (for example, by determining whether the subject is homozygous or heterozygous susceptible for one or more of the rare Complement Factor I variants associated with AMD listed above).

Alternatively, the subject may have a normal level of endogenous Complement Factor I activity or concentration, for example in the eye and/or serum and/or may not carry a rare variant Complement Factor I allele.

In some embodiments, administration of the product, polynucleotide, vector, cell or pharmaceutical composition of the invention thereby increases the level of C3b-inactivating and iC3b-degradation activity in the eye of the subject. In other embodiments, administration of the product, polynucleotide, vector, cell or pharmaceutical composition of the invention thereby increases the level of C3b-inactivating and iC3b-degradation activity in the eye of the subject to a level that exceeds a normal level in the eye. More particularly, the level of C3b-inactivating and iC3b-degradation activity is increased in the RPE of the eye.

It will be appreciated that the C3b-inactivating and iC3b-degradation activity in the subject following provision of the product of the invention and/or expression of the Complement Factor I and CFI cofactor, such as Complement Factor H-like Protein 1, from the polynucleotide or vector of the invention may comprise C3b-inactivating and iC3b-degradation activity from the subject's endogenous Complement Factor I (i.e. the subject's Complement Factor I not provided by the product or produced by expression from the polynucleotide or vector), and C3b-inactivating and iC3b-degradation activity provided by the product of the invention or produced by expression from the polynucleotide or vector of the invention, such that the total level of C3b-inactivating and iC3b-degradation activity in the subject exceeds a normal level.

In some embodiments, the level of C3b-inactivating and iC3b-degradation activity in the subject, for example in the eye, is increased to a level that is at least 5%, 10%, 15%, 20% or 25% above the normal level.

In other embodiments, the level of C3b-inactivating and iC3b-degradation activity in the subject, for example in the eye, is increased to a level that is up to twice the normal level, or up to 80%, 60%, 40% or 20% above the normal level.

For example, the level of C3b-inactivating and iC3b-degradation activity in the subject, for example in the eye, may be increased to a level that is 5-100%, 5-80%, 5-60%, 5-40%, 5-20%, 10-100%, 10-80%, 10-60%, 10-40%, 10-20%, 15-100%, 15-80%, 15-60%, 15-40%, 15-20%, 20-100%, 20-80%, 20-60%, 20-40%, 25-100%, 25-80%, 25-60% or 25-40% above the normal level.

In some embodiments, administration of the product, polynucleotide, vector, cell or pharmaceutical composition of the invention does not detectably increase the level of C3b-inactivating and iC3b-degradation activity in the plasma/serum of the subject. In other embodiments, administration of the product, polynucleotide, vector, cell or pharmaceutical composition of the invention does not detectably increase the level of C3b-inactivating and iC3b-degradation activity in the plasma/serum of the subject to a level greater than the normal level.

In the foregoing section, except where obviously inapplicable, reference to Complement Factor I and C3b-inactivating and iC3b-degradation activity may be replaced with a CFI cofactor, preferably Complement Factor H or Complement Factor H-like Protein 1, and ability to act as a cofactor for the Complement Factor I mediated cleavage of C3b and to increase the rate of dissociation of C3 convertase and C5 convertase, respectively. In some embodiments, prior to administration of the product, polynucleotide, vector, cell or pharmaceutical composition of the invention, the subject has low levels (e.g. lower than normal levels) of Complement Factor H, for example low levels of Complement Factor H in the eye and/or low serum levels of Complement Factor H. For a human subject, the normal level of Complement Factor H may be about 200-500 μg/mL in the serum of the subject. Thus, in a subject with low levels of Complement Factor H, the levels in the serum may be less than 200 μg/mL and greater than 0 μg/mL, such as 0-100 μg/mL. Alternatively, the subject may have a normal level of endogenous Complement Factor H, for example in the eye and/or serum.

Complement Factor I (CFI)

Complement Factor I (Factor I, CFI), also known as C3b/C4b inactivator, is a protein that in humans is encoded by the CFI gene.

Complement Factor I is a serine protease that circulates in a zymogen-like state (Roversi et al. (2011) PNAS 108: 12839-12844) at a concentration of ~35 μg/mL (Nilsson et al. (2011) Mol Immunol 48: 1611-1620). The Complement Factor I protein is a heavily N-glycosylated heterodimer consisting of two polypeptide chains linked by a single disulfide bond. The heavy chain (50 kDa) comprises an N-terminal region; an FI membrane attack complex (FIMAC) domain; a CD5 like-domain or scavenger receptor cysteine-rich (SRCR) domain; two low-density lipoprotein receptor (LDLr) domains; and a C-terminal region of unknown function that is a site of sequence variability across species (Roversi et al. (2011) PNAS 108: 12839-12844). The light chain (38 kDa) contains the serine protease (SP) domain with the conserved catalytic residues (Goldberger et al. (1987) J Biol Chem 262: 10065-10071).

Complement Factor I inactivates C3b by cleaving it into iC3b, C3d and C3d,g and, in an analogous way, C4b into C4c and C4d. To properly perform its functions, Complement Factor I requires the presence of cofactor proteins such as C4b-Binding Protein (C4BP), Complement Factor H (CFH), Complement Receptor 1 (CR1/CD35) and Membrane Cofactor Protein (MCP/CD46) (Degn et al. (2011) Am J Hum Genet 88: 689-705).

iC3b is incapable of associating with Factor B, and thus cannot perpetuate amplification of the complement cascade or activation through the alternative pathway. Hence, once C3b has been cleaved to iC3b, neither alternative pathway initiation nor terminal complement cascade activation occurs.

iC3b is capable of providing a proinflammatory action by binding to, and activating, Complement Receptor 3 (CR3) (CD11b/CD18) on polymorphonuclear leukocytes (mostly neutrophils), NK cells and mononuclear phagocytes, such as macrophages.

Complement Factor I is capable of processing iC3b into C3dg via a protease activity requiring the cofactor, CR1. C3dg is unable to bind to CR3. Since iC3b reacting with the complement receptor CR3 is a major mechanism by which complement activation gives rise to inflammation, the breakdown of iC3b to C3dg is essential for reducing complement-induced inflammation (Lachmann (2009) Adv. Immunol. 104: 115-149).

Complement Factor I's unique ability to both promote cleavage of C3b to iC3b as well as accelerate breakdown of iC3b—combined with its relatively low concentration in human serum, with implications for the amount required to be delivered for therapeutic efficacy—make it a particularly advantageous target.

In some embodiments, a Complement Factor I polypeptide is capable of cleaving C3b into an inactive degradation product. For example, the Complement Factor I polypeptide may be capable of cleaving C3b into iC3b.

In some embodiments, a Complement Factor I polypeptide is capable of processing iC3b into an inactive degradation product. For example, the Complement Factor I polypeptide may be capable of processing iC3b into C3dg.

In preferred embodiments, the Complement Factor I polypeptide is capable of cleaving C3b into iC3b and processing iC3b into C3dg.

Suitably, a fragment or derivative of Complement Factor I may retain at least 50%, 60%, 70%, 80%, 90%, 95% or 100% of the C3b-inactivating and iC3b-degradation activity of native Complement Factor I.

The C3b-inactivating and iC3b-degradation activity of Complement Factor I, or a fragment or derivative thereof, may be determined using any suitable method known to the skilled person. For example, measurement of Complement Factor I proteolytic activity is described in Hsiung et al. (Biochem. J. (1982) 203: 293-298). Both haemolytic and conglutinating assays for CFI activity are described in Lachmann PJ & Hobart MJ (1978) "Complement Technology" in Handbook of Experimental Immunology 3rd edition Ed DM Weir Blackwells Scientific Publications Chapter 5A p17. A more detailed description, also including a proteolytic assay, is given by Harrison RA (1996) in "Weir's Handbook of Experimental Immunology" 5th Edition Eds; Herzenberg Leonore A' Weir D M, Herzenberg Leonard A & Blackwell C Blackwells Scientific Publications Chapter 75 36-37. The conglutinating assay is highly sensitive and can be used for detecting both the first (double) clip converting fixed C3b to iC3b and acquiring reactivity with conglutinin; and for detecting the final clip to C3dg by starting with fixed iC3b and looking for the loss of reactivity with conglutinin. The haemolytic assay is used for the conversion of C3b to iC3b, and the proteolytic assay detects all the clips.

In some embodiments, the Complement Factor I is human Complement Factor I.

An example human Complement Factor I protein is the human Complement Factor I protein having the UniProtKB accession number P05156. This exemplified sequence is 583 amino acids in length (disclosed as SEQ ID NO: 1) of which amino acids 1 to 18 form a signal sequence.

In some embodiments, the amino acid sequence of Complement Factor I is SEQ ID NO: 1. In other embodiments, the amino acid sequence of Complement Factor I is the sequence disclosed as positions 19 to 583 of SEQ ID NO: 1.

(SEQ ID NO: 1)

```
MKLLHVFLLFLCFHLRFCKVTYTSQEDLVEKKCLAKKYTHLSCDKVFCQ
PWQRCIEGTCVCKLPYQCPKNGTAVCATNRRSFPTYCQQKSLECLHPGT
KFLNNGTCTAEGKFSVSLKHGNTDSEGIVEVKLVDQDKTMFICKSSWSM
REANVACLDLGFQQGADTQRRFKLSDLSINSTECLHVHCRGLETSLAEC
TFTKRRTMGYQDFADVVCYTQKADSPMDDFFQCVNGKYISQMKACDGIN
DCGDQSDELCCKACQGKGFHCKSGVCIPSQYQCNGEVDCITGEDEVGCA
GFASVTQEETEILTADMDAERRRIKSLLPKLSCGVKNRMHIRRKRIVGG
KRAQLGDLPWQVAIKDASGITCGGIYIGGCWILTAAHCLRASKTHRYQI
WITVVDWIHPDLKRIVIEYVDRIIFHENYNAGTYQNDIALIEMKKDGNK
KDCELPRSIPACVPWSPYLFQPNDTCIVSGWGREKDNERVFSLQWGEVK
LISNCSKFYGNRFYEKEMECAGTYDGSIDACKGDSGGPLVCMDANNVTY
VWGVVSWGENCGKPEFPGVYTKVANYFDWISYHVGRPFISQYNV
```

In some embodiments, the amino acid sequence of Complement Factor I is SEQ ID NO: 9, which corresponds to NCBI Accession No. NP_000195. In other embodiments, the amino acid sequence of Complement Factor I is the sequence disclosed as positions 19 to 583 of SEQ ID NO: 9.

(SEQ ID NO: 9)

```
MKLLHVFLLFLCFHLRFCKVTYTSQEDLVEKKCLAKKYTHLSCDKVFCQ
PWQRCIEGTCVCKLPYQCPKNGTAVCATNRRSFPTYCQQKSLECLHPGT
KFLNNGTCTAEGKFSVSLKHGNTDSEGIVEVKLVDQDKTMFICKSSWSM
REANVACLDLGFQQGADTQRRFKLSDLSINSTECLHVHCRGLETSLAEC
TFTKRRTMGYQDFADVVCYTQKADSPMDDFFQCVNGKYISQMKACDGIN
DCGDQSDELCCKACQGKGFHCKSGVCIPSQYQCNGEVDCITGEDEVGCA
GFASVAQEETEILTADMDAERRRIKSLLPKLSCGVKNRMHIRRKRIVGG
KRAQLGDLPWQVAIKDASGITCGGIYIGGCWILTAAHCLRASKTHRYQI
WTTVVDWIHPDLKRIVIEYVDRIIFHENYNAGYQNDIALIEMKKDGNKK
DCELPRSIPACVPWSPYLFQPNDTCIVSGWGREKDNERVFSLQWGEVKL
ISNCSKFYGNRFYEKEMECAGTYDGSIDACKGDSGGPLVCMDANNVTYV
WGVVSWGENCGKPEFPGVYTKVANYFDWISYHVGRPFISQYNV
```

An example wild type nucleotide sequence encoding Complement Factor I is the nucleotide sequence having the NCBI Accession No. NM_000204, disclosed herein as SEQ ID NO: 2.

(SEQ ID NO: 2)

```
ATGAAGCTTCTTCATGTTTTCCTGTTATTTCTGTGCTTCCACTTAAGGT
TTTGCAAGGTCACTTATACATCTCAAGAGGATCTGGTGGAGAAAAAGTG
CTTAGCAAAAAAATATACTCACCTCTCCTGCGATAAAGTCTTCTGCCAG
CCATGGCAGAGATGCATTGAGGGCACCTGTGTTTGTAAACTACCGTATC
AGTGCCCAAAGAATGGCACTGCAGTGTGTGCAACTAACAGGAGAAGCTT
CCCAACATACTGTCAACAAAAGAGTTTGGAATGTCTTCATCCAGGGACA
AAGTTTTTAAATAACGGAACATGCACAGCCGAAGGAAAGTTTAGTGTTT
CCTTGAAGCATGGAAATACAGATTCAGAGGGAATAGTTGAAGTAAAACT
TGTGGACCAAGATAAGACAATGTTCATATGCAAAAGCAGCTGGAGCATG
AGGGAAGCCAACGTGGCCTGCCTTGACCTTGGGTTTCAACAAGGTGCTG
ATACTCAAAGAAGGTTTAAGTTGTCTGATCTCTCTATAAATTCCACTGA
ATGTCTACATGTGCATTGCCGAGGATTAGAGACCAGTTTGGCTGAATGT
ACTTTTACTAAGAGAAGAACTATGGGTTACCAGGATTTCGCTGATGTGG
TTTGTTATACACAGAAAGCAGATTCTCCAATGGATGACTTCTTTCAGTG
GTGAATGGGAAATACATTTCTCAGATGAAAGCCTGTGATGGTATCAATG
ATTGTGGAGACCAAAGTGATGAACTGTGTTGTAAAGCATGCCAAGGCAA
AGGCTTCCATTGCAAATCGGGTGTTTGCATTCCAAGCCAGTATCAATGC
AATGGTGAGGTGGACTGCATTACAGGGGAAGATGAAGTTGGCTGTGCAG
GCTTTGCATCTGTGGCTCAAGAAGAAACAGAAATTTTGACTGCTGACAT
GGATGCAGAAAGAAGACGGATAAAATCATTATTACCTAAACTATCTTGT
GGAGTTAAAAACAGAATGCACATTCGAAGGAAACGAATTGTGGGAGGAA
AGCGAGCACAACTGGGAGACCTCCCATGGCAGGTGGCAATTAAGGATGC
CAGTGGAATCACCTGTGGGGGAATTTATATTGGTGGCTGTTGGATTCTG
ACTGCTGCACATTGTCTCAGAGCCAGTAAAACTCATCGTTACCAAATAT
GGACAACAGTAGTAGACTGGATACACCCCGACCTTAAACGTATAGTAAT
TGAATACGTGGATAGAATTATTTTCCATGAAAACTACAATGCAGGCACT
TACCAAAATGACATCGCTTTGATTGAAATGAAAAAAGACGGAAACAAAA
AAGATTGTGAGCTGCCTCGTTCCATCCCTGCCTGTGTCCCCTGGTCTCC
TTACCTATTCCAACCTAATGATACATGCATCGTTTCTGGCTGGGGACGA
GAAAAAGATAACGAAAGAGTCTTTTCACTTCAGTGGGGTGAAGTTAAAC
TAATAAGCAACTGCTCTAAGTTTTACGGAAATCGTTTCTATGAAAAAGA
AATGGAATGTGCAGGTACATATGATGGTTCCATCGATGCCTGTAAAGGG
GACTCTGGAGGCCCCTTAGTCTGTATGGATGCCAACAATGTGACTTATG
TCTGGGGTGTTGTGAGTTGGGGGGAAAACTGTGGAAAACCAGAGTTCCC
AGGTGTTTACACCAAAGTGGCCAATTATTTTGACTGGATTAGCTACCAT
GTAGGAAGGCCTTTTATTTCTCAGTACAATGTATAA
```

In some embodiments, the nucleotide sequences of Complement Factor I used in the invention are codon-optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

A preferred nucleotide sequence encoding Complement Factor I is the nucleotide sequence disclosed as SEQ ID NO: 10.

(SEQ ID NO: 10)

```
ATGAAACTGCTGCATGTCTTCCTCCTCTTCCTGTGCTTCCACCTCCGTT
TCTGTAAAGTCACCTACACTAGCCAGGAGGATCTGGTGGAGAAGAAATG
CCTGGCCAAGAAGTATACCCACCTGAGCTGCGACAAAGTGTTCTGCCAG
CCCTGGCAACGCTGCATTGAAGGTACTTGTGTGTGCAAGCTGCCCTACC
AGTGCCCCAAGAACGGCACGGCCGTGTGTGCCACCAACAGGAGGAGCTT
CCCCACCTACTGCCAGCAGAAGAGCCTGGAATGCCTCCACCCTGGCACC
AAGTTTCTGAACAACGGGACCTGCACAGCCGAGGGGAAATTCAGCGTCT
CCCTCAAGCACGGCAATACAGACTCCGAGGGCATTGTGGAAGTGAAGCT
GGTGGACCAGGACAAGACCATGTTCATCTGCAAAAGCAGCTGGTCCATG
CGGGAGGCCAATGTCGCCTGCCTGGACCTGGGCTTCCAGCAGGGCGCTG
ATACACAGCGCCGCTTTAAACTCAGTGACCTCAGCATCAACAGCACTGA
GTGTCTGCACGTGCACTGCCGGGGCCTGGAGACCAGCCTGGCTGAGTGC
ACCTTCACCAAGCGCAGGACCATGGGCTACCAGGATTTTGCAGATGTGG
TCTGCTACACCCAGAAGGCAGACAGCCCCATGGATGACTTCTTCCAGTG
TGTCAATGGCAAGTACATTTCCCAGATGAAGGCTTGTGACGGGATCAAT
GATTGCGGGGATCAGAGCGATGAGCTCTGCTGCAAGGCCTGCCAAGGGA
AGGGCTTTCACTGTAAGTCTGGGGTGTGCATCCCTTCTCAGTATCAGTG
CAACGGAGAGGTGGACTGCATCACTGGGGAGGACGAGGTGGGCTGTGCT
GGCTTCGCCTCTGTGGCCCAGGAGGAGACAGAGATCCTCACAGCTGACA
TGGATGCAGAGCGGCGGCGCATCAAGAGTCTGCTCCCAAAGCTCTCCTG
CGGCGTTAAGAATCGCATGCACATCCGGAGGAAGCGGATCGTTGGAGGC
AAACGGGCTCAGCTGGGGGACTTGCCGTGGCAGGTGGCCATCAAAGATG
CCTCCGGAATCACCTGTGGTGGCATCTACATCGGCGGCTGCTGGATCCT
GACCGCCGCCCACTGCCTTCGGGCCAGCAAGACTCACCGCTACCAGATC
TGGACCACCGTGGTGGATTGGATTCACCCCGACCTGAAGAGGATTGTCA
TTGAGTATGTCGACCGCATCATCTTCCATGAAAACTACAATGCCGGGAC
GTATCAGAACGACATCGCCCTCATCGAGATGAAGAAGGATGGGAACAAG
AAGGACTGTGAGCTGCCTCGCTCCATCCCCGCCTGTGTACCATGGTCTC
CGTACCTGTTCCAGCCAAATGACACATGCATCGTGAGCGGCTGGGGCCG
CGAGAAAGACAACGAGAGGGTCTTCTCCCTGCAGTGGGGTGAAGTCAAG
CTGATCAGCAACTGCTCCAAGTTCTACGGCAACCGCTTCTATGAGAAGG
AGATGGAGTGCGCCGGCACCTATGACGGCAGCATTGACGCGTGCAAGGG
AGACAGTGGGGGCCCCCTGGTCTGCATGGACGCCAACAATGTGACCTAC
GTGTGGGGAGTTGTGTCCTGGGGCGAGAACTGTGGCAAGCCTGAGTTCC
CGGGCGTGTACACAAAGGTGGCAAACTATTTTGACTGGATCTCCTATCA
CGTTGGCAGGCCCTTCATTTCACAGTACAACGTATAA
```

A further example codon-optimised nucleotide sequence encoding Complement Factor I is SEQ ID NO: 8.

```
                                          (SEQ ID NO: 8)
ATGAAGCTGCTGCATGTCTTTCTGCTGTTTCTGTGCTTCCATCTGCGGT

TCTGTAAAGTGACCTATACTAGCCAGGAGGATCTGGTGGAGAAGAAGTG

TCTGGCCAAGAAGTACACACACCTGAGCTGCGACAAGGTGTTCTGTCAG

CCTTGGCAGCGGTGCATCGAGGGCACCTGCGTGTGCAAGCTGCCTTACC

AGTGCCCAAAGAACGGCACCGCCGTGTGCGCCACAAATCGGAGATCTTT

TCCAACATATTGCCAGCAGAAGAGCCTGGAGTGTCTGCACCCCGGCACC

AAGTTCCTGAACAATGGCACCTGCACAGCCGAGGGCAAGTTTTCTGTGA

GCCTGAAGCACGGCAACACAGATAGCGAGGGCATCGTGGAGGTGAAGCT

GGTGGACCAGGATAAGACCATGTTCATCTGTAAGAGCTCCTGGTCCATG

AGGGAGGCAAACGTGGCATGCCTGGATCTGGGATTCCAGCAGGGAGCAG

ACACACAGAGGCGCTTTAAGCTGTCCGACCTGTCTATCAATAGCACCGA

GTGCCTGCACGTGCACTGTAGGGGCCTGGAGACATCCCTGGCAGAGTGC

ACCTTCACAAAGCGGAGAACCATGGGCTACCAGGACTTTGCCGACGTGG

TGTGCTATACCCAGAAGGCCGATAGCCCCATGGACGATTTCTTTCAGTG

CGTGAACGGCAAGTATATCTCCCAGATGAAGGCCTGCGACGGCATCAAT

GACTGTGGCGATCAGTCTGACGAGCTGTGCTGTAAGGCCTGTCAGGGCA

AGGGCTTCCACTGCAAGAGCGGCGTGTGCATCCCTTCCCAGTACCAGTG

CAACGGCGAGGTGGATTGTATCACAGGAGAGGACGAAGTGGGATGCGCA

GGATTTGCATCTGTGGCACAGGAGGAGACAGAGATCCTGACAGCCGACA

TGGATGCCGAGAGGCGCCGGATCAAGTCTCTGCTGCCTAAGCTGAGCTG

TGGCGTGAAGAATCGGATGCACATCAGAAGGAAGCGCATCGTGGGAGGC

AAGAGGGCACAGCTGGGCGATCTGCCATGGCAGGTGGCCATCAAGGACG

CCTCTGGCATCACCTGCGGCGGCATCTACATCGGAGGATGTTGGATCCT

GACCGCAGCACACTGCCTGAGAGCAAGCAAGACACACAGGTATCAGATC

TGGACCACAGTGGTGGATTGGATCCACCCAGACCTGAAGAGAATCGTGA

TCGAGTACGTGGATAGGATCATCTTTCACGAGAACTACAATGCCGGCAC

ATATCAGAACGACATCGCCCTGATCGAGATGAAGAAGGATGGCAATAAG

AAGGACTGTGAGCTGCCCAGATCCATCCCTGCATGCGTGCCATGGAGCC

CCTATCTGTTCCAGCCCAACGATACCTGCATCGTGTCCGGATGGGGAAG

GGAGAAGGACAATGAGCGGGTGTTTTCTCTGCAGTGGGGCGAGGTGAAG

CTGATCTCCAACTGTTCTAAGTTCTACGGCAATAGGTTTTATGAGAAGG

AGATGGAGTGCGCCGGCACCTACGATGGCAGCATCGACGCCTGTAAGGG

CGATTCCGGAGGACCACTGGTGTGCATGGACGCAAACAATGTGACATAC

GTGTGGGGAGTGGTGTCCTGGGGAGAGAACTGCGGCAAGCCAGAGTTCC

CCGGCGTATATACCAAGGTGGCCAATTATTTTGATTGGATTTCCTACCA

CGTCGGCAGGCCCTTTATTTCCCAGTATAATGTCTAA
```

In some embodiments, the nucleotide sequence encoding Complement Factor I has at least 75%, 80%, 85%, 86%, 87%, 88%, 89%, 90%, 91%, 92%, 93%, 94%, 95%, 96%, 97%, 98% or 99% identity to SEQ ID NO: 10, 8 or 2, preferably SEQ ID NO: 10. Preferably, the protein encoded by the nucleotide sequence substantially retains a functional activity of the protein represented by SEQ ID NO: 1 or 9.

In other embodiments, the nucleotide sequence encoding Complement Factor I is SEQ ID NO: 10, 8 or 2, preferably SEQ ID NO: 10.

In other embodiments, the nucleotide sequence encoding Complement Factor I has at least 75%, 80%, 85%, 90%, 91%, 92%, 93%, 94%, 95%, 96%, 97%, 98% or 99% identity to positions 55 to 1752 of SEQ ID NO: 10, 8 or 2, preferably SEQ ID NO: 10. Preferably, the protein encoded by the nucleotide sequence substantially retains a functional activity of the protein represented by SEQ ID NO: 1 or 9.

In other embodiments, the nucleotide sequence encoding Complement Factor I is positions 55 to 1752 of SEQ ID NO: 10, 8 or 2, preferably SEQ ID NO: 10.

In other embodiments, the nucleotide sequence encoding Complement Factor I encodes an amino acid sequence that has at least 75%, 80%, 85% 90%, 95%, 96%, 97%, 98% or 99% identity to SEQ ID NO: 1 or 9. Preferably, wherein the amino acid sequence substantially retains a functional activity of the protein represented by SEQ ID NO: 1 or 9.

In other embodiments, the nucleotide sequence encoding Complement Factor I encodes the amino acid sequence SEQ ID NO: 1 or 9.

In other embodiment, the nucleotide sequence encoding Complement Factor I encodes an amino acid sequence that has at least 75%, 80%, 85%, 90%, 95%, 96%, 97%, 98%, 99% identity to positions 19 to 583 of SEQ ID NO: 1 or 9. Preferably, wherein the amino acid sequence substantially retains a functional activity of the protein represented by SEQ ID NO: 1 or 9.

In other embodiments, the nucleotide sequence encoding Complement Factor I encodes the amino acid sequence of positions 19 to 583 of SEQ ID NO: 1 or 9.

An advantage of the invention is that Complement Factor I is particularly difficult to prepare in the form of a purified protein. Accordingly, the inventors have devised a way of modulating the complement system, for example to enable treatments of age-related macular degeneration (AMD), by administering Complement Factor I in the form of an AAV vector comprising a Complement Factor I-encoding nucleotide sequence. The AAV vector may be administered to a site of interest, for example the eye, to enable in situ translation of the Complement Factor I polypeptide.

Complement Factor I (CFI) Cofactor

The term "Complement Factor I (CFI) cofactor", as used herein, may refer to a protein that is capable of acting as a cofactor for the CFI-mediated cleavage of C3b.

In some embodiments, the Complement Factor I (CFI) cofactor is selected from the group consisting of Complement Factor H Like Protein 1 (FHL1); Complement Factor H (CFH); Complement Receptor 1 (CR1) or a fragment thereof; and Membrane Cofactor Protein (MCP) or a fragment thereof.

In some embodiments, the Complement Factor I (CFI) cofactor is Complement Factor H (CFH). In some embodiments, the Complement Factor I (CFI) cofactor is Complement Receptor 1 (CR1) or a fragment thereof. In some embodiments, the Complement Factor I (CFI) cofactor is Membrane Cofactor Protein (MCP) or a fragment thereof.

In preferred embodiments, the Complement Factor I (CFI) cofactor is Complement Factor H Like Protein 1 (FHL1).

Complement Factor H (CFH)

Complement Factor H (Factor H, CFH) is a complement control protein.

Complement Factor H is a large (155 kDa), soluble glycoprotein that is present in human plasma at a typical concentration of 200-300 μg/mL (Hakobyan et al. (2008) 49 (5): 1983-90). The principal function of Complement Factor H is to regulate the alternative pathway of the complement system.

Complement Factor H provides cofactor activity for the Complement Factor I-mediated cleavage of C3b. Complement Factor H also increases the rate of dissociation of the C3bBb complex (C3 convertase) and the (C3b) NBb complex (C5 convertase) and thereby reduces the activity of the alternative complement pathway.

Complement Factor H is made up of 20 complement control protein (CCP) modules (also referred to as Short Consensus Repeats or sushi domains) connected to one another by short linkers (of between three and eight amino acid residues) and arranged in an extended head to tail fashion. Each of the CCP modules consists of around 60 amino acids with four cysteine residues disulfide bonded in a 1-3 2-4 arrangement, and a hydrophobic core built around an almost invariant tryptophan residue. The CCP modules are numbered from 1-20 (from the N-terminus of the protein). CCPs 1-4 and CCPs 19-20 engage with C3b while CCPs 6-8 and CCPs 19-20 bind to GAGs and sialic acid (Schmidt et al. (2008) Journal of Immunology 181: 2610-2619).

It has been shown that gene therapy using Complement Factor H can ameliorate induced AMD-like pathology in mice (Cashman et al. (2015) J. Gene Med. 17: 229-243). Mice were co-injected subretinally with: (i) an adenoviral vector expressing complement component C3, which had previously been shown to recapitulate many pathological features of human AMD; and (ii) an adenoviral vector expressing Complement Factor H. Relative to control animals receiving GFP instead of Complement Factor H, the Complement Factor H-transduced mice showed 91% reduction in endothelial cell proliferation and 69% attenuation of RPE atrophy. Electroretinography showed improved retinal function in mice receiving Complement Factor H, and immunocytochemistry of rhodopsin and RPE65 was consistent with the rescue of photoreceptors and RPE in such animals.

In some embodiments, a Complement Factor H polypeptide or a fragment or derivative thereof is capable of acting as a cofactor for the Complement Factor I-mediated cleavage of C3b. In some embodiments, a Complement Factor H polypeptide or a fragment or derivative thereof is capable of increasing the rate of dissociation of C3 convertase and C5 convertase.

In preferred embodiments, a Complement Factor H polypeptide or a fragment or derivative thereof is capable of acting as a cofactor for the Complement Factor I-mediated cleavage of C3b and increasing the rate of dissociation of C3 convertase and C5 convertase.

In some embodiments, the Complement Factor H is human Complement Factor H.

An example human Complement Factor H protein is the human Complement Factor H protein having the UniProtKB accession number P08603. This exemplified sequence is 1231 amino acids in length (disclosed as SEQ ID NO: 3) of which amino acids 1 to 18 form a signal sequence.

In some embodiments, the amino acid sequence of Complement Factor H is SEQ ID NO: 3. In other embodiments, the amino acid sequence of Complement Factor H is positions 19 to 1231 of SEQ ID NO: 3.

```
                                              (SEQ ID NO: 3)
MRLLAKIICLMLWAICVAEDCNELPPRRNTEILTGSWSDQTYPEGTQAI

YKCRPGYRSLGNVIMVCRKGEWVALNPLRKCQKRPCGHPGDTPFGIFTL

TGGNVFEYGVKAVYTCNEGYQLLGEINYRECDTDGWINDIPICEVVKCL

PVTAPENGKIVSSAMEPDREYHFGQAVRFVCNSGYKIEGDEEMHCSDDG

FWSKEKPKCVEISCKSPDVINGSPISQKIIYKENERFQYKCNMGYEYSE

RGDAVCTESGWRPLPSCEEKSCDNPYIPNGDYSPLRIKHRTGDEITYQC

RNGFYPATRGNTAKCISTGWIPAPRCTLKPCDYPDIKHGGLYHENMRRP

YFPVAVGKYYSYYCDEHFETPSGSYWDHIHCTQDGWSPAVPCLRKCYFP

YLENGYNQNYGRKFVQGKSIDVACHPGYALPKAQTTVTCMENGWSPTPR

CIRVKTCSKSSIDIENGFISESQYTYALKEKAKYQCKLGYVTADGETSG

SITCGKDGWSAQPTCIKSCDIPVFMNARTKNDFTWFKLNDILDYECHDG

YESNIGSTIGSIVCGYNGWSDLPICYERECELPKIDVHLVPDRKKDQYK

VGEVLKFSCKPGFTIVGPNSVQCYHFGLSPDLPICKEQVQSCGPPPELL

NGNVKEKTKEEYGHSEVVEYYCNPRFLMKGPNKIQCVDGEWTTLPVCIV

EESTCGDIPELEHGWAQLSSPPYYYGDSVEFNCSESFTMIGHRSITCIH

GVWTQLPQCVAIDKLKKCKSSNLIILEEHLKNKKEFDHNSNIRYRCRGK

EGWIHTVCINGRWDPEVNCSMAQIQLCPPPPQIPNSHNMITTLNYRDGE

KVSVLCQENYLIQEGEEITCKDGRWQSIPLCVEKIPCSQPPQIEHGTIN

SSRSSQESYAHGTKLSYTCEGGFRISEENETTCYMGKWSSPPQCEGLPC

KSPPEISHGVVAHMSDSYQYGEEVTYKCFEGFGIDGPAIAKCLGEKWSH

PPSCIKTDCLSLPSFENAIPMGEKKDVYKAGEQVTYTCATYYKMDGASN

VTCINSRWTGRPTCRDTSCVNPPTVQNAYIVSRQMSKYPSGERVRYQCR

SPYEMFGDEEVMCLNGNWTEPPQCKDSTGKCGPPPPIDNGDITSFPLSV

YAPASSVEYQCQNLYQLEGNKRITCRNGQWSEPPKCLHPCVISREIMEN

YNIALRWTAKQKLYSRTGESVEFVCKRGYRLSSRSHTLRTTCWDGKLEY

PTCAKR
```

An example nucleotide sequence encoding Complement Factor H is the nucleotide sequence having the NCBI Accession No. NM_000186.

In some embodiments, the nucleotide sequence encoding Complement Factor H is SEQ ID NO: 4.

```
                                              (SEQ ID NO: 4)
ATGAGACTTCTAGCAAAGATTATTTGCCTTATGTTATGGGCTATTTGTG

TAGCAGAAGATTGCAATGAACTTCCTCCAAGAAGAAATACAGAAATTCT

GACAGGTTCCTGGTCTGACCAAACATATCCAGAAGGCACCCAGGCTATC

TATAAATGCCGCCCTGGATATAGATCTCTTGGAAATGTAATAATGGTAT

GCAGGAAGGGAGAATGGGTTGCTCTTAATCCATTAAGGAAATGTCAGAA

AAGGCCCTGTGGACATCCTGGAGATACTCCTTTTGGTACTTTTACCCTT

ACAGGAGGAAATGTGTTTGAATATGGTGTAAAAGCTGTGTATACATGTA

ATGAGGGGTATCAATTGCTAGGTGAGATTAATTACCGTGAATGTGACAC
```

-continued

```
AGATGGATGGACCAATGATATTCCTATATGTGAAGTTGTGAAGTGTTTA
CCAGTGACAGCACCAGAGAATGGAAAAATTGTCAGTAGTGCAATGGAAC
CAGATCGGGAATACCATTTTGGACAAGCAGTACGGTTTGTATGTAACTC
AGGCTACAAGATTGAAGGAGATGAAGAAATGCATTGTTCAGACGATGGT
TTTTGGAGTAAAGAGAAACCAAAGTGTGTGGAAATTTCATGCAAATCCC
CAGATGTTATAAATGGATCTCCTATATCTCAGAAGATTATTTATAAGGA
GAATGAACGATTTCAATATAAATGTAACATGGGTTATGAATACAGTGAA
AGAGGAGATGCTGTATGCACTGAATCTGGATGGCGTCCGTTGCCTTCAT
GTGAAGAAAAATCATGTGATAATCCTTATATTCCAAATGGTGACTACTC
ACCTTTAAGGATTAAACACAGAACTGGAGATGAAATCACGTACCAGTGT
AGAAATGGTTTTTATCCTGCAACCCGGGGAAATACAGCAAAATGCACAA
GTACTGGCTGGATACCTGCTCCGAGATGTACCTTGAAACCTTGTGATTA
TCCAGACATTAAACATGGAGGTCTATATCATGAGAATATGCGTAGACCA
TACTTTCCAGTAGCTGTAGGAAAATATTACTCCTATTACTGTGATGAAC
ATTTTGAGACTCCGTCAGGAAGTTACTGGGATCACATTCATTGCACACA
AGATGGATGGTCGCCAGCAGTACCATGCCTCAGAAAATGTTATTTTCCT
TATTTGGAAAATGGATATAATCAAAATCATGGAAGAAAGTTTGTACAGG
GTAAATCTATAGACGTTGCCTGCCATCCTGGCTACGCTCTTCCAAAAGC
GCAGACCACAGTTACATGTATGGAGAATGGCTGGTCTCCTACTCCCAGA
TGCATCCGTGTCAAAACATGTTCCAAATCAAGTATAGATATTGAGAATG
GGTTTATTTCTGAATCTCAGTATACATATGCCTTAAAAGAAAAAGCGAA
ATATCAATGCAAACTAGGATATGTAACAGCAGATGGTGAAACATCAGGA
TCAATTACATGTGGGAAAGATGGATGGTCAGCTCAACCCACGTGCATTA
AATCTTGTGATATCCCAGTATTTATGAATGCCAGAACTAAAAATGACTT
ACATGGTTTAAGCTGAATGACACATTGGACTATGAATGCCATGATGGTT
ATGAAAGCAATACTGGAAGCACCACTGGTTCCATAGTGTGTGGTTACAA
TGGTTGGTCTGATTTACCCATATGTTATGAAAGAGAATGCGAACTTCCT
AAAATAGATGTACACTTAGTTCCTGATCGCAAGAAAGACCAGTATAAAG
TTGGAGAGGTGTTGAAATTCTCCTGCAAACCAGGATTTACAATAGTTGG
ACCTAATTCCGTTCAGTGCTACCACTTTGGATTGTCTCCTGACCTCCCA
ATATGTAAAGAGCAAGTACAATCATGTGGTCCACCTCCTGAACTCCTCA
ATGGGAATGTTAAGGAAAAAACGAAAGAAGAATATGGACACAGTGAAGT
GGTGGAATATTATTGCAATCCTAGATTTCTAATGAAGGGACCTAATAAA
ATTCAATGTGTTGATGGAGAGTGGACAACTTTACCAGTGTGTATTGTGG
AGGAGAGTACCTGTGGAGATATACCTGAACTTGAACATGGCTGGGCCCA
GCTTTCTTCCCCTCCTTATTACTATGGAGATTCAGTGGAATTCAATTGC
TCAGAATCATTTACAATGATTGGACACAGATCAATTACGTGTATTCATG
GAGTATGGACCCAACTTCCCCAGTGTGTGGCAATAGATAAACTTAAGAA
GTGCAAATCATCAAATTTAATTATACTTGAGGAACATTTAAAAAACAAG
AAGGAATTCGATCATAATTCTAACATAAGGTACAGATGTAGAGGAAAAG
AAGGATGGATACACACAGTCTGCATAAATGGAAGATGGGATCCAGAAGT
GAACTGCTCAATGGCACAAATACAATTATGCCCACCTCCACCTCAGATT
CCCAATTCTCACAATATGACAACCACACTGAATTATCGGGATGGAGAAA
AAGTATCTGTTCTTTGCCAAGAAAATTATCTAATTCAGGAAGGAGAAGA
AATTACATGCAAAGATGGAAGATGGCAGTCAATACCACTCTGTGTTGAA
AAAATTCCATGTTCACAACCACCTCAGATAGAACACGGAACCATTAATT
CATCCAGGTCTTCACAAGAAAGTTATGCACATGGGACTAAATTGAGTTA
TACTTGTGAGGGTGGTTTCAGGATATCTGAAGAAAATGAAACAACATGC
TACATGGGAAAATGGAGTTCTCCACCTCAGTGTGAAGGCCTTCCTTGTA
AATCTCCACCTGAGATTTCTCATGGTGTTGTAGCTCACATGTCAGACAG
TTATCAGTATGGAGAAGAAGTTACGTACAAATGTTTTGAAGGTTTTGGA
ATTGATGGGCCTGCAATTGCAAAATGCTTAGGAGAAAAATGGTCTCACC
CTCCATCATGCATAAAAACAGATTGTCTCAGTTTACCTAGCTTTGAAAA
TGCCATACCCATGGGAGAGAAGAAGGATGTGTATAAGGCGGGTGAGCAA
GTGACTTACACTTGTGCAACATATTACAAAATGGATGGAGCCAGTAATG
TAACATGCATTAATAGCAGATGGACAGGAAGGCCAACATGCAGAGACAC
CTCCTGTGTGAATCCGCCCACAGTACAAAATGCTTATATAGTGTCGAGA
CAGATGAGTAAATATCCATCTGGTGAGAGAGTACGTTATCAATGTAGGA
GCCCTTATGAAATGTTTGGGGATGAAGAAGTGATGTGTTTAAATGGAAA
CTGGACGGAACCACCTCAATGCAAAGATTCTACAGGAAAATGTGGGCCC
CCTCCACCTATTGACAATGGGGACATTACTTCATTCCCGTTGTCAGTAT
ATGCTCCAGCTTCATCAGTTGAGTACCAATGCCAGAACTTGTATCAACT
TGAGGGTAACAAGCGAATAACATGTAGAAATGGACAATGGTCAGAACCA
CCAAAATGCTTACATCCGTGTGTAATATCCCGAGAAATTATGGAAAATT
ATAACATAGCATTAAGGTGGACAGCCAAACAGAAGCTTTATTCGAGAAC
AGGTGAATCAGTTGAATTTGTGTGTAAACGGGGATATCGTCTTTCATCA
CGTTCTCACACATTGCGAACAACATGTTGGGATGGGAAACTGGAGTATC
CAACTTGTGCAAAAAGATAG
```

In some embodiments, the nucleotide sequence encoding Complement Factor H has at least 75%, 80%, 85%, 90%, 95%, 96%, 97%, 98% or 99% identity to SEQ ID NO: 4. Preferably, wherein the protein encoded by the nucleotide sequence substantially retains a functional activity of the protein represented by SEQ ID NO: 3.

In other embodiments, the nucleotide sequence encoding Complement Factor H is SEQ ID NO: 4.

In other embodiments, the nucleotide sequence encoding Complement Factor H has at least 75%, 80%, 85% 90%, 95%, 96%, 97%, 98% or 99% identity to positions 55 to 3696 of SEQ ID NO: 4. Preferably, wherein the protein encoded by the nucleotide sequence substantially retains a functional activity of the protein represented by SEQ ID NO: 3.

In other embodiments, the nucleotide sequence encoding Complement Factor H is positions 55 to 3696 of SEQ ID NO: 4.

In other embodiments, the nucleotide sequence encoding Complement Factor H encodes an amino acid sequence that has at least 75%, 80%, 85% 90%, 95%, 96%, 97%, 98% or 99% identity to SEQ ID NO: 3. Preferably, wherein the amino acid sequence substantially retains a functional activity of the protein represented by SEQ ID NO: 3.

In other embodiments, the nucleotide sequence encoding Complement Factor H encodes the amino acid sequence SEQ ID NO: 3.

In other embodiment, the nucleotide sequence encoding Complement Factor H encodes an amino acid sequence that has at least 75%, 80%, 85%, 90%, 95%, 96%, 97%, 98%, 99% identity to positions 19 to 1231 of SEQ ID NO: 3. Preferably, wherein the amino acid sequence substantially retains a functional activity of the protein represented by SEQ ID NO: 3.

In other embodiments, the nucleotide sequence encoding Complement Factor H encodes the amino acid sequence of positions 19 to 1231 of SEQ ID NO: 3.

Complement Factor H-Like Protein 1 (FHL1)

Complement Factor H-like Protein 1 (FHL1) is a splice variant of Complement Factor H that contains the first 7 CCPs of Complement Factor H followed by a four amino acid carboxy-terminal tail (Clark, S. J. et al. (2015) J Clin Med 4: 18-31).

In some embodiments, the FHL1 is human FHL1.

In some embodiments, the amino acid sequence of FHL1 is SEQ ID NO: 11.

(SEQ ID NO: 11)

```
MRLLAKIICLMLWAICVAEDCNELPPRRNTEILTGSWSDQTYPEGTQAI
YKCRPGYRSLGNIIMVCRKGEWVALNPLRKCQKRPCGHPGDTPFGTFTL
TGGNVFEYGVKAVYTCNEGYQLLGEINYRECDIDGWINDIPICEVVKCL
PVTAPENGKIVSSAMEPDREYHFGQAVRFVCNSGYKIEGDEEMHCSDDG
FWSKEKPKCVEISCKSPDVINGSPISQKIIYKENERFQYKCNMGYEYSE
RGDAVCTESGWRPLPSCEEKSCDNPYIPNGDYSPLRIKHRTGDEITYQC
RNGFYPATRGNTAKCISTGWIPAPRCTLKPCDYPDIKHGGLYHENMRRP
YFPVAVGKYYSYYCDEHFETPSGSYWDHIHCTQDGWSPAVPCLRKCYFP
YLENGYNQNYGRKFVQGKSIDVACHPGYALPKAQTTVTCMENGWSPTPR
CIRVSFTL
```

An example nucleotide sequence encoding FHL1 is:

(SEQ ID NO: 16)

```
ATGAGACTTCTAGCAAAGATTATTTGCCTTATGTTATGGGCTATTTGTG
TAGCAGAAGATTGCAATGAACTTCCTCCAAGAAGAAATACAGAAATTCT
GACAGGTTCCTGGTCTGACCAAACATATCCAGAAGGCACCCAGGCTATC
TATAAATGCCGCCCTGGATATAGATCTCTTGGAAATATAATAATGGTAT
GCAGGAAGGGAGAATGGGTTGCTCTTAATCCATTAAGGAAATGTCAGAA
AAGGCCCTGTGGACATCCTGGAGATACTCCTTTTGGTACTTTTACCCTT
ACAGGAGGAAATGTGTTTGAATATGGTGTAAAAGCTGTGTATACATGTA
ATGAGGGGTATCAATTGCTAGGTGAGATTAATTACCGTGAATGTGACAC
AGATGGATGGACCAATGATATTCCTATATGTGAAGTTGTGAAGTGTTTA
CCAGTGACAGCACCAGAGAATGGAAAAATTGTCAGTAGTGCAATGGAAC
CAGATCGGGAATACCATTTTGGACAAGCAGTACGGTTTGTATGTAACTC
AGGCTACAAGATTGAAGGAGATGAAGAAATGCATTGTTCAGACGATGGT
```

-continued

```
TTTTGGAGTAAAGAGAAACCAAAGTGTGTGGAAATTTCATGCAAATCCC
CAGATGTTATAAATGGATCTCCTATATCTCAGAAGATTATTTATAAGGA
GAATGAACGATTTCAATATAAATGTAACATGGGTTATGAATACAGTGAA
AGAGGAGATGCTGTATGCACTGAATCTGGATGGCGTCCGTTGCCTTCAT
GTGAAGAAAAATCATGTGATAATCCTTATATTCCAAATGGTGACTACTC
ACCTTTAAGGATTAAACACAGAACTGGAGATGAAATCACGTACCAGTGT
AGAAATGGTTTTTATCCTGCAACCCGGGGAAATACAGCaAAATGCACAA
GTACTGGCTGGATACCTGCTCCGAGATGTACCTTGAAACCTTGTGATTA
TCCAGACATTAAACATGGAGGTCTATATCATGAGAATATGCGTAGACCA
TACTTTCCAGTAGCTGTAGGAAAATATTACTCCTATTACTGTGATGAAC
ATTTTGAGACTCCGTCAGGAAGTTACTGGGATCACATTCATTGCACACA
AGATGGATGGTCGCCAGCAGTACCATGCCTCAGAAAATGTTATTTTCCT
TATTTGGAAAATGGATATAATCAAAATTATGGAAGAAAGTTTGTACAGG
GTAAATCTATAGACGTTGCCTGCCATCCTGGCTACGCTCTTCCAAAAGC
GCAGACCACAGTTACATGTATGGAGAATGGCTGGTCTCCTACTCCCAGA
TGCATCCGTGTCAGCTTTACCCTCTGA
```

The nucleotide sequences of FHL1 used in the invention are preferably codon optimised.

A preferred nucleotide sequence encoding FHL1 is SEQ ID NO: 12.

(SEQ ID NO: 12)

```
ATGCGCCTCCTGGCCAAGATCATCTGCCTCATGCTGTGGGCCATCTGCG
TGGCTGAGGACTGCAATGAGCTGCCGCCCAGGAGGAACACAGAGATCCT
GACAGGGAGCTGGTCTGACCAGACCTACCCTGAGGGCACCCAGGCGATC
TACAAGTGCCGGCCGGGCTACAGGAGCCTGGGGAACATCATCATGGTGT
GTAGAAAGGGCGAATGGGTGGCCCTCAACCCCCTGAGGAAGTGCCAGAA
GCGGCCCTGTGGCCACCCCGGGGACACACCCTTCGGGACCTTCACCCTG
ACCGGCGGCAATGTGTTTGAGTACGGCGTGAAGGCTGTCTACACATGCA
ACGAGGGGTACCAGCTGCTGGGCGAGATTAACTACCGGGAGTGTGACAC
CGATGGGTGGACCAACGACATTCCCATCTGTGAGGTGGTCAAGTGTCTC
CCCGTGACAGCCCCAGAAAATGGCAAAATCGTGAGCAGCGCCATGGAGC
CTGACCGCGAATATCACTTTGGGCAGGCCGTGAGGTTTGTGTGCAACTC
GGGCTACAAAATTGAAGGTGATGAGGAGATGCACTGCAGCGATGATGGC
TTCTGGTCCAAGGAGAAGCCCAAATGTGTGGAGATCTCCTGCAAGTCTC
CCGACGTGATCAACGGCAGCCCAATCAGCCAGAAGATTATTTACAAAGA
GAACGAGCGCTTCCAGTACAAGTGTAACATGGGCTATGAGTATTCAGAG
AGGGGAGATGCCGTCTGCACTGAGAGCGGCTGGAGACCACTGCCTAGCT
GCGAGGAAAAGAGTTGTGACAACCCTTACATCCCAAATGGCGACTACTC
CCCTCTGCGGATCAAACACCGGACCGGGGATGAAATCACCTATCAGTGC
CGCAATGGATTCTACCCGGCCACCCGCGGCAACACCGCCAAATGCACCA
GCACAGGCTGGATCCCCGCCCCCCGCTGTACGCTGAAGCCTTGCGACTA
```

-continued

```
TCCAGACATCAAGCACGGAGGCCTGTACCACGAAAACATGCGGCGGCCT
TATTTCCCTGTGGCAGTGGGGAAGTACTACAGCTACTACTGCGACGAGC
ACTTCGAGACCCCCTCTGGCTCCTACTGGGACCACATCCACTGCACACA
GGACGGCTGGTCTCCAGCTGTGCCCTGCCTGAGGAAATGCTACTTCCCC
TACCTGGAGAACGGATACAACCAGAACTATGGCCGCAAGTTCGTGCAGG
GCAAGAGCATCGATGTGGCCTGCCACCCTGGCTACGCCCTGCCCAAGGC
CCAGACAACTGTGACCTGCATGGAGAATGGTTGGAGCCCCACCCCGCGC
TGCATCCGGGTGTCCTTCACGCTCTGA
```

In some embodiments, the nucleotide sequence encoding FHL1 has at least 75%, 80%, 85%, 90%, 91%, 92%, 93%, 94%, 95%, 96%, 97%, 98% or 99% identity to SEQ ID NO: 12 or 16, preferably SEQ ID NO: 12. Preferably, the protein encoded by the nucleotide sequence substantially retains a functional activity of the protein represented by SEQ ID NO: 11.

In other embodiments, the nucleotide sequence encoding FHL1 is SEQ ID NO: 12 or 16, preferably SEQ ID NO: 12.

Complement Receptor 1 (CR1)

Complement Receptor 1 (CR1), also known as CD35, is a type I membrane-bound glycoprotein belonging to the regulators of complement activity (RCA) family. CR1 may be found on the plasma membrane of erythrocytes, eosinophils, monocytes, macrophages, B-lymphocytes, a subpopulation of CD4+ T cells, dendritic cells, Langerhan cells in the skin and glomerular podocytes.

CR1 is an ~200 kDa, single-chain glycoprotein, the extracellular portion of which comprises 30 complement-control-protein repeats (CCPs) or short consensus repeats. A non-membrane bound soluble form of CR1 (sCR1) is found in plasma. It may be generated by release from leukocytes by cleavage of the surface form of CR1. The structure of CR1 and sCR1 is described, for example, in Liu, D. et al. (2009) Immunopharmacology and Immunotoxicology 31: 524-535.

In some embodiments, the CR1 or fragment thereof is human CR1 or a fragment thereof.

An example CR1 sequence is:

```
                                          (SEQ ID NO: 24)
MGASSPRSPEPVGPPAPGLPFCCGGSLLAVVVLLALPVAWGQCNAPEWL
PFARPTNLTDEFEFPIGTYLNYECRPGYSGRPFSIICLKNSVWTGAKDR
CRRKSCRNPPDPVNGMVHVIKGIQFGSQIKYSCTKGYRLIGSSSATCII
SGDTVIWDNETPICDRIPCGLPPTITNGDFISTNRENFHYGSVVTYRCN
PGSGGRKVFELVGEPSIYCTSNDDQVGIWSGPAPQCIIPNKCTPPNVEN
GILVSDNRSLFSLNEVVEFRCQPGFVMKGPRRVKCQALNKWEPELPSCS
RVCQPPPDVLHAERTQRDKDNFSPGQEVFYSCEPGYDLRGAASMRCTPQ
GDWSPAAPTCEVKSCDDFMGQLLNGRVLFPVNLQLGAKVDFVCDEGFQL
KGSSASYCVLAGMESLWNSSVPVCEQIFCPSPPVIPNGRHTGKPLEVFP
FGKTVNYTCDPHPDRGTSFDLIGESTIRCTSDPQGNGVWSSPAPRCGIL
GHCQAPDHFLFAKLKTQTNASDFPIGTSLKYECRPEYYGRPFSITCLDN
LVWSSPKDVCKRKSCKTPPDPVNGMVHVITDIQVGSRINYSCTTGHRLI
GHSSAECILSGNAAHWSTKPPICQRIPCGLPPTIANGDFISTNRENFHY
```

-continued

```
GSVVTYRCNPGSGGRKVFELVGEPSIYCTSNDDQVGIWSGPAPQCIIPN
KCTPPNVENGILVSDNRSLFSLNEVVEFRCQPGFVMKGPRRVKCQALNK
WEPELPSCSRVCQPPPDVLHAERTQRDKDNFSPGQEVFYSCEPGYDLRG
AASMRCTPQGDWSPAAPTCEVKSCDDFMGQLLNGRVLFPVNLQLGAKVD
FVCDEGFQLKGSSASYCVLAGMESLWNSSVPVCEQIFCPSPPVIPNGRH
TGKPLEVFPFGKAVNYTCDPHPDRGTSFDLIGESTIRCTSDPQGNGVWS
SPAPRCGILGHCQAPDHFLFAKLKTQTNASDFPIGTSLKYECRPEYYGR
PFSITCLDNLVWSSPKDVCKRKSCKTPPDPVNGMVHVITDIQVGSRINY
SCTTGHRLIGHSSAECILSGNTAHWSTKPPICQRIPCGLPPTIANGDFI
STNRENFHYGSVVTYRCNLGSRGRKVFELVGEPSIYCTSNDDQVGIWSG
PAPQCIIPNKCTPPNVENGILVSDNRSLFSLNEVVEFRCQPGFVMKGPR
RVKCQALNKWEPELPSCSRVCQPPPEILHGEHTPSHQDNFSPGQEVFYS
CEPGYDLRGAASLHCTPQGDWSPEAPRCAVKSCDDFLGQLPHGRVLFPL
NLQLGAKVSFVCDEGFRLKGSSVSHCVLVGMRSLWNNSVPVCEHIFCPN
PPAILNGRHIGTPSGDIPYGKEISYTCDPHPDRGMTENLIGESTIRCTS
DPHGNGVWSSPAPRCELSVRAGHCKTPEQFPFASPTIPINDFEFPVGTS
LNYECRPGYFGKMFSISCLENLVWSSVEDNCRRKSCGPPPEPENGMVHI
NTDTQFGSTVNYSCNEGERLIGSPSTTCLVSGNNVTWDKKAPICEIISC
EPPPTISNGDFYSNNRISFHNGTVVTYQCHTGPDGEQLFELVGERSIYC
TSKDDQVGVWSSPPPRCISTNKCTAPEVENAIRVPGNRSFFTLTEIIRF
RCQPGFVMVGSHTVQCQINGRWGPKLPHCSRVCQPPPEILHGEHTLSHQ
DNFSPGQEVFYSCEPSYDLRGAASLHCTPQGDWSPEAPRCTVKSCDDFL
GQLPHGRVLLPLNLQLGAKVSFVCDEGFRLKGRSASHCVLAGMKALWNS
SVPVCEQIFCPNPPAILNGRHTGTPFGDIPYGKEISYACDTHPDRGMTF
NLIGESSIRCTSDPQGNGVWSSPAPRCELSVPAACPHPPKIQNGHYIGG
HVSLYLPGMTISYICDPGYLLVGKGFIFCTDQGIWSQLDHYCKEVNCSF
PLFMNGISKELEMKKVYHYGDYVTLKCEDGYTLEGSPWSQCQADDRWDP
PLAKCTSRTHDALIVGILSGTIFFILLIIFLSWIILKHRKGNNAHENPK
EVAIHLHSQGGSSVHPRTLQTNEENSRVLP
```

An example nucleotide sequence encoding CR1 is:

```
                                          (SEQ ID NO: 25)
ATGGGGGCCTCTTCTCCAAGAAGCCCGGAGCCTGTCGGGCCGCCGGCGC
CCGGTCTCCCCTTCTGCTGCGGAGGATCCCTGCTGGCGGTTGTGGTGCT
GCTTGCGCTGCCGGTGGCCTGGGGTCAATGCAATGCCCCAGAATGGCTT
CCATTTGCCAGGCCTACCAACCTAACTGATGAATTTGAGTTTCCCATTG
GGACATATCTGAACTATGAATGCCGCCCTGGTTATTCCGGAAGACCGTT
TTCTATCATCTGCCTAAAAAACTCAGTCTGGACTGGTGCTAAGGACAGG
TGCAGACGTAAATCATGTCGTAATCCTCCAGATCCTGTGAATGGCATGG
TGCATGTGATCAAAGGCATCCAGTTCGGATCCCAAATTAAATATTCTTG
TACTAAAGGATACCGACTCATTGGTTCCTCGTCTGCCACATGCATCATC
```

TCAGGTGATACTGTCATTTGGGATAATGAAACACCTATTTGTGACAGAA
TTCCTTGTGGGCTACCCCCCACCATCACCAATGGAGATTTCATTAGCAC
CAACAGAGAGAATTTTCACTATGGATCAGTGGTGACCTACCGCTGCAAT
CCTGGAAGCGGAGGGAGAAAGGTGTTTGAGCTTGTGGGTGAGCCCTCCA
TATACTGCACCAGCAATGACGATCAAGTGGGCATCTGGAGCGGCCCCGC
CCCTCAGTGCATTATACCTAACAAATGCACGCCTCCAAATGTGGAAAAT
GGAATATTGGTATCTGACAACAGAAGCTTATTTTCCTTAAATGAAGTTG
TGGAGTTTAGGTGTCAGCCTGGCTTTGTCATGAAAGGACCCCGCCGTGT
GAAGTGCCAGGCCCTGAACAAATGGGAGCCGGAGCTACCAAGCTGCTCC
AGGGTATGTCAGCCACCTCCAGATGTCCTGCATGCTGAGCGTACCCAAA
GGGACAAGGACAACTTTTCACCTGGGCAGGAAGTGTTCTACAGCTGTGA
GCCCGGCTACGACCTCAGAGGGGCTGCGTCTATGCGCTGCACACCCCAG
GGAGACTGGAGCCCTGCAGCCCCCACATGTGAAGTGAAATCCTGTGATG
ACTTCATGGGCCAACTTCTTAATGGCCGTGTGCTATTTCCAGTAAATCT
CCAGCTTGGAGCAAAAGTGGATTTTGTTTGTGATGAAGGATTTCAATTA
AAAGGCAGCTCTGCTAGTTACTGTGTCTTGGCTGGAATGGAAAGCCTTT
GGAATAGCAGTGTTCCAGTGTGTGAACAAATCTTTTGTCCAAGTCCTCC
AGTTATTCCTAATGGGAGACACACAGGAAAACCTCTGGAAGTCTTTCCC
TTTGGGAAAACAGTAAATTACACATGCGACCCCCACCCAGACAGAGGGA
CGAGCTTCGACCTCATTGGAGAGAGCACCATCCGCTGCACAAGTGACCC
TCAAGGGAATGGGGTTTGGAGCAGCCCTGCCCCTCGCTGTGGAATTCTG
GGTCACTGTCAAGCCCCAGATCATTTTCTGTTTGCCAAGTTGAAAACCC
AAACCAATGCATCTGACTTTCCCATTGGGACATCTTTAAAGTACGAATG
CCGTCCTGAGTACTACGGGAGGCCATTCTCTATCACATGTCTAGATAAC
CTGGTCTGGTCAAGTCCCAAAGATGTCTGTAAACGTAAATCATGTAAAA
CTCCTCCAGATCCAGTGAATGGCATGGTGCATGTGATCACAGACATCCA
GGTTGGATCCAGAATCAACTATTCTTGTACTACAGGGCACCGACTCATT
GGTCACTCATCTGCTGAATGTATCCTCTCGGGCAATGCTGCCCATTGGA
GCACGAAGCCGCCAATTTGTCAACGAATTCCTTGTGGGCTACCCCCCAC
CATCGCCAATGGAGATTTCATTAGCACCAACAGAGAGAATTTTCACTAT
GGATCAGTGGTGACCTACCGCTGCAATCCTGGAAGCGGAGGGAGAAAGG
TGTTTGAGCTTGTGGGTGAGCCCTCCATATACTGCACCAGCAATGACGA
TCAAGTGGGCATCTGGAGCGGCCCGGCCCCTCAGTGCATTATACCTAAC
AAATGCACGCCTCCAAATGTGGAAAATGGAATATTGGTATCTGACAACA
GAAGCTTATTTTCCTTAAATGAAGTTGTGGAGTTTAGGTGTCAGCCTGG
CTTTGTCATGAAAGGACCCCGCCGTGTGAAGTGCCAGGCCCTGAACAAA
TGGGAGCCGGAGCTACCAAGCTGCTCCAGGGTATGTCAGCCACCTCCAG
ATGTCCTGCATGCTGAGCGTACCCAAAGGGACAAGGACAACTTTTCACC
CGGGCAGGAAGTGTTCTACAGCTGTGAGCCCGGCTATGACCTCAGAGGG
GCTGCGTCTATGCGCTGCACACCCCAGGGAGACTGGAGCCCTGCAGCCC

CCACATGTGAAGTGAAATCCTGTGATGACTTCATGGGCCAACTTCTTAA
TGGCCGTGTGCTATTTCCAGTAAATCTCCAGCTTGGAGCAAAAGTGGAT
TTTGTTTGTGATGAAGGATTTCAATTAAAAGGCAGCTCTGCTAGTTATT
GTGTCTTGGCTGGAATGGAAAGCCTTTGGAATAGCAGTGTTCCAGTGTG
TGAACAAATCTTTTGTCCAAGTCCTCCAGTTATTCCTAATGGGAGACAC
ACAGGAAAACCTCTGGAAGTCTTTCCCTTTGGAAAAGCAGTAAATTACA
CATGCGACCCCCACCCAGACAGAGGGACGAGCTTCGACCTCATTGGAGA
GAGCACCATCCGCTGCACAAGTGACCCTCAAGGGAATGGGGTTTGGAGC
AGCCCTGCCCCTCGCTGTGGAATTCTGGGTCACTGTCAAGCCCCAGATC
ATTTTCTGTTTGCCAAGTTGAAAACCCAAACCAATGCATCTGACTTTCC
CATTGGGACATCTTTAAAGTACGAATGCCGTCCTGAGTACTACGGGAGG
CCATTCTCTATCACATGTCTAGATAACCTGGTCTGGTCAAGTCCCAAAG
ATGTCTGTAAACGTAAATCATGTAAAACTCCTCCAGATCCAGTGAATGG
CATGGTGCATGTGATCACAGACATCCAGGTTGGATCCAGAATCAACTAT
TCTTGTACTACAGGGCACCGACTCATTGGTCACTCATCTGCTGAATGTA
TCCTCTCAGGCAATACTGCCCATTGGAGCACGAAGCCGCCAATTTGTCA
ACGAATTCCTTGTGGGCTACCCCCAACCATCGCCAATGGAGATTTCATT
AGCACCAACAGAGAGAATTTTCACTATGGATCAGTGGTGACCTACCGCT
GCAATCTTGGAAGCAGAGGGAGAAAGGTGTTTGAGCTTGTGGGTGAGCC
CTCCATATACTGCACCAGCAATGACGATCAAGTGGGCATCTGGAGCGGC
CCCGCCCCTCAGTGCATTATACCTAACAAATGCACGCCTCCAAATGTGG
AAAATGGAATATTGGTATCTGACAACAGAAGCTTATTTTCCTTAAATGA
AGTTGTGGAGTTTAGGTGTCAGCCTGGCTTTGTCATGAAAGGACCCCGC
CGTGTGAAGTGCCAGGCCCTGAACAAATGGGAGCCAGAGTTACCAAGCT
GCTCCAGGGTGTGTCAGCCGCCTCCAGAAATCCTGCATGGTGAGCATAC
CCCAAGCCATCAGGACAACTTTTCACCTGGGCAGGAAGTGTTCTACAGC
TGTGAGCCTGGCTATGACCTCAGAGGGGCTGCGTCTCTGCACTGCACAC
CCCAGGGAGACTGGAGCCCTGAAGCCCCGAGATGTGCAGTGAAATCCTG
TGATGACTTCTTGGGTCAACTCCCTCATGGCCGTGTGCTATTTCCACTT
AATCTCCAGCTTGGGGCAAAGGTGTCCTTTGTCTGTGATGAAGGGTTTC
GCTTAAAGGGCAGTTCCGTTAGTCATTGTGTCTTGGTTGGAATGAGAAG
CCTTTGGAATAACAGTGTTCCTGTGTGTGAACATATCTTTTGTCCAAAT
CCTCCAGCTATCCTTAATGGGAGACACACAGGAACTCCCTCTGGAGATA
TTCCCTATGGAAAAGAAATATCTTACACATGTGACCCCCACCCAGACAG
AGGGATGACCTTCAACCTCATTGGGGAGAGCACCATCCGCTGCACAAGT
GACCCTCATGGGAATGGGGTTTGGAGCAGCCCTGCCCCTCGCTGTGAAC
TTTCTGTTCGTGCTGGTCACTGTAAAACCCCAGAGCAGTTTCCATTTGC
CAGTCCTACGATCCCAATTAATGACTTTGAGTTTCCAGTCGGGACATCT
TTGAATTATGAATGCCGTCCTGGGTATTTTGGGAAAATGTTCTCTATCT
CCTGCCTAGAAAACTTGGTCTGGTCAAGTGTTGAAGACAACTGTAGACG
AAAATCATGTGGACCTCCACCAGAACCCTTCAATGGAATGGTGCATATA

-continued

```
AACACAGATACACAGTTTGGATCAACAGTTAATTATTCTTGTAATGAAG

GGTTTCGACTCATTGGTTCCCCATCTACTACTTGTCTCGTCTCAGGCAA

TAATGTCACATGGGATAAGAAGGCACCTATTTGTGAGATCATATCTTGT

GAGCCACCTCCAACCATATCCAATGGAGACTTCTACAGCAACAATAGAA

CATCTTTTCACAATGGAACGGTGGTAACTTACCAGTGCCACACTGGACC

AGATGGAGAACAGCTGTTTGAGCTTGTGGGAGAACGGTCAATATATTGC

ACCAGCAAAGATGATCAAGTTGGTGTTTGGAGCAGCCCTCCCCCTCGGT

GTATTTCTACTAATAAATGCACAGCTCCAGAAGTTGAAAATGCAATTAG

AGTACCAGGAAACAGGAGTTTCTTTACCCTCACTGAGATCATCAGATTT

AGATGTCAGCCCGGGTTTGTCATGGTAGGGTCCCACACTGTGCAGTGCC

AGACCAATGGCAGATGGGGGCCCAAGCTGCCACACTGCTCCAGGGTGTG

TCAGCCGCCTCCAGAAATCCTGCATGGTGAGCATACCCTAAGCCATCAG

GACAACTTTTCACCTGGGCAGGAAGTTGTTCTACAGCTGTGAGCCCAGC

TATGACCTCAGAGGGGCTGCGTCTCTGCACTGCACGCCCCAGGGAGACT

GGAGCCCTGAAGCCCCTAGATGTACAGTGAAATCCTGTGATGACTTCCT

GGGCCAACTCCCTCATGGCCGTGTGCTACTTCCACTTAATCTCCAGCTT

GGGGCAAAGGTGTCCTTTGTTTGCGATGAAGGGTTCCGATTAAAAGGCA

GGTCTGCTAGTCATTGTGTCTTGGCTGGAATGAAAGCCCTTTGGAATAG

CAGTGTTCCAGTGTGTGAACAAATCTTTTGTCCAAATCCTCCAGCTATC

CTTAATGGGAGACACACAGGAACTCCCTTTGGAGATATTCCCTATGGAA

AAGAAATATCTTACGCATGCGACACCCACCCAGACAGAGGGATGACCTT

CAACCTCATTGGGGAGAGCTCCATCCGCTGCACAAGTGACCCTCAAGGG

AATGGGGTTTGGAGCAGCCCTGCCCCTCGCTGTGAACTTTCTGTTCCTG

CTGCCTGCCCACATCCACCCAAGATCCAAAACGGGCATTACATTGGAGG

ACACGTATCTCTATATCTTCCTGGGATGACAATCAGCTACATTTGTGAC

CCCGGCTACCTGTTAGTGGGAAAGGGCTTCATTTTCTGTACAGACCAGG

GAATCTGGAGCCAATTGGATCATTATTGCAAAGAAGTAAATTGTAGCTT

CCCACTGTTTATGAATGGAATCTCGAAGGAGTTAGAAATGAAAAAAGTA

TATCACTATGGAGATTATGTGACTTTGAAGTGTGAAGATGGGTATACTC

TGGAAGGCAGTCCCTGGAGCCAGTGCCAGGCGGATGACAGATGGGACCC

TCCTCTGGCCAAATGTACCTCTCGTACACATGATGCTCTCATAGTTGGC

ACTTTATCTGGTACGATCTTCTTTATTTTACTCATCATTTTCCTCTCTT

GGATAATTCTAAAGCACAGAAAAGGCAATAATGCACATGAAAACCCTAA

AGAAGTGGCTATCCATTTACATTCTCAAGGAGGCAGCAGCGTTCATCCC

CGAACTCTGCAAACAAATGAAGAAAATAGCAGGGTCCTTCCTTGA
```

In some embodiments, the CR1 or fragment thereof is soluble CR1 (sCR1).

The CR1 fragment is preferably capable of acting as a cofactor for the CFI-mediated cleavage of C3b. The skilled person would be readily able to determine such CFI activity using any suitable method known in the art, for example as disclosed herein.

CR1 contains two known binding sites for C3b (see Liu, D. et al. (2009) Immunopharmacology and Immunotoxicology 31: 524-535). In preferred embodiments, the CR1 fragment comprises one or two C3b binding sites.

Preferably, the fragment of CR1 is a soluble fragment of CR1, for example generated by removing the transmembrane and cytoplasmic domains from full length CR1 and/or by selecting CR1 truncations comprising or consisting of certain CCPs.

Example CR1 fragments are known in the art (see, for example, WO2019138137). For example, the CR1 fragment may comprise or consist of CCPs 8-10 (e.g. corresponding to amino acids 491 to 684 of SEQ ID NO: 24) and/or CCPs 15-17 (e.g. corresponding to amino acids 941 to 1134 of SEQ ID NO: 24).

In some embodiments, the CR1 fragment comprises CCPs 8-10. In some embodiments, the CR1 fragment comprises CCPs 15-17. In some embodiments, the CR1 fragment comprises CCPs 8-10 and CCPs 15-17.

In other embodiments, the nucleotide sequence encoding CR1 encodes an amino acid sequence that has at least 75%, 80%, 85% 90%, 95%, 96%, 97%, 98% or 99% identity to SEQ ID NO: 24. Preferably, wherein the amino acid sequence substantially retains a functional activity of the protein represented by SEQ ID NO: 24.

In other embodiments, the nucleotide sequence encoding CR1 encodes the amino acid sequence SEQ ID NO: 24.

In other embodiments, the nucleotide sequence encoding CR1 encodes an amino acid sequence that has at least 75%, 80%, 85% 90%, 95%, 96%, 97%, 98% or 99% identity to positions 491 to 684 of SEQ ID NO: 24. Preferably, wherein the amino acid sequence substantially retains a functional activity of the protein represented by SEQ ID NO: 24.

In other embodiments, the nucleotide sequence encoding CR1 encodes the amino acid sequence positions 491 to 684 of SEQ ID NO: 24.

In other embodiments, the nucleotide sequence encoding CR1 encodes an amino acid sequence that has at least 75%, 80%, 85% 90%, 95%, 96%, 97%, 98% or 99% identity to positions 941 to 1134 of SEQ ID NO: 24. Preferably, wherein the amino acid sequence substantially retains a functional activity of the protein represented by SEQ ID NO: 24.

In other embodiments, the nucleotide sequence encoding CR1 encodes the amino acid sequence positions 941 to 1134 of SEQ ID NO: 24.

Membrane Cofactor Protein (MCP)

Membrane Cofactor Protein (MCP), also known as CD46, is a type I membrane protein that functions as a regulatory part of the complement system and acts as a cofactor for CFI.

The extracellular region of MCP contains four short consensus repeats (SCRs).

In some embodiments, the MCP or fragment thereof is human MCP or a fragment thereof.

An example MCP sequence is:

```
                                       (SEQ ID NO: 26)
MEPPGRRECPFPSWRFPGLLLAAMVLLLYSFSDACEEPPTFEAMELIGK

PKPYYEIGERVDYKCKKGYFYIPPLATHTICDRNHTWLPVSDDACYRET

CPYIRDPLNGQAVPANGTYEFGYQMHFICNEGYYLIGEEILYCELKGSV

AIWSGKPPICEKVLCTPPPKIKNGKHTFSEVEVFEYLDAVTYSCDPAPG

PDPFSLIGESTIYCGDNSVWSRAAPECKVVKCRFPVVENGKQISGFGKK

FYYKATVMFECDKGFYLDGSDTIVCDSNSTWDPPVPKCLKVLPPSSTKP
```

-continued

PALSHSVSTSSITKSPASSASGPRPTYKPPVSNYPGYPKPEEGILDSLD

VWVIAVIVIAIVVGVAVICVVPYRYLQRRKKKGTYLTDETHREVKFTSL

An example nucleotide sequence encoding MCP is:

(SEQ ID NO: 27)
ATGGAGCCTCCCGGCCGCCGCGAGTGTCCCTTTCCTTCCTGGCGCTTTC

CTGGGTTGCTTCTGGCGGCCATGGTGTTGCTGCTGTACTCCTTCTCCGA

TGCCTGTGAGGAGCCACCAACATTTGAAGCTATGGAGCTCATTGGTAAA

CCAAAACCCTACTATGAGATTGGTGAACGAGTAGATTATAAGTTGTAAA

AAAGGATACTTCTATATACCTCCTCTTGCCACCCATACTATTTGTGATC

GGAATCATACATGGCTACCTGTCTCAGATGACGCCTGTTATAGAGAAAC

ATGTCCATATATACGGGATCCTTTAAATGGCCAAGCAGTCCCTGCAAAT

GGGACTTACGAGTTTGGTTATCAGATGCACTTTATTTGTAATGAGGGTT

ATTACTTAATTGGTGAAGAAATTCTATATTGTGAACTTAAAGGATCAGT

AGCAATTTGGAGCGGTAAGCCCCCAATATGTGAAAAGGTTTTGTGTACA

CCACCTCCAAAAATAAAAAATGGAAAACACACCTTTAGTGAAGTAGAAG

TATTTGAGTATCTTGATGCAGTAACTTATAGTTGTGATCCTGCACCTGG

ACCAGATCCATTTTCACTTATTGGAGAGAGCACGATTTATTGTGGTGAC

AATTCAGTGTGGAGTCGTGCTGCTCCAGAGTGTAAAGTGGTCAAATGTC

GATTTCCAGTAGTCGAAAATGGAAAACAGATATCAGGATTTGGAAAAAA

ATTTTACTACAAAGCAACAGTTATGTTTGAATGCGATAAGGGTTTTTAC

CTCGATGGCAGCGACACAATTGTCTGTGACAGTAACAGTACTTGGGATC

CCCCAGTTCCAAAGTGTCTTAAAGTGCTGCCTCCATCTAGTACAAAACC

TCCAGCTTTGAGTCATTCAGTGTCGACTTCTTCCACTACAAAATCTCCA

GCGTCCAGTGCCTCAGGTCCTAGGCCTACTTACAAGCCTCCAGTCTCAA

ATTATCCAGGATATCCTAAACCTGAGGAAGGAATACTTGACAGTTTGGA

TGTTTGGGTCATTGCTGTGATTGTTATTGCCATAGTTGTTGGAGTTGCA

GTAATTTGTGTTGTCCCGTACAGATATCTTCAAAGGAGGAAGAAGAAAG

GCACATACCTAACTGATGAGACCCACAGAGAAGTAAAATTTACTTCTCT

CTGA

In some embodiments, the MCP or fragment thereof is soluble MCP.

The MCP fragment is preferably capable of acting as a cofactor for the CFI-mediated cleavage of C3b. The skilled person would be readily able to determine such CFI activity using any suitable method known in the art, for example as disclosed herein.

Preferably, the fragment of MCP is a soluble fragment of MCP, for example generated by removing the transmembrane domains from full length MCP and/or by selecting MCP truncations comprising or consisting of certain SCRs.

In some embodiments, the MCP fragment comprises SCRs 2 and 3. In some embodiments, the MCP fragment comprises SCRs 2, 3 and 4.

In other embodiments, the nucleotide sequence encoding MCP encodes an amino acid sequence that has at least 75%, 80%, 85% 90%, 95%, 96%, 97%, 98% or 99% identity to SEQ ID NO: 26. Preferably, wherein the amino acid sequence substantially retains a functional activity of the protein represented by SEQ ID NO: 26.

In other embodiments, the nucleotide sequence encoding MCP encodes the amino acid sequence SEQ ID NO: 26.

Linkers

In preferred embodiments, the nucleotide sequence encoding (i) is upstream of the nucleotide sequence encoding (ii). In other embodiments, the nucleotide sequence encoding (ii) is upstream of the nucleotide sequence encoding (i).

In some embodiments, the nucleotide sequences encoding the (i) and (ii) are operably linked by a linker. In some embodiments, the linker comprises a self-cleaving 2A peptide sequence, such as a sequence comprising or that is defined by a Furin cleavage site, GSG, 11a1D and an F2A sequence.

In some embodiments, the linker is SEQ ID NO: 17.

(SEQ ID NO: 17)
CGAAGGAAACGAGGAAGCGGAGAAGCCAGACACAAACAGAAAATTGTGG

CACCGGTGAAACAGACTTTGAATTTTGACCTTCTCAAGTTGGCGGGAGA

CGTCGAGTCCAACCCTGGGCCC

In other embodiments, the linker has at least 75%, 80%, 85%, 86%, 87%, 88%, 89%, 90%, 91%, 92%, 93%, 94%, 95%, 96%, 97%, 98% or 99% identity to SEQ ID NO: 17. Preferably, the linker substantially retains a functional activity of SEQ ID NO: 17.

By "operably linked", it is to be understood that the individual components are linked together in a manner which enables them to carry out their function substantially unhindered.

Product

The product of the invention may, for example, be a composition (e.g. a pharmaceutical composition) comprising (i) a Complement Factor I (CFI) cofactor; and (ii) Complement Factor I (CFI), or nucleotide sequences encoding therefor, in admixture. Alternatively, the product may, for example, be a kit comprising preparations of (i) a Complement Factor I (CFI) cofactor; and (ii) Complement Factor I (CFI), or nucleotide sequences encoding therefor, and, optionally, instructions for the simultaneous, sequential or separate administration of the preparations to a subject in need thereof.

The product of the invention may, for example, be a composition (e.g. a pharmaceutical composition) comprising (i) Complement Factor H Like Protein 1 (FHL1) or Complement Factor H (CFH); and (ii) Complement Factor I (CFI), or nucleotide sequences encoding therefor, in admixture. Alternatively, the product may, for example, be a kit comprising preparations of (i) Complement Factor H Like Protein 1 (FHL1) or Complement Factor H (CFH); and (ii) Complement Factor I (CFI), or nucleotide sequences encoding therefor, and, optionally, instructions for the simultaneous, sequential or separate administration of the preparations to a subject in need thereof.

Protein Transduction

As an alternative to the delivery of polynucleotides to cells, the products and agents of the invention may be delivered to cells by protein transduction.

Protein transduction may be via vector delivery (Cai, Y. et al. (2014) Elife 3: e01911; Maetzig, T. et al. (2012) Curr. Gene Ther. 12: 389-409). Vector delivery involves the engineering of viral particles (e.g. lentiviral particles) to comprise the proteins to be delivered to a cell. Accordingly, when the engineered viral particles enter a cell as part of their natural life cycle, the proteins comprised in the particles are carried into the cell.

Protein transduction may be via protein delivery (Gaj, T. et al. (2012) Nat. Methods 9:805-7). Protein delivery may be achieved, for example, by utilising a vehicle (e.g. liposomes) or even by administering the protein itself directly to a cell.

Polynucleotide

Polynucleotides of the invention may comprise DNA or RNA, preferably DNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The nucleotide sequences of the invention disclosed herein may comprise or lack stop codons at their 3' end, for example depending on their position in a bicistronic vector. Thus, the present disclosure encompasses the SEQ ID NOs disclosed herein with the stop codons present or absent.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

In some embodiments, the polynucleotide comprises or consists of the nucleotide sequence of SEQ ID NO: 22, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

```
                                          (SEQ ID NO: 22)
CGCTCGCTCACTGAGGCCGCCCGGGCAAAGCCCGGGCGTCGGGCGACCT
TTGGTCGCCCGGCCTCAGTGAGCGAGCGAGCGCGCAGAGAGGGAGTGGC
CAACTCCATCACTAGGGGTTCCTTGTAGTTAATGATTAACCCGCCATGC
TACTTATCTACGTAGCCATGCTCTAGGTACCGGAGTTCCGCGTTACATA
ACTTACGGTAAATGGCCCGCCTGGCTGACCGCCCAACGACCCCCGCCCA
TTGACGTCAATAATGACGTATGTTCCCATAGTAACGCCAATAGGGACTT
TCCATTGACGTCAATGGGTGGAGTATTTACGGTAAACTGCCCACTTGGC
AGTACATCAAGTGTATCATATGCCAAGTACGCCCCCTATTGACGTCAAT
```

-continued

```
GACGGTAAATGGCCCGCCTGGCATTATGCCCAGTACATGACCTTATGGG
ACTTTCCTACTTGGCAGTACATCTACGTATTAGTCATCGCTATTACCAT
GGTGATGCGGTTTTGGCAGTACATCAATGGGCGTGGATAGCGGTTTGAC
TCACGGGGATTTCCAAGTCTCCACCCCATTGACGTCAATGGGAGTTTGT
TTTGGCACCAAAATCAACGGGACTTTCCAAAATGTCGTAACAACTCCGC
CCCATTGACGCAAATGGGCGGTAGGCGTGTACGGTGGGAGGTCTATATA
AGCAGAGCTCGTTTAGTGAACCGTCAGATCGCCTGGAGACGCCATCCAC
GCTGTTTTGACCTCCATAGAAGACACCGACTAGTGCCACCATGCGCCTC
CTGGCCAAGATCATCTGCCTCATGCTGTGGGCCATCTGCGTGGCTGAGG
ACTGCAATGAGCTGCCGCCCAGGAGGAACACAGAGATCCTGACAGGGAG
CTGGTCTGACCAGACCTACCCTGAGGGCACCCAGGCGATCTACAAGTGC
CGGCCGGGCTACAGGAGCCTGGGGAACATCATCATGGTGTGTAGAAAGG
GCGAATGGGGGCCCTCAACCCCCTGAGGAAGTGCCAGAAGCGGCCCTGT
GGCCACCCCGGGGACACACCCTTCGGGACCTTCACCCTGACCGGCGGCA
ATGTGTTTGAGTACGGCGTGAAGGCTGTCTACACATGCAACGAGGGGTA
CCAGCTGCTGGGCGAGATTAACTACCGGGAGTGTGACACCGATGGGTGG
ACCAACGACATTCCCATCTGTGAGGTGGTCAAGTGTCTCCCCGTGACAG
CCCCAGAAAATGGCAAAATCGTGAGCAGCGCCATGGAGCCTGACCGCGA
ATATCACTTTGGGCAGGCCGTGAGGTTTGTGTGCAACTCGGGCTACAAA
ATTGAAGGTGATGAGGAGATGCACTGCAGCGATGATGGCTTCTGGTCCA
AGGAGAAGCCCAAATGTGTGGAGATCTCCTGCAAGTCTCCCGACGTGAT
CAACGGCAGCCCAATCAGCCAGAAGATTATTTACAAAGAGAACGAGCGC
TTCCAGTACAAGTGTAACATGGGCTATGAGTATTCAGAGAGGGGAGATG
CCGTCTGCACTGAGAGCGGCTGGAGACCACTGCCTAGCTGCGAGGAAAA
GAGTTGTGACAACCCTTACATCCCAAATGGCGACTACTCCCCTCTGCGG
ATCAAACACCGGACCGGGGATGAAATCACCTATCAGTGCCGCAATGGAT
TCTACCCGGCCACCCGCGGCAACACCGCCAAATGCACCAGCACAGGCTG
GATCCCCGCCCCCCGCTGTACGCTGAAGCCTTGCGACTATCCAGACATC
AAGCACGGAGGCCTGTACCACGAAAACATGCGGCGGCCTTATTTCCCTG
TGGCAGTGGGGAAGTACTACAGCTACTACTGCGACGAGCACTTCGAGAC
CCCCTCTGGCTCCTACTGGGACCACATCCACTGCACACAGGACGGCTGG
TCTCCAGCTGTGCCCTGCCTGAGGAAATGCTACTTCCCCTACCTGGAGA
ACGGATACAACCAGAACTATGGCCGCAAGTTCGTGCAGGGCAAGAGCAT
CGATGTGGCCTGCCACCCTGGCTACGCCCTGCCCAAGGCCCAGACAACT
GTGACCTGCATGGAGAATGGTTGGAGCCCCACCCCGCGCTGCATCCGGG
TGTCCTTCACGCTCCGAAGGAAACGAGGAAGCGGAGAAGCCAGACACAA
ACAGAAAATTGTGGCACCGGTGAAACAGACTTTGAATTTTGACCTTCTC
AAGTTGGCGGGAGACGTCGAGTCCAACCCTGGGCCCATGAAACTGCTGC
ATGTCTTCCTCCTCTTCCTGTGCTTCCACCTCCGTTTCTGTAAAGTCAC
CTACACTAGCCAGGAGGATCTGGTGGAGAAGAAATGCCTGGCCAAGAAG
```

-continued

TATACCCACCTGAGCTGCGACAAAGTGTTCTGCCAGCCCTGGCAACGCT

GCATTGAAGGTACTTGTGTGTGCAAGCTGCCCTACCAGTGCCCCAAGAA

CGGCACGGCCGTGTGTGCCACCAACAGGAGGAGCTTCCCCACCTACTGC

CAGCAGAAGAGCCTGGAATGCCTCCACCCTGGCACCAAGTTTCTGAACA

ACGGGACCTGCACAGCCGAGGGGAAATTCAGCGTCTCCCTCAAGCACGG

CAATACAGACTCCGAGGGCATTGTGGAAGTGAAGCTGGTGGACCAGGAC

AAGACCATGTTCATCTGCAAAAGCAGCTGGTCCATGCGGGAGGCCAATG

TCGCCTGCCTGGACCTGGGCTTCCAGCAGGGCGCTGATACACAGCGCCG

CTTTAAACTCAGTGACCTCAGCATCAACAGCACTGAGTGTCTGCACGTG

CACTGCCGGGGCCTGGAGACCAGCCTGGCTGAGTGCACCTTCACCAAGC

GCAGGACCATGGGCTACCAGGATTTTGCAGATGTGGTCTGCTACACCCA

GAAGGCAGACAGCCCCATGGATGACTTCTTCCAGTGTGTCAATGGCAAG

TACATTTCCCAGATGAAGGCTTGTGACGGGATCAATGATTGCGGGGATC

AGAGCGATGAGCTCTGCTGCAAGGCCTGCCAAGGGAAGGGCTTTCACTG

TAAGTCTGGGGTGTGCATCCCTTCTCAGTATCAGTGCAACGGAGAGGTG

GACTGCATCACTGGGGAGGACGAGGTGGGCTGTGCTGGCTTCGCCTCTG

TGGCCCAGGAGGAGACAGAGATCCTCACAGCTGACATGGATGCAGAGCG

GCGGCGCATCAAGAGTCTGCTCCCAAAGCTCTCCTGCGGCGTTAAGAAT

CGCATGCACATCCGGAGGAAGCGGATCGTTGGAGGCAAACGGGCTCAGC

TGGGGGACTTGCCGTGGCAGGTGGCCATCAAAGATGCCTCCGGAATCAC

CTGTGGTGGCATCTACATCGGCGGCTGCTGGATCCTGACCGCCGCCCAC

TGCCTTCGGGCCAGCAAGACTCACCGCTACCAGATCTGGACCACCGTGG

TGGATTGGATTCACCCCGACCTGAAGAGGATTGTCATTGAGTATGTCGA

CCGCATCATCTTCCATGAAAACTACAATGCCGGGACGTATCAGAACGAC

ATCGCCCTCATCGAGATGAAGAAGGATGGGAACAAGAAGGACTGTGAGC

TGCCTCGCTCCATCCCCGCCTGTGTACCATGGTCTCCGTACCTGTTCCA

GCCAAATGACACATGCATCGTGAGCGGCTGGGGCCGCGAGAAAGACAAC

GAGAGGGTCTTCTCCCTGCAGTGGGGTGAAGTCAAGCTGATCAGCAACT

GCTCCAAGTTCTACGGCAACCGCTTCTATGAGAAGGAGATGGAGTGCGC

CGGCACCTATGACGGCAGCATTGACGCGTGCAAGGGAGACAGTGGGGGC

CCCCTGGTCTGCATGGACGCCAACAATGTGACCTACGTGTGGGGAGTTG

TGTCCTGGGGCGAGAACTGTGGCAAGCCTGAGTTCCCGGGCGTGTACAC

AAAGGTGGCAAACTATTTTGACTGGATCTCCTATCACGTTGGCAGGCCC

TTCATTTCACAGTACAACGTATAACTCGAGAATCAACCTCTGGATTACA

AAATTTGTGAAAGATTGACTGGTATTCTTAACTATGTTGCTCCTTTTAC

GCTATGTGGATACGCTGCTTTAATGCCTTTGTATCATGCTATTGCTTCC

CGTATGGCTTTCATTTTCTCCTCCTTGTATAAATCCTGGTTAGTTCTTG

CCACGGCGGAACTCATCGCCGCCTGCCTTGCCCGCTGCTGGACAGGGGC

TCGGCTGTTGGGCACTGACAATTCCGTGGTGTGCCTTCTAGTTGCCAGC

CATCTGTTGTTTGCCCCTCCCCCGTGCCTTCCTTGACCCTGGAAGGTGC

CACTCCCACTGTCCTTTCCTAATAAAATGAGGAAATTGCATCGCATTGT

-continued

CTGAGTAGGTGTCATTCTATTCTGGGGGGTGGGGTGGGGCAGGACAGCA

AGGGGGAGGATTGGGAAGACAATAGCAGGCATGCTGGGGATGCGGTGGG

CTCTATGGCTTCTGAGGCGGAAAGAACCAGCTGGGGCTCGACTAGAGCA

TGGCTACGTAGATAAGTAGCATGGCGGGTTAATCATTAACTACAAGGAA

CCCCTAGTGATGGAGTTGGCCACTCCCTCTCTGCGCGCTCGCTCGCTCA

CTGAGGCCGGGCGACCAAAGGTCGCCCGACGCCCGGGCTTTGCCCGGGC

GGCCTCAGTGAGCGAGCG

In some embodiments, the polynucleotide comprises or consists of the nucleotide sequence of SEQ ID NO: 23, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

(SEQ ID NO: 23)

CGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGC

CAACTCCATCACTAGGGGTTCCTGGCGCGCCGGAGTTCCGCGTTACATA

ACTTACGGTAAATGGCCCGCCTGGCTGACCGCCCAACGACCCCCGCCCA

TTGACGTCAATAATGACGTATGTTCCCATAGTAACGCCAATAGGGACTT

TCCATTGACGTCAATGGGTGGAGTATTTACGGTAAACTGCCCACTTGGC

AGTACATCAAGTGTATCATATGCCAAGTACGCCCCCTATTGACGTCAAT

GACGGTAAATGGCCCGCCTGGCATTATGCCCAGTACATGACCTTATGGG

ACTTTCCTACTTGGCAGTACATCTACGTATTAGTCATCGCTATTACCAT

GGTGATGCGGTTTTGGCAGTACATCAATGGGCGTGGATAGCGGTTTGAC

TCACGGGGATTTCCAAGTCTCCACCCCATTGACGTCAATGGGAGTTTGT

TTTGGCACCAAAATCAACGGGACTTTCCAAAATGTCGTAACAACTCCGC

CCCATTGACGCAAATGGGCGGTAGGCGTGTACGGTGGGAGGTCTATATA

AGCAGAGCTCGTTTAGTGAACCGTCAGATCGCCTGGAGACGCCATCCAC

GCTGTTTTGACCTCCATAGAAGACACCGACTAGTGCCACCATGCGCCTC

CTGGCCAAGATCATCTGCCTCATGCTGTGGGCCATCTGCGTGGCTGAGG

ACTGCAATGAGCTGCCGCCCAGGAGGAACACAGAGATCCTGACAGGGAG

CTGGTCTGACCAGACCTACCCTGAGGGCACCCAGGCGATCTACAAGTGC

CGGCCGGGCTACAGGAGCCTGGGGAACATCATCATGGTGTGTAGAAAGG

GCGAATGGGTGGCCCTCAACCCCCTGAGGAAGTGCCAGAAGCGGCCCTG

TGGCCACCCCGGGGACACACCCTTCGGGACCTTCACCCTGACCGGCGGC

AATGTGTTTGAGTACGGCGTGAAGGCTGTCTACACATGCAACGAGGGGT

ACCAGCTGCTGGGCGAGATTAACTACCGGGAGTGTGACACCGATGGGTG

GACCAACGACATTCCCATCTGTGAGGTGGTCAAGTGTCTCCCCGTGACA

GCCCCAGAAAATGGCAAAATCGTGAGCAGCGCCATGGAGCCTGACCGCG

AATATCACTTTGGGCAGGCCGTGAGGTTTGTGTGCAACTCGGGCTACAA

AATTGAAGGTGATGAGGAGATGCACTGCAGCGATGATGGCTTCTGGTCC

AAGGAGAAGCCCAAATGTGTGGAGATCTCCTGCAAGTCTCCCGACGTGA

-continued

```
TCAACGGCAGCCCAATCAGCCAGAAGATTATTTACAAAGAGAACGAGCG
CTTCCAGTACAAGTGTAACATGGGCTATGAGTATTCAGAGAGGGGAGAT
GCCGTCTGCACTGAGAGCGGCTGGAGACCACTGCCTAGCTGCGAGGAAA
AGAGTTGTGACAACCCTTACATCCCAAATGGCGACTACTCCCCTCTGCG
GATCAAACACCGGACCGGGGATGAAATCACCTATCAGTGCCGCAATGGA
TTCTACCCGGCCACCCGCGGCAACACCGCCAAATGCACCAGCACAGGCT
GGATCCCCGCCCCCCGCTGTACGCTGAAGCCTTGCGACTATCCAGACAT
CAAGCACGGAGGCCTGTACCACGAAAACATGCGGCGGCCTTATTTCCCT
GTGGCAGTGGGGAAGTACTACAGCTACTACTGCGACGAGCACTTCGAGA
CCCCCTCTGGCTCCTACTGGGACCACATCCACTGCACACAGGACGGCTG
GTCTCCAGCTGTGCCCTGCCTGAGGAAATGCTACTTCCCCTACCTGGAG
AACGGATACAACCAGAACTATGGCCGCAAGTTCGTGCAGGGCAAGAGCA
TCGATGTGGCCTGCCACCCTGGCTACGCCCTGCCCAAGGCCCAGACAAC
TGTGACCTGCATGGAGAATGGTTGGAGCCCCACCCCGCGCTGCATCCGG
GTGTCCTTCACGCTCCGAAGGAAACGAGGAAGCGGAGAAGCCAGACACA
AACAGAAAATTGTGGCACCGGTGAAACAGACTTTGAATTTTGACCTTCT
CAAGTTGGCGGGAGACGTCGAGTCCAACCCTGGGCCCATGAAACTGCTG
CATGTCTTCCTCCTCTTCCTGTGCTTCCACCTCCGTTTCTGTAAAGTCA
CCTACACTAGCCAGGAGGATCTGGTGGAGAAGAAATGCCTGGCCAAGAA
GTATACCCACCTGAGCTGCGACAAAGTGTTCTGCCAGCCCTGGCAACGC
TGCATTGAAGGTACTTGTGTGTGCAAGCTGCCCTACCAGTGCCCCAAGA
ACGGCACGGCCGTGTGTGCCACCAACAGGAGGAGCTTCCCCACCTACTG
CCAGCAGAAGAGCCTGGAATGCCTCCACCCTGGCACCAAGTTTCTGAAC
AACGGGACCTGCACAGCCGAGGGGAAATTCAGCGTCTCCCTCAAGCACG
GCAATACAGACTCCGAGGGCATTGTGGAAGTGAAGCTGGTGGACCAGGA
CAAGACCATGTTCATCTGCAAAAGCAGCTGGTCCATGCGGGAGGCCAAT
GTCGCCTGCCTGGACCTGGGCTTCCAGCAGGGCGCTGATACACAGCGCC
GCTTTAAACTCAGTGACCTCAGCATCAACAGCACTGAGTGTCTGCACGT
GCACTGCCGGGGCCTGGAGACCAGCCTGGCTGAGTGCACCTTCACCAAG
CGCAGGACCATGGGCTACCAGGATTTTGCAGATGTGGTCTGCTACACCC
AGAAGGCAGACAGCCCCATGGATGACTTCTTCCAGTGTGTCAATGGCAA
GTACATTTCCCAGATGAAGGCTTGTGACGGGATCAATGATTGCGGGGAT
CAGAGCGATGAGCTCTGCTGCAAGGCCTGCCAAGGGAAGGGCTTTCACT
GTAAGTCTGGGGTGTGCATCCCTTCTCAGTATCAGTGCAACGGAGAGGT
GGACTGCATCACTGGGGAGGACGAGGTGGGCTGTGCTGGCTTCGCCTCT
GTGGCCCAGGAGGAGACAGAGATCCTCACAGCTGACATGGATGCAGAGC
GGCGGCGCATCAAGAGTCTGCTCCCAAAGCTCTCCTGCGGCGTTAAGAA
TCGCATGCACATCCGGAGGAAGCGGATCGTTGGAGGCAAACGGGCTCAG
CTGGGGGACTTGCCGTGGCAGGTGGCCATCAAAGATGCCTCCGGAATCA
CCTGTGGTGGCATCTACATCGGCGGCTGCTGGATCCTGACCGCCGCCCA
CTGCCTTCGGGCCAGCAAGACTCACCGCTACCAGATCTGGACCACCGTG
```

-continued

```
GTGGATTGGATTCACCCCGACCTGAAGAGGATTGTCATTGAGTATGTCG
ACCGCATCATCTTCCATGAAAACTACAATGCCGGGACGTATCAGAACGA
CATCGCCCTCATCGAGATGAAGAAGGATGGGAACAAGAAGGACTGTGAG
CTGCCTCGCTCCATCCCCGCCTGTGTACCATGGTCTCCGTACCTGTTCC
AGCCAAATGACACATGCATCGTGAGCGGCTGGGGCCGCGAGAAAGACAA
CGAGAGGGTCTTCTCCCTGCAGTGGGGTGAAGTCAAGCTGATCAGCAAC
TGCTCCAAGTTCTACGGCAACCGCTTCTATGAGAAGGAGATGGAGTGCG
CCGGCACCTATGACGGCAGCATTGACGCGTGCAAGGGAGACAGTGGGGG
CCCCCTGGTCTGCATGGACGCCAACAATGTGACCTACGTGTGGGGAGTT
GTGTCCTGGGGCGAGAACTGTGGCAAGCCTGAGTTCCCGGGCGTGTACA
CAAAGGTGGCAAACTATTTTGACTGGATCTCCTATCACGTTGGCAGGCC
CTTCATTTCACAGTACAACGTATAACTCGAGAATCAACCTCTGGATTAC
AAAATTTGTGAAAGATTGACTGGTATTCTTAACTATGTTGCTCCTTTTA
CGCTATGTGGATACGCTGCTTTAATGCCTTTGTATCATGCTATTGCTTC
CCGTATGGCTTTCATTTTCTCCTCCTTGTATAAATCCTGGTTAGTTCTT
GCCACGGCGGAACTCATCGCCGCCTGCCTTGCCCGCTGCTGGACAGGGG
CTCGGCTGTTGGGCACTGACAATTCCGTGGTGTGCCTTCTAGTTGCCAG
CCATCTGTTGTTTGCCCCTCCCCCGTGCCTTCCTTGACCCTGGAAGGTG
CCACTCCCACTGTCCTTTCCTAATAAAATGAGGAAATTGCATCGCATTG
TCTGAGTAGGTGTCATTCTATTCTGGGGGGTGGGGGGGGCAGGACAGCA
AGGGGGAGGATTGGGAAGACAATAGCAGGCATGCTGGGGATGCGGTGGG
CTCTATGGGCGGCCGCAGGAACCCCTAGTGATGGAGTTGGCCACTCCCT
CTCTGCGCGCTCGCTCGCTCACTGAGGCCGGGCGACCAAAGGTCGCCCG
ACGCCCGGGCTTTGCCCGGGCGGCCTCAGTGAGCGAGCG
```

Structure of the Eye

The medicaments disclosed herein may be delivered to a mammalian, preferably human eye in relation to the treatment or prevention of an eye disease, such as age-related macular degeneration (AMD).

The person skilled in the treatment of diseases of the eye will have a detailed and thorough understanding of the structure of the eye. However, the following structures of particular relevance to the invention are described.

Retina

The retina is the multi-layered membrane, which lines the inner posterior chamber of the eye and senses an image of the visual world which is communicated to the brain via the optic nerve. In order from the inside to the outside of the eye, the retina comprises the layers of the neurosensory retina and retinal pigment epithelium, with the choroid lying outside the retinal pigment epithelium.

Neurosensory Retina and Photoreceptor Cells

The neurosensory retina harbours the photoreceptor cells that directly sense light. It comprises the following layers: internal limiting membrane (ILM); nerve fibre layer; ganglion cell layer; inner plexiform layer; inner nuclear layer; outer plexiform layer; outer nuclear layer (nuclei of the photoreceptors); external limiting membrane (ELM); and photoreceptors (inner and outer segments of the rods and cones).

The skilled person will have a detailed understanding of photoreceptor cells. Briefly, photoreceptor cells are specialised neurons located in the retina that convert light into biological signals. Photoreceptor cells comprise rod and cone cells, which are distributed differently across the retina.

Rod cells are distributed mainly across the outer parts of the retina. They are highly sensitive and provide for vision at low light levels. There are on average about 125 million rod cells in a normal human retina.

Cone cells are found across the retina, but are particularly highly concentrated in the fovea, a pit in the neurosensory retina that is responsible for central high resolution vision. Cone cells are less sensitive than rod cells. There are on average about 6-7 million cone cells in a normal human retina.

Retinal Pigment Epithelium

The retinal pigment epithelium (RPE) is a pigmented layer of cells located immediately to the outside of the neurosensory retina. The RPE performs a number of functions, including transport of nutrients and other substances to the photoreceptor cells, and absorption of scattered light to improve vision.

Choroid

The choroid is the vascular layer situated between the RPE and the outer sclera of the eye. The vasculature of the choroid enables provision of oxygen and nutrients to the retina.

Age-Related Macular Degeneration (AMD)

The clinical progression of age-related macular degeneration (AMD) is characterised in stages according to changes in the macula. The hallmark of early AMD is the appearance of drusen, which are accumulations of extracellular debris underneath the retina and appear as yellow spots in the retina during clinical examination and on fundus photographs. Drusen are categorised by size as small (<63 μm), medium (63-124 μm) and large (>124 μm). They are also considered as hard or soft depending on the appearance of their margins on opthalmological examination. While hard drusen have clearly defined margins, soft drusen have less defined, fluid margins. The Age-related Eye Disease Study (AREDS) fundus photographic severity scale is one of the main classification systems used for this condition.

AMD is classified into “dry” and “wet” (exudative or neovascular) forms. Dry AMD is more common than wet AMD, but the dry form can progress to the wet form, and the two occur simultaneously in a significant number of cases. Dry AMD is typically characterised by progressive apoptosis of cells in the RPE layer, overlying photoreceptor cells, and frequently also the underlying cells in the choroidal capillary layer. Confluent areas of RPE cell death accompanied by overlying photoreceptor atrophy are referred to as geographic atrophy (GA). Patients with this form of AMD experience a slow and progressive deterioration in central vision.

Wet AMD is characterised by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularisation (CNV) and its secondary complications.

The treatment or prevention of AMD described herein may reduce or prevent the appearance of an AMD phenotype described above. Preferably, the treatment of AMD enables maintenance or improvement in visual function.

In some embodiments, the treatment or prevention of AMD results in a prevention of or reduction in the formation of geographic atrophy. In other embodiments, the treatment or prevention of AMD results in slowing the progression of geographic atrophy. For example, it results in an at least 10%, 20%, 30%, 40%, 50%, 60%, 70%, 80% or 90% reduction in the increase in GA area over the 12 months following administration to a treated eye of a subject, relative to an untreated eye over the same period. In other embodiments, the treatment or prevention of AMD results in the treatment of geographic atrophy, for example a reduction in the amount of geographic atrophy.

In some embodiments, the treatment or prevention of AMD results in a prevention of or reduction in the formation of drusen. In other embodiments, the treatment or prevention of AMD results in a reduction in existing drusen, for example a reduction in the size and/or number of existing drusen.

In some embodiments, the treatment or prevention of AMD results in a prevention of or reduction in complement deposition. In other embodiments, the treatment or prevention of AMD results in a reduction in existing complement deposition.

In some embodiments, the treatment or prevention of AMD results in an improvement in or restoration of vision or visual acuity. In other embodiments, the treatment or prevention of AMD mitigates the loss of vision or visual acuity.

In some embodiments, the treatment or prevention of AMD results in an improvement in or restoration of reading speed in a subject. In other embodiments, the treatment or prevention of AMD mitigates the reduction in reading speed in a subject.

In some embodiments, the treatment or prevention of AMD results in a reduction or prevention of loss of photoreceptors and/or the retinal pigment epithelium (RPE).

Diabetic Retinopathy

Diabetic retinopathy is a condition characterised by damage to the blood vessels of the retina, which is caused by the high blood sugar levels associated with diabetes. If left untreated, diabetic retinopathy can cause blindness.

Although subjects with mild diabetic retinopathy may have good vision, certain types of diabetic retinopathy, namely diabetic macular oedema (DMO) and proliferative diabetic retinopathy (PDR) may threaten the sight of the subject.

Diabetic macular oedema is characterised by the leakage of fluid from the damaged blood vessels in the back of the eye. The leaked fluid accumulates in the macula, which leads to swelling and blurred vision. This can eventually give rise to poor central vision and an inability to read or drive. Side vision usually remains normal.

Proliferative diabetic retinopathy is characterised by the closure of retinal blood vessels, leading to the growth of abnormal, fragile blood vessels on the surface of the retina. This may result in permanent loss of vision due to bleeding into the eye, scarring and retinal detachment. Non-proliferative retinopathy is the early stage of diabetic retinopathy which may lead to proliferative retinopathy if left untreated. Therefore treatments are contemplated to all stages and types of diabetic retinopathy.

Vectors

A vector is a tool that allows or facilitates the transfer of an entity from one environment to another.

Adeno-Associated Viral (AAV) Vectors

In one aspect, the invention provides an AAV vector comprising a polynucleotide of the invention.

Preferably, the AAV vector is in the form of an AAV vector particle.

Methods of preparing and modifying viral vectors and viral vector particles, such as those derived from AAV, are well known in the art.

The AAV vector may comprise an AAV genome or a fragment or derivative thereof.

AAV is known to be capable of packaging genomes up to 5.2 kb in size (Dong, J.-Y. et al. (1996) Human Gene Therapy 7: 2101-2112).

An AAV genome is a polynucleotide sequence, which may encode functions needed for production of an AAV particle. These functions include those operating in the replication and packaging cycle of AAV in a host cell, including encapsidation of the AAV genome into an AAV particle. Naturally occurring AAVs are replication-deficient and rely on the provision of helper functions in trans for completion of a replication and packaging cycle. Accordingly, the AAV genome of the AAV vector of the invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype, isolate or clade of AAV. Thus, the AAV genome may be the full genome of a naturally occurring AAV. As is known to the skilled person, AAVs occurring in nature may be classified according to various biological systems.

Commonly, AAVs are referred to in terms of their serotype. A serotype corresponds to a variant subspecies of AAV which, owing to its profile of expression of capsid surface antigens, has a distinctive reactivity which can be used to distinguish it from other variant subspecies. Typically, a virus having a particular AAV serotype does not efficiently cross-react with neutralising antibodies specific for any other AAV serotype.

AAV serotypes include AAV1, AAV2, AAV3, AAV4, AAV5, AAV6, AAV7, AAV8, AAV9, AAV10 and AAV11, and also recombinant serotypes, such as Rec2 and Rec3, recently identified from primate brain. Any of these AAV serotypes may be used in the invention.

In some embodiments, the AAV vector particle is an AAV1, AAV2, AAV3, AAV4, AAV5, AAV6, AAV7, AAV8, AAV9, AAV10, AAV11, Rec2 or Rec3 AAV vector particle.

In some embodiments, the AAV may be an AAV1, AAV2, AAV5, AAV7 or AAV8 serotype.

In some embodiments, the AAV may be an AAV2 or AAV8 serotype.

In some embodiments, the AAV may be an AAV2 serotype. In other embodiments, the AAV may be an AAV8 serotype.

The capsid protein may be a mutant capsid protein such as disclosed in WO 2008/124724, which is hereby incorporated by reference.

In some embodiments, the AAV vector comprises an AAV8 capsid with an Y733F mutation.

Reviews of AAV serotypes may be found in Choi et al. (2005) Curr. Gene Ther. 5: 299-310 and Wu et al. (2006) Molecular Therapy 14: 316-27. The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV may also be referred to in terms of clades or clones. This refers to the phylogenetic relationship of naturally derived AAVs, and typically to a phylogenetic group of AAVs which can be traced back to a common ancestor, and includes all descendants thereof. Additionally, AAVs may be referred to in terms of a specific isolate, i.e. a genetic isolate of a specific AAV found in nature. The term genetic isolate describes a population of AAVs which has undergone limited genetic mixing with other naturally occurring AAVs, thereby defining a recognisably distinct population at a genetic level.

The skilled person can select an appropriate serotype, clade, clone or isolate of AAV for use in the invention on the basis of their common general knowledge. For instance, the AAV5 capsid has been shown to transduce primate cone photoreceptors efficiently as evidenced by the successful correction of an inherited colour vision defect (Mancuso et al. (2009) Nature 461: 784-7).

The AAV serotype determines the tissue specificity of infection (or tropism) of an AAV. Accordingly, preferred AAV serotypes for use in AAVs administered to patients in accordance with the invention are those which have natural tropism for or a high efficiency of infection of target cells within the eye. In some embodiments, AAV serotypes for use in the invention are those which transduce cells of the neurosensory retina, retinal pigment epithelium and/or choroid.

Typically, the AAV genome of a naturally derived serotype, isolate or clade of AAV comprises at least one inverted terminal repeat sequence (ITR). An ITR sequence acts in cis to provide a functional origin of replication and allows for integration and excision of the vector from the genome of a cell. In preferred embodiments, one or more ITR sequences flank the nucleotide sequences encoding the Complement Factor I, and/or Complement Factor H or FHL1. The AAV genome typically also comprises packaging genes, such as rep and/or cap genes which encode packaging functions for an AAV particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV particle. Capsid variants are discussed below.

A promoter will be operably linked to each of the packaging genes. Specific examples of such promoters include the p5, p19 and p40 promoters (Laughlin et al. (1979) Proc. Natl. Acad. Sci. USA 76: 5567-5571). For example, the p5 and p19 promoters are generally used to express the rep gene, while the p40 promoter is generally used to express the cap gene.

As discussed above, the AAV genome used in the AAV vector of the invention may therefore be the full genome of a naturally occurring AAV. For example, a vector comprising a full AAV genome may be used to prepare an AAV vector or vector particle in vitro. However, while such a vector may in principle be administered to patients, this will rarely be done in practice. Preferably, the AAV genome will be derivatised for the purpose of administration to patients. Such derivatisation is standard in the art and the invention encompasses the use of any known derivative of an AAV genome, and derivatives which could be generated by applying techniques known in the art. Derivatisation of the AAV genome and of the AAV capsid are reviewed in Coura and Nardi (2007) Virology Journal 4: 99, and in Choi et al. and Wu et al., referenced above.

Derivatives of an AAV genome include any truncated or modified forms of an AAV genome which allow for expression of a transgene from an AAV vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences, i.e. a self-complementary AAV genome. This allows for bypass of DNA replication in the target cell, and so enables accelerated transgene expression.

The one or more ITRs will preferably flank the nucleotide sequence encoding the Complement Factor I, and/or CFI cofactor (e.g. Complement Factor H or FHL1) at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

The following portions could therefore be removed in a derivative of the invention: one inverted terminal repeat (ITR) sequence, the replication (rep) and capsid (cap) genes. However, in some embodiments, derivatives may additionally include one or more rep and/or cap genes or other viral sequences of an AAV genome. Naturally occurring AAV integrates with a high frequency at a specific site on human chromosome 19, and shows a negligible frequency of random integration, such that retention of an integrative capacity in the vector may be tolerated in a therapeutic setting.

Where a derivative comprises capsid proteins i.e. VP1, VP2 and/or VP3, the derivative may be a chimeric, shuffled or capsid-modified derivative of one or more naturally occurring AAVs. In particular, the invention encompasses the provision of capsid protein sequences from different serotypes, clades, clones, or isolates of AAV within the same vector (i.e. a pseudotyped vector).

Chimeric, shuffled or capsid-modified derivatives will be typically selected to provide one or more desired functionalities for the AAV vector. Thus, these derivatives may display increased efficiency of gene delivery, decreased immunogenicity (humoral or cellular), an altered tropism range and/or improved targeting of a particular cell type compared to an AAV vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al. (2008) ARVO Abstract: D1048). The unrelated protein may also be one which assists purification of the viral particle as part of the production process, i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al., referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The AAV vector of the invention may take the form of a nucleotide sequence comprising an AAV genome or derivative thereof and a sequence encoding the Complement Factor I, and/or Complement Factor H or FHL1 transgene or derivatives thereof.

The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral capsid. The AAV particle also includes chemically modified forms bearing ligands adsorbed to the capsid surface. For example, such ligands may include antibodies for targeting a particular cell surface receptor.

Thus, for example, the AAV particles of the invention include those with an AAV2 genome and AAV2 capsid proteins (AAV2/2), those with an AAV2 genome and AAV5 capsid proteins (AAV2/5) and those with an AAV2 genome and AAV8 capsid proteins (AAV2/8), as well as those with an AAV2 genome and capsid proteins of more than one serotype.

The AAV vector may comprise multiple copies (e.g., 2, 3 etc.) of the nucleotide sequence referred to herein.

In some embodiments, the polynucleotide further comprises one or more AAV ITRs. In preferred embodiments, the polynucleotide further comprises two AAV ITRs. In some embodiments, the polynucleotide comprises an AAV ITR at its 5' end and an AAV ITR at its 3' end. In some embodiments, the AAV ITRs are AAV2 or AAV8 ITRs. In preferred embodiments, the AAV ITRs are AAV2 ITRs.

In some embodiments, the polynucleotide comprises a 5' AAV ITR with the nucleotide sequence of SEQ ID NO: 18, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

SEQ ID NO: 18

```
CGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGC

CAACTCCATCACTAGGGGTTCCT
```

In some embodiments, the polynucleotide further comprises the nucleotide sequence of SEQ ID NO: 20, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto, immediately adjacent to the 3' end of the 5' ITR.

SEQ ID NO: 20

```
TGTAGTTAATGATTAACCCGCCATGCTACTTATCTACGTAGCCATGCTC
TAGGTACC
```

In some embodiments, the polynucleotide comprises a 3' AAV ITR with the nucleotide sequence of SEQ ID NO: 19, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto.

SEQ ID NO: 19

```
AGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCC

CGGGCGGCCTCAGTGAGCGAGCG
```

In some embodiments, the polynucleotide further comprises the nucleotide sequence of SEQ ID NO: 21, or a nucleotide sequence that has at least 75%, 80%, 85%, 86%, 87%, 88%, 89%, 90%, 91%, 92%, 93%, 94%, 95%, 96%, 97%, 98% or 99% sequence identity thereto, immediately adjacent to the 5' end of the 3' ITR.

SEQ ID NO: 21

```
CTTCTGAGGCGGAAAGAACCAGCTGGGGCTCGACTAGAGCATGGCTACG
TAGATAAGTAGCATGGCGGGTTAATCATTAACTACA
```

Promoters and Regulatory Sequences

The polynucleotide or vector of the invention may also include elements allowing for the expression of the Complement Factor I and CFI cofactor, such as Complement Factor H and/or FHL1 transgenes in vitro or in vivo. These may be referred to as expression control sequences. Thus, the polynucleotide or vector typically comprises expression control sequences (e.g. comprising a promoter sequence) operably linked to the nucleotide sequence encoding the transgene.

In some embodiments, the polynucleotide or vector comprises nucleotide sequences encoding: (a) a CMV promoter, optionally wherein the CMV promoter is upstream of the nucleotide sequences encoding the Complement Factor I and/or a Complement Factor I (CFI) cofactor, such as Complement Factor H and/or FHL1; (b) a WPRE regulatory element, optionally wherein the WPRE regulatory element is downstream of the nucleotide sequences encoding the Complement Factor I and/or a Complement Factor I (CFI) cofactor, such as Complement Factor H and/or FHL1; and/or (c) a poly-A signal, such as a Bovine Growth Hormone poly-A signal, optionally wherein the poly-A signal is downstream of the nucleotide sequences encoding the Complement Factor I and/or a Complement Factor I (CFI) cofactor, such as Complement Factor H and/or FHL1.

In preferred embodiments, the polynucleotide or vector comprises:

(a) a 5' AAV ITR;

(b) a CMV promoter;

(c) a nucleotide sequence encoding a Complement Factor I (CFI) cofactor, preferably FHL1;

(d) a linker, optionally wherein the linker comprises or is defined by a Furin cleavage site, GSG, 11a1D and an F2A sequence;

(e) a nucleotide sequence encoding CFI;

(f) a WPRE regulatory element, preferably wherein the WPRE regulatory element is a WPRE3 regulatory element;

(g) a Bovine Growth Hormone poly-A signal; and (h) a 3' AAV ITR.

Any suitable promoter may be used, the selection of which may be readily made by the skilled person. The promoter sequence may be constitutively active (i.e. operational in any host cell background), or alternatively may be active only in a specific host cell environment, thus allowing for targeted expression of the transgene in a particular cell type (e.g. a tissue-specific promoter). The promoter may show inducible expression in response to presence of another factor, for example a factor present in a host cell. In any event, where the vector is administered for therapy, it is preferred that the promoter should be functional in the target cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters, which are not retinal-cell specific, include the chicken beta-actin (CBA) promoter, optionally in combination with a cytomegalovirus (CMV) enhancer element. An example promoter for use in the invention is a CAG promoter, for example the promoter used in the rAVE expression cassette (GeneDetect.com).

In preferred embodiments, the polynucleotide or vector comprises a CMV promoter.

An example CMV promoter sequence is:

(SEQ ID NO: 13)

```
GGAGTTCCGCGTTACATAACTTACGGTAAATGGCCCGCCTGGCTGACCG
CCCAACGACCCCCGCCCATTGACGTCAATAATGACGTATGTTCCCATAG
TAACGCCAATAGGGACTTTCCATTGACGTCAATGGGTGGAGTATTTACG
GTAAACTGCCCACTTGGCAGTACATCAAGTGTATCATATGCCAAGTACG
CCCCCTATTGACGTCAATGACGGTAAATGGCCCGCCTGGCATTATGCCC
AGTACATGACCTTATGGGACTTTCCTACTTGGCAGTACATCTACGTATT
AGTCATCGCTATTACCATGGTGATGCGGTTTTGGCAGTACATCAATGGG
CGTGGATAGCGGTTTGACTCACGGGGATTTCCAAGTCTCCACCCCATTG
ACGTCAATGGGAGTTTGTTTTGGCACCAAAATCAACGGGACTTTCCAAA
ATGTCGTAACAACTCCGCCCCATTGACGCAAATGGGCGGTAGGCGTGTA
CGGTGGGAGGTCTATATAAGCAGAGCTCGTTTAGTGAACCGTCAGATCG
CCTGGAGACGCCATCCACGCTGTTTTGACCTCCATAGAAGACACCG
```

In some embodiments, the polynucleotide or vector comprises a promoter with a nucleotide sequence that has at least 75%, 80%, 85% 90%, 95%, 96%, 97%, 98% or 99% identity to SEQ ID NO: 13. Preferably, wherein the nucleotide sequence substantially retains the functional activity of the promoter represented by SEQ ID NO: 13.

In other embodiments, the polynucleotide or vector comprises a promoter with the nucleotide sequence of SEQ ID NO: 13.

A further example promoter sequence is:

(SEQ ID NO: 5)

```
ATTGACGTCAATAATGACGTATGTTCCCATAGTAACGCCAATAGGGACT
TTCCATTGACGTCAATGGGTGGAGTATTTACGGTAAACTGCCCACTTGG
CAGTACATCAAGTGTATCATATGCCAAGTACGCCCCCTATTGACGTCAA
TGACGGTAAATGGCCCGCCTGGCATTATGCCCAGTACATGACCTTATGG
GACTTTCCTACTTGGCAGTACATCTACGTATTAGTCATCGCTATTACCA
TGGTCGAGGTGAGCCCCACGTTCTGCTTCACTCTCCCCATCTCCCCCCC
CTCCCCACCCCCAATTTTGTATTTATTTATTTTTTAATTATTTTGTGCA
```

-continued

```
GCGATGGGGGGGGGGGGGGGGGGGGGGGGCGCGCCAGGCGGGGGGGGGC
GGGGCGAGGGGCGGGGCGGGGCGAGGCGGAGAGGTGCGGCGGCAGCCAA
TCAGAGCGGCGCGCTCCGAAAGTTTCCTTTTATGGCGAGGCGGCGGCGG
CGGCGGCCCTATAAAAAGCGAAGCGCGCGGCGGGCGGGAGTCGCTGCGC
GCTGCCTTCGCCCCGTGCCCCGCTCCGCCGCCGCCTCGCGCCGCCCGCC
CCGGCTCTGACTGACCGCGTTACTCCCACAGGTGAGCGGGGGACGGCC
CTTCTCCTCCGGGCTGTAATTAGCGCTTGGTTTAATGACGGCTTGTTTC
TTTTCTGTGGCTGCGTGAAAGCCTTGAGGGGCTCCGGGAGGGCCCTTTG
TGCGGGGGGAGCGGCTCGGGGCTGTCCGCGGGGGGACGGCTGCCTTCGG
GGGGGACGGGGCAGGGCGGGGTTCGGCTTCTGGCGTGTGACCGGCGGCT
CTAGAGCCTCTGCTAACCATGTTCATGCCTTCTTCTTTTTCCTACAGCT
CCTGGGCAACGTGCTGGTTATTGTGCTGTCTCATCATTTTGGCAAAGAA
TT
```

In some embodiments, the polynucleotide or vector comprises a promoter with a nucleotide sequence that has at least 75%, 80%, 85% 90%, 95%, 96%, 97%, 98% or 99% identity to SEQ ID NO: 5. Preferably, wherein the nucleotide sequence substantially retains the functional activity of the promoter represented by SEQ ID NO: 5.

In other embodiments, the polynucleotide or vector comprises a promoter with the nucleotide sequence of SEQ ID NO: 5.

Examples of promoters based on human sequences that would induce retina-specific gene expression include rhodopsin kinase for rods and cones (Allocca et al. (2007) J. Virol. 81: 11372-80), PR2.1 for cones only (Mancuso et al. (2009) Nature 461: 784-7) and/or RPE65 (Bainbridge et al. (2008) N. Engl. J. Med. 358: 2231-9) or VMD2 (Esumi et al. (2004) J. Biol. Chem. 279: 19064-73) for the retinal pigment epithelium.

The polynucleotide or vector of the invention may also comprise one or more additional regulatory sequences which may act pre- or post-transcriptionally. The regulatory sequence may be part of the native transgene locus or may be a heterologous regulatory sequence. The polynucleotide or vector of the invention may comprise portions of the 5'-UTR or 3'-UTR from the native transgene transcript.

Regulatory sequences are any sequences which facilitate expression of the transgene, i.e. act to increase expression of a transcript, improve nuclear export of mRNA or enhance its stability. Such regulatory sequences include for example enhancer elements, post-transcriptional regulatory elements and polyadenylation sites.

A preferred polyadenylation site is the Bovine Growth Hormone poly-A (bGH poly-A) signal.

An example Bovine Growth Hormone poly-A (bGH poly-A) signal is:

(SEQ ID NO: 14)

```
GTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGA
GGAAATTGCATCGCATTGTCTGAGTAGGTGTCATTCTATTCTGGGGGGT
GGGGGGGGCAGGACAGCAAGGGGGAGGATTGGGAAGACAATAGCAGGCA
TGCTGGGGATGCGGTGGGCTCTATGG
```

A further example Bovine Growth Hormone poly-A (bGH poly-A) signal is:

```
                                          (SEQ ID NO: 6)
TCGCTGATCAGCCTCGACTGTGCCTTCTAGTTGCCAGCCATCTGTTGTT

TGCCCCTCCCCCGTGCCTTCCTTGACCCTGGAAGGTGCCACTCCCACTG

TCCTTTCCTAATAAAATGAGGAAATTGCATCGCATTGTCTGAGTAGGTG

TCATTCTATTCTGGGGGGTGGGGTGGGGCAGGACAGCAAGGGGGAGGAT

TGGGAAGACAATAGCAGGCATGCTGGGGATGCGGTGGGCTCTATGGCTT

CTGAGGCGGAAAGAACCAGCTGGGG
```

In some embodiments, the polynucleotide or vector comprises a polyadenylation signal with a nucleotide sequence that has at least 75%, 80%, 85%, 90%, 95%, 96%, 97%, 98% or 99% identity to SEQ ID NO: 14 or 6, preferably SEQ ID NO: 14. Preferably, wherein the nucleotide sequence substantially retains the functional activity of the polyadenylation signal represented by SEQ ID NO: 14 or 6.

In other embodiments, the polynucleotide or vector comprises a polyadenylation signal with the nucleotide sequence of SEQ ID NO: 14 or 6, preferably SEQ ID NO: 14.

In the context of the polynucleotide or vector of the invention, such regulatory sequences will be cis-acting. However, the invention also encompasses the use of trans-acting regulatory sequences located on additional genetic constructs.

A preferred post-transcriptional regulatory element for use in a AAV vector of the invention is the woodchuck hepatitis post-transcriptional regulatory element (WPRE) or a variant thereof.

An example WPRE is:

```
                                          (SEQ ID NO: 7)
ATCAACCTCTGGATTACAAAATTTGTGAAAGATTGACTGGTATTCTTAA

CTATGTTGCTCCTTTTACGCTATGTGGATACGCTGCTTTAATGCCTTTG

TATCATGCTATTGCTTCCCGTATGGCTTTCATTTTCTCCTCCTTGTATA

AATCCTGGTTGCTGTCTCTTTATGAGGAGTTGTGGCCCGTTGTCAGGCA

ACGTGGCGTGGTGTGCACTGTGTTTGCTGACGCAACCCCCACTGGTTGG

GGCATTGCCACCACCTGTCAGCTCCTTTCCGGGACTTTCGCTTTCCCCC

TCCCTATTGCCACGGCGGAACTCATCGCCGCCTGCCTTGCCCGCTGCTG

GACAGGGGCTCGGCTGTTGGGCACTGACAATTCCGTGGTGTTGTCGGGG

AAATCATCGTCCTTTCCTTGGCTGCTCGCCTGTGTTGCCACCTGGATTC

TGCGCGGGACGTCCTTCTGCTACGTCCCTTCGGCCCTCAATCCAGCGGA

CCTTCCTTCCCGCGGCCTGCTGCCGGCTCTGCGGCCTCTTCCGCGTCTT

CGCCTTCGCCCTCAGACGAGTCGGATCTCCCTTTGGGCCGCCTCCCCGC
```

WPRE is a tripartite element containing gamma, alpha and beta elements, in the given order. A shortened version of WPRE, which contains only minimal gamma and alpha elements (referred to as WPRE3; Choi, J.-H. et al. (2014) Molecular Brain 7:17), may also be used in the invention.

An example WPRE3 sequence is:

```
                                          (SEQ ID NO: 15)
AATCAACCTCTGGATTACAAAATTTGTGAAAGATTGACTGGTATTCTTA

ACTATGTTGCTCCTTTTACGCTATGTGGATACGCTGCTTTAATGCCTTT
```

```
-continued
GTATCATGCTATTGCTTCCCGTATGGCTTTCATTTTCTCCTCCTTGTAT

AAATCCTGGTTAGTTCTTGCCACGGCGGAACTCATCGCCGCCTGCCTTG

CCCGCTGCTGGACAGGGGCTCGGCTGTTGGGCACTGACAATTCCGTGGT
```

In some embodiments, the polynucleotide or vector comprises a post-transcriptional regulatory element with a nucleotide sequence that has at least 75%, 80%, 85%, 90%, 95%, 96%, 97%, 98% or 99% identity to SEQ ID NO: 15 or 7, preferably SEQ ID NO: 15. Preferably, wherein the nucleotide sequence substantially retains the functional activity of the post-transcriptional regulatory element represented by SEQ ID NO: 15 or 7.

In other embodiments, the polynucleotide or vector comprises a post-transcriptional regulatory element with the nucleotide sequence of SEQ ID NO: 15 or 7, preferably SEQ ID NO: 15.

Another regulatory sequence which may be used in a polynucleotide or vector of the invention is a scaffold-attachment region (SAR). Additional regulatory sequences may be readily selected by the skilled person.

Method of Administration

The products, polynucleotide or vector of the invention may be administered systemically (for example by peripheral vein infusion) and may be administered locally or regionally (for example to the CNS system by intrathecal injection). In preferred embodiments, the product, polynucleotide or vector is administered intraocularly.

The term "intraocular" refers to the interior of the eye, thus intraocular administration relates to the administration to the interior of the eye of a subject In some embodiments, the product, polynucleotide or vector is administered to the eye of a subject by subretinal, direct retinal, suprachoroidal or intravitreal injection. In some embodiments, said administration is performed by a robot.

The volume of the medicament composition injected may, for example, be about 10-500 μL, for example about 50-500, 100-500, 200-500, 300-500, 400-500, 50-250, 100-250, 200-250 or 50-150 μL. The volume may, for example, be about 10, 50, 100, 150, 200, 250, 300, 350, 400, 450 or 500 μL. Preferably, the volume of the medicament composition injected is 100 UL.

The skilled person will be familiar with and well able to carry out individual subretinal, direct retinal, suprachoroidal or intravitreal injections.

Preferably, the product, polynucleotide or vector is administered by subretinal injection.

In some embodiments, the product, polynucleotide, vector or pharmaceutical composition comprising the same is administered not more than once, or not more than twice, during the lifetime of a subject.

Subretinal Injection

Subretinal injections are injections into the subretinal space, i.e. underneath the neurosensory retina. During a subretinal injection, the injected material is directed into, and creates a space between, the photoreceptor cell and retinal pigment epithelial (RPE) layers.

When the injection is carried out through a small retinotomy, a retinal detachment may be created. The detached, raised layer of the retina that is generated by the injected material is referred to as a "bleb".

The hole created by the subretinal injection must be sufficiently small that the injected solution does not significantly reflux back into the vitreous cavity after administration. Such reflux would be particularly problematic when a medicament is injected, because the effects of the medicament would be directed away from the target zone. Preferably, the injection creates a self-sealing entry point in the neurosensory retina, i.e. once the injection needle is removed, the hole created by the needle reseals such that very little or substantially no injected material is released through the hole.

To facilitate this process, specialist subretinal injection needles are commercially available (e.g. DORC 41G Teflon subretinal injection needle, Dutch Ophthalmic Research Center International BV, Zuidland, The Netherlands). These are needles designed to carry out subretinal injections.

Unless damage to the retina occurs during the injection, and as long as a sufficiently small needle is used, substantially all injected material remains localised between the detached neurosensory retina and the RPE at the site of the localised retinal detachment (i.e. does not reflux into the vitreous cavity). Indeed, the typical persistence of the bleb over a short time frame indicates that there is usually little escape of the injected material into the vitreous. The bleb may dissipate over a longer time frame as the injected material is absorbed.

Visualisations of the eye, in particular the retina, for example using optical coherence tomography, may be made pre-operatively.

The volume of the medicament composition injected may, for example, be about 10-500 μL, for example about 50-500, 100-500, 200-500, 300-500, 400-500, 50-250, 100-250, 200-250 or 50-150 μL. The volume may, for example, be about 10, 50, 100, 150, 200, 250, 300, 350, 400, 450 or 500 μL. Preferably, the volume of the medicament composition injected is 100 μL. Larger volumes may increase the risk of stretching the retina, while smaller volumes may be difficult to see.

Two-Step Subretinal Injection

The product, polynucleotide or vector of the invention may be delivered with increased accuracy and safety by using a two-step method in which a localised retinal detachment is created by the subretinal injection of a first solution. The first solution does not comprise the product, polynucleotide or vector. A second subretinal injection is then used to deliver the medicament comprising the product, polynucleotide or vector into the subretinal fluid of the bleb created by the first subretinal injection. Because the injection delivering the medicament is not being used to detach the retina, a specific volume of solution may be injected in this second step.

In some embodiments, the subretinal injection of the vector comprises the steps:

(a) administering a solution to the subject by subretinal injection in an amount effective to at least partially detach the retina to form a subretinal bleb, wherein the solution does not comprise the product, polynucleotide or vector; and (b) administering a medicament composition by subretinal injection into the bleb formed by step (a), wherein the medicament comprises the product, polynucleotide or vector.

The volume of solution injected in step (a) to at least partially detach the retina may be, for example, about 10-1000 μL, for example about 50-1000, 100-1000, 250-1000, 500-1000, 10-500, 50-500, 100-500, 250-500 μL. The volume may be, for example, about 10, 50, 100, 200, 300, 400, 500, 600, 700, 800, 900 or 1000 μL.

The volume of the medicament composition injected in step (b) may be, for example, about 10-500 μL, for example about 50-500, 100-500, 200-500, 300-500, 400-500, 50-250, 100-250, 200-250 or 50-150 μL. The volume may be, for example, about 10, 50, 100, 150, 200, 250, 300, 350, 400, 450 or 500 μL. Preferably, the volume of the medicament composition injected in step (b) is 100 μL. Larger volumes may increase the risk of stretching the retina, while smaller volumes may be difficult to see.

The solution that does not comprise the medicament (i.e. the "solution" of step (a)) may be similarly formulated to the solution that does comprise the medicament, as described below.

A preferred solution that does not comprise the medicament is balanced saline solution (BSS) or a similar buffer solution matched to the pH and osmolality of the subretinal space.

Visualising the Retina During Surgery

Under certain circumstances, for example during end-stage retinal degenerations, identifying the retina is difficult because it is thin, transparent and difficult to see against the disrupted and heavily pigmented epithelium on which it sits. The use of a blue vital dye (e.g. Brilliant Peel®, Geuder; MembraneBlue-Dual®, Dorc) may facilitate the identification of the retinal hole made for the retinal detachment procedure (i.e. step (a) in the two-step subretinal injection method of the invention) so that the medicament can be administered through the same hole without the risk of reflux back into the vitreous cavity.

The use of the blue vital dye also identifies any regions of the retina where there is a thickened internal limiting membrane or epiretinal membrane, as injection through either of these structures would hinder clean access into the subretinal space. Furthermore, contraction of either of these structures in the immediate post-operative period could lead to stretching of the retinal entry hole, which could lead to reflux of the medicament into the vitreous cavity.

Suprachoroidal Injection

The product, polynucleotide or vector of the invention may be delivered to the suprachoroidal space using an ab externo approach that utilises an microcatheter (see, for example, Peden et al. (2011) PLOS One 6 (2): e17140). In this method a limbal conjunctival peritomy is performed to expose bare sclera, followed by sclerotomy to expose bare choroid. A microcatheter (such as the iTrack 250A from iScience Interventional, optionally connected to an illumination system such as the iLumin laser-diode based micro-illumination system (iScience Interventional)) is introduced into the suprachoroidal space and advanced posteriorly towards the optic disc. Following manipulation of the microcatheter tip into the desired position, injection of the product, polynucleotide or vector forms a bleb within the retina and choroid.

Thus, in some embodiments, the product, polynucleotide or vector is delivered suprachoroidally by a method comprising (i) introduction of a microcatheter into the suprachoroidal space; (ii) advancing the microcatheter within said space until the tip is in the proximity of the afflicted region of the retina; and (iii) injecting the product, polynucleotide or vector from the microcatheter tip to create a bleb.

In some embodiments, the above administration procedures are directly carried out by a robot.

Pharmaceutical Compositions and Injected Solutions

The medicaments, for example products, polynucleotides or vectors, of the invention may be formulated into pharmaceutical compositions. These compositions may comprise, in addition to the medicament, a pharmaceutically acceptable carrier, diluent, excipient, buffer, stabiliser or other materials well known in the art. Such materials should be non-toxic and should not interfere with the efficacy of the active ingredient. The precise nature of the carrier or other material may be determined by the skilled person according to the route of administration, e.g. subretinal, direct retinal, suprachoroidal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution, or glycols such as ethylene glycol, propylene glycol or polyethylene glycol may be included. In some cases, a surfactant, such as pluronic acid (PF68) 0.001% may be used.

For injection at the site of affliction, the active ingredient may be in the form of an aqueous solution which is pyrogen-free, and has suitable pH, isotonicity and stability. The skilled person is well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included as required.

For delayed release, the medicament may be included in a pharmaceutical composition which is formulated for slow release, such as in microcapsules formed from biocompatible polymers or in liposomal carrier systems according to methods known in the art.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

The treatment of mammals, particularly humans, is preferred. However, both human and veterinary treatments are within the scope of the invention.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid-Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of full length Complement Factor I or Complement Factor I (CFI) cofactor, such as Complement Factor H or FHL1 are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Cofactor Assay

Recombinant Complement Factor I (CFI), cofactor (Complement Factor H (CFH) or Complement Factor H-like Protein 1 (FHL1)) and C3b were incubated together for 20 min at 37° C.

Concentrations of CFI and C3b were fixed, and titrations of CFH or FHL1 in specified ratios were carried out.

The cleavage of C3b to iC3b was quantified by ELISA.

Figure 2:
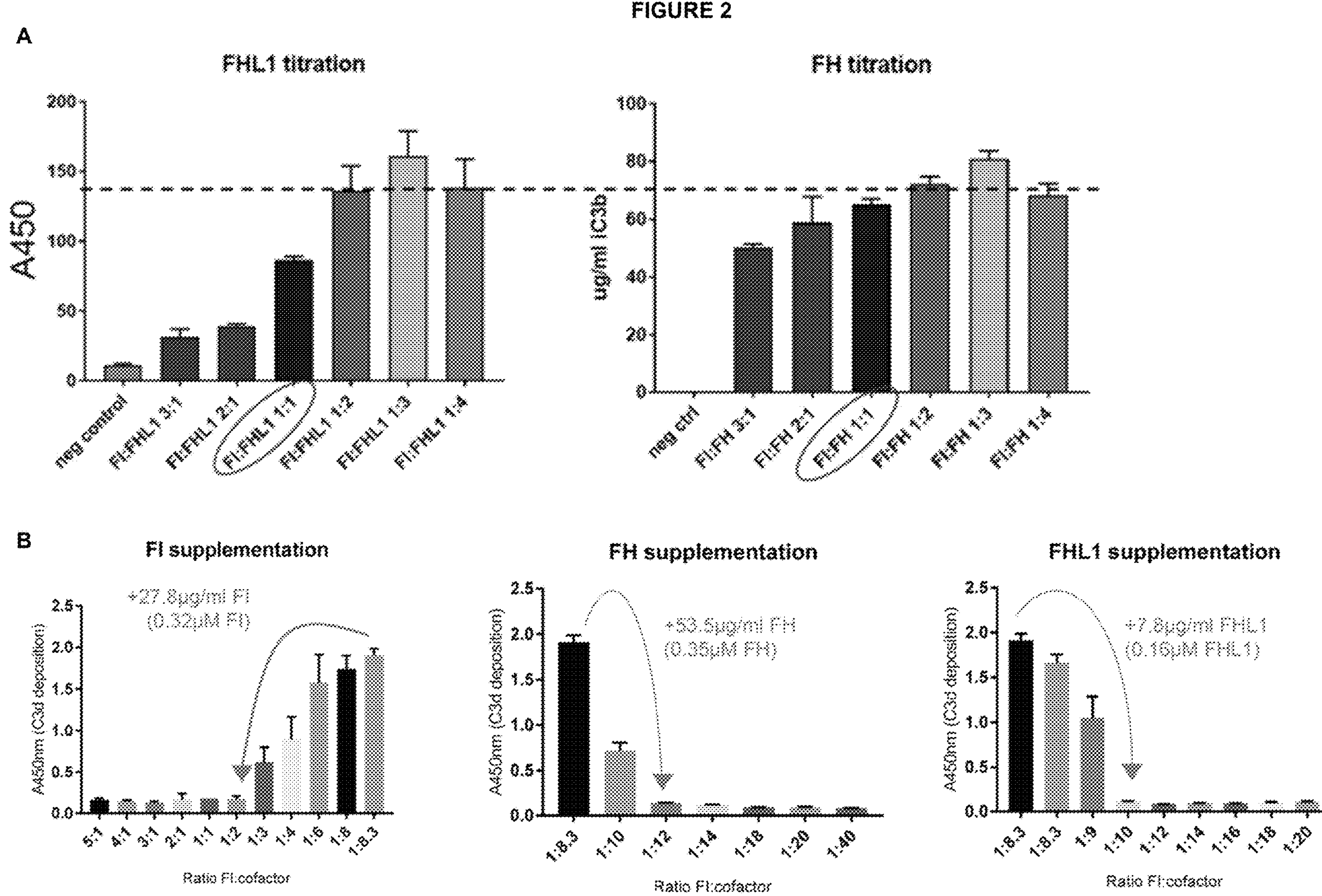

The results of these studies are shown in FIG. 2A.

From these results, it may be concluded that a minimum functional CFI: CFH/FHL1 molar ratio is 1:2.

Measurement of Normal Serum CFI: Cofactor Ratios

Complement Factor I (CFI), Complement Factor H (CFH) and Complement Factor H-like Protein 1 (FHL1) concentrations were measured in normal human serum using ELISAs.

The molar ratio of CFI: cofactor in normal serum was found to be 1:8.3.

Comparison of Plasma and Ocular Fluid CFI: Cofactor Ratios

Figure 7:
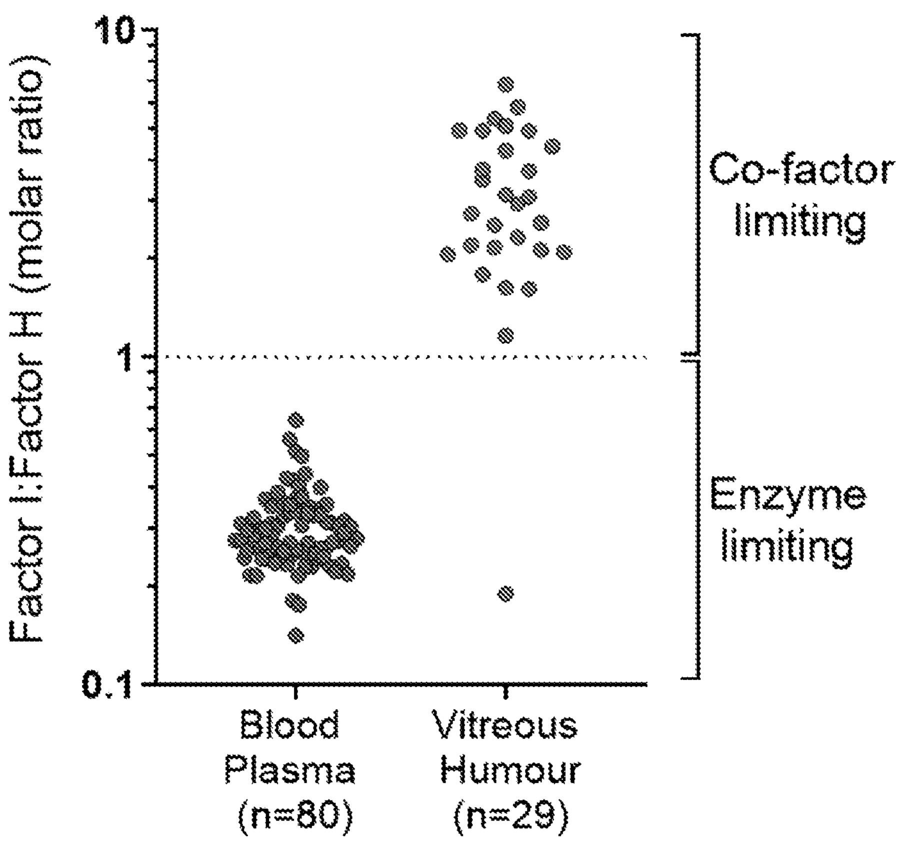

We subsequently compared the levels of CFI and CFH in both blood plasma and ocular fluids. Data showed that in contrast to plasma, in which the cofactor exists in several fold molar excess to CFI enzyme, this ratio is reversed in vitreous and aqueous humor (FIG. 7).

Complement Deposition Assay on Lipopolysaccharide (LPS)

A microtitre plate was coated with 1 μg/well of LPS and incubated overnight at 4° C.

The plate was then washed and incubated for 1 h at 37° C. with normal human serum supplemented with differing amounts of recombinant Complement Factor I (CFI), Complement Factor H (CFH) or Complement Factor H-like Protein 1 (FHL1). The plate was subsequently washed thoroughly, and complement deposition was measured with a mouse anti-C3d antibody (Abcam) and donkey anti-mouse (Jackson ImmunoResearch) used as a secondary antibody.

FIG. 2B shows the effect of CFI, CFH and FHL1 supplementation on complement deposition on LPS.

The x-axes show the ratio of Complement Factor I (CFI) to Complement Factor H+Complement Factor H like 1 (CFH and FHL1, the "cofactors"). Changes in the ratio were achieved solely by addition of recombinant CFI, CFH or FHL1.

Although the starting molar ratio of 1:8.3 (the natural ratio in normal serum) already has excess cofactor compared to enzyme, a further benefit on reduction of complement deposition and therefore activation is achieved when the ratio is further raised. This additional benefit may be related to an additional function (decay-accelerating activity, DAA) of the CFH and FHL1. Both CFH and FHL1 have DAA in that they compete with Complement Factor B (FB) for C3b binding, dislocate FB from C3b and thereby "decay" the alternative pathway convertase.

From these experiments, it is possible to conclude that below a minimum CFI: CFH/FHL1 molar ratio of 1:2, the cofactor becomes limiting.

Example 2

Generation of Bicistronic Plasmids

Recombinant AAV transgene plasmids (termed RC204, RC206-210 and RC212-218) were constructed comprising AAV2 5' and 3' inverted terminal repeats (ITRs) flanking the cassettes described in Table 1.

TABLE 1

| RC number | 5' ITR Adjacent Sequence | Promoter | Transgene #1 | Linker | Transgene #2 | WPRE | PolyA | 3' ITR Adjacent Sequence | Size (bp) |
|---|---|---|---|---|---|---|---|---|---|
| RC204 | Yes | CMV | CFI | IRES-CC | FHL-1 | No | BGHpA | Yes | 4882 |
| RC206 | | | CFI-CO | IRES-CC | FHL-1-CO | No | | | 4882 |
| RC207 | | | CFI | IRES-PV | FHL-1 | No | | | 5069 |
| RC208 | | | CFI-CO | IRES-PV | FHL-1-CO | No | | | 5069 |
| RC209 | | | FHL-1 | Furin-F2A | CFI | Standard | | | 5052 |
| RC210 | | | FHL-1-CO | Furin-F2A | CFI-CO | Standard | | | 5052 |
| RC212 | | | FHL-1-CO | Furin-F2A | CFI-CO | 3 | | | 4674 |
| RC213 | No | | CFI | IRES-CC | FHL-1 | No | | No | 4744 |
| RC214 | | | CF | IRES-PV | FHL-1 | No | | | 4929 |
| RC215 | | | FHL-1 | Furin-F2A | CFI | Standard | | | 4912 |
| RC216 | | | FHL-1-CO | Furin-F2A | CFI-CO | Standard | | | 4912 |
| RC217 | | | FHL-1 | Furin-F2A | CFI | 3 | | | 4548 |
| RC218 | | | FHL-1-CO | Furin-F2A | CFI-CO | 3 | | | 4548 |

The 5' ITR adjacent sequence used was SEQ ID NO: 20.

The CMV promoter sequence used was SEQ ID NO: 13.

The FHL1 sequence used was SEQ ID NO: 16. The codon optimised FHL1 (FHL1-CO) sequence used was SEQ ID NO: 12.

The Furin-F2A linker sequence used was SEQ ID NO: 17.

The CFI sequence used was SEQ ID NO: 2. The codon optimised CFI (CFI-CO) sequence used was SEQ ID NO: 10.

The WPRE3 sequence used was SEQ ID NO: 15.

The Bovine growth hormone poly-A (BGHpA) sequence used was SEQ ID NO: 14.

The 3' ITR adjacent sequence used was SEQ ID NO: 21.

The overall sequences of RC212 and RC218 are SEQ ID NOs: 22 and 23, respectively.

Comparison of Vectors by Transduction

Vector Production in Adherent HEK293

Separate transfection HEK293 cells with 12 plasmids (RC204, RC206-210 and RC212-217) was carried out using the following protocol:

Day 1: HEK293 cells were dissociated and counted using a ViCell. Cells were seeded in 10 cm plates at $6\times10^5$ cells per $cm^2$ in 10 mL DMEM/Glutamax+10% FBS per plate.

Day 2: Confluency was checked and was found to be between 70-80%.

Media was replaced with DMEM/Glutamax+5% FBS

After 4 hours, cells were transfected with 5 μg total plasmid DNA (1.25 μg construct DNA, 1.25 μg RepCap plasmid, 2.5 μg Helper plasmid) per plate using PEI at a 1:3 DNA:PEI ratio in duplicates:

1. 2×5 μg DNA was diluted in 2×1 mL PBS.

2. 2×15 UL PEI was added and incubated for 20 min.

3. 1 mL of DNA/PEI was added dropwise to the cells.

Day 3:15 mM of sodium butyrate was added.

Day 5: Media were harvested by pooling the duplicates, and centrifuged at 1000 rpm for 10 minutes to remove cell debris.

The supernatant was transferred to a new tube and AAVanced (AAV110A-1, Cambridge Bioscience) was added at 1/5 of the volume.

The mixture was incubated at 4° C. for 72 h.

Day 5: The mixture was centrifuged at 1000 rpm for 30 minutes at 4° C. Subsequently the supernatant was discarded, and the pellet was resuspended in 500 μL of PBS. The pellet was centrifuged for 3 minutes at 1500 g and then the supernatant was discarded again. The pellet was resuspended in 1/100 of the original supernatant volume and stored at −80° C. until titration.

Transduction of HEK293 Cells Using Vectors

Separate transduction of HEK293 cells with 12 viral vectors (RC204, RC206-210 and RC212-217) was carried out using the following protocol:

Day 1: HEK293 cells were dissociated and counted using a ViCell. Cells were seeded in 24 well plates at $1\times10^5$ cells in 400 μL DMEM/Glutamax+10% FBS per well.

Day 2: The required amount of viral vector was added to achieve a multiplicity of infection (MOI) of $2\times10^2$.

Day 3: Media were removed and replaced with 300 μL of serum free DMEM/Glutamax.

Day 5: The supernatant was harvested and centrifuged at 14000 rpm at 4° C. The clarified supernatant was transferred in new tubes ready for analysis.

Western Blot

Supernatants from the transduction were analysed by Western blot (primary antibodies to CFI and FHL-1; and ECL Prime Western blotting detection reagents were used).

Figure 3:
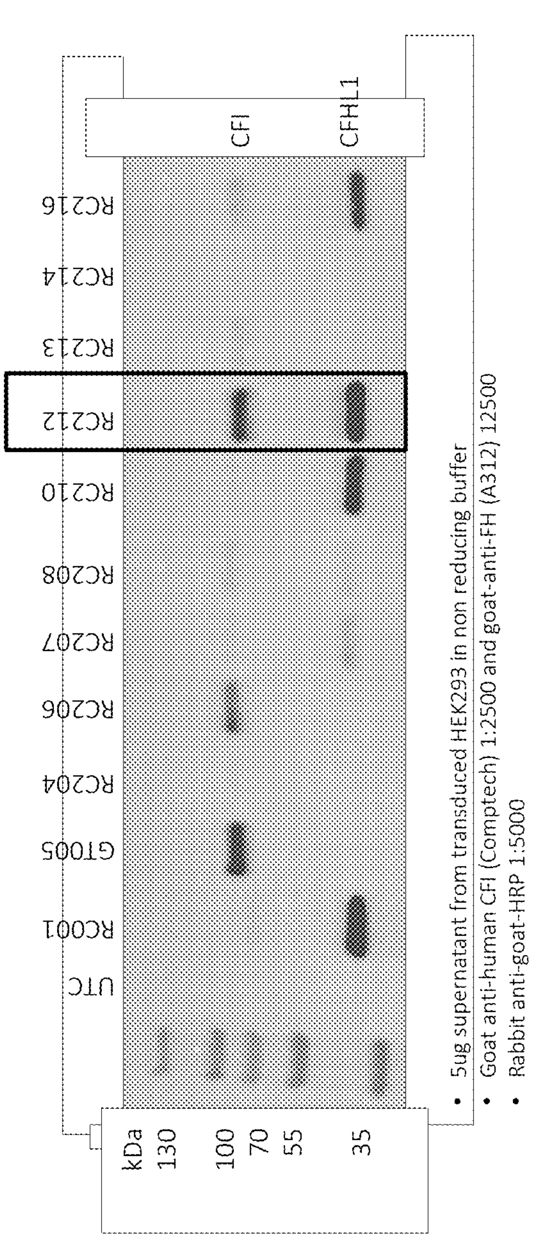

The Western blot analyses are shown in FIG. 3.

CFI ELISA

Supernatants from the transduction were analysed by ELISA for CFI using the following procedure:

Day 1: An ELISA plate was coated with 50 μL per well sheep anti-CFI polyclonal antibody diluted 1 in 4000 in 1× coating buffer. Plates were stored at 4° C. overnight.

Day 2: The plate was washed 3 times with 200 μL per well PBS-Tween (0.05%) then blotted on a tissue.

200 μL 1% BSA fraction V in PBS-Tween (0.05%) was applied to each well and allowed to block for 2 hours at room temperature.

Samples and standard curves were prepared during the blocking incubation. A standard curve was prepared using purified CFI protein (Sigma C5938-1 MG) diluted in DMEM 2% FBS. Samples were diluted 1:5 and 1:10 in DMEM 2% FBS.

After 2 hours blocking, the plate was washed 3 times, as described above, then 50 μL sample or standard was loaded onto each well and incubated at room temperature for 1 hour.

After 1 hour, the plate was washed as above, then anti-CFI (Ox21) antibody was diluted 1 in 2000 in DMEM 5% FBS and 50 μL of this was applied to each well and incubated at room temperature for 1 hour.

After 1 hour, the plate was washed as above then donkey anti-mouse-HRP antibody was diluted 1 in 5000 in DMEM 5% FBS and 50 μL of this was applied to each well and incubated at room temperature for 1 hour.

After 1 hour, the plate was washed as above, then 100 μL TMB reagent was applied to each well and incubated at room temperature in the dark for approximately 15 minutes. Once sufficient blue colour had been obtained, 100 μL 1 M sulphuric acid was added to each well to stop the reaction.

The A450 was then recorded with and data were processed and transferred to Microsoft Excel for analysis.

FHL1 ELISA

Supernatants from the transfection were analysed by ELISA for FHL1 using the following procedure:

Day 1: An ELISA plate was coated with 50 μL per well, 3 μg/mL anti-FHL-1 antibody (Biorad, AbD33594.1) in 100 mM Carbonate/Bicarbonate Buffer, pH 9.6. Plates stored at 4° C. overnight.

Day 2: The plate was washed 3 times with 200 μL per well TBS-Tween (0.05%) then blotted on a tissue.

200 μL 1% BSA fraction V in PBS-Tween (0.05%) was applied to each well and allowed to block for 2 hours at room temperature.

Samples and standard curves were prepared during the blocking incubation. A standard curve was prepared using FHL1 purified protein diluted in DMEM 2% FBS. Samples were diluted 1:5 and 1:10 in blocking buffer.

After 2 hours blocking, the plate was washed 3 times, as described above, then 50 μL sample or standard was loaded onto each well and incubated at room temperature for 1 hour.

After 1 hour, the plate was washed as above, then anti-CFH antibody (Ox24, Santa Cruz Biotechnologies, sc-53067) was added at 0.33 μg/mL in blocking buffer and 50 μL of this was applied to each well and incubated at room temperature for 1 hour.

After 1 hour, the plate was washed as above then donkey anti-mouse-HRP antibody was added at 0.2 μg/mL in blocking buffer and 50 μL of this was applied to each well and incubated at room temperature for 1 hour.

After 1 hour, the plate was washed as above, then 100 μL TMB reagent was applied to each well and incubated at room temperature in the dark for approximately 15 minutes. Once sufficient blue colour had been obtained, 50 μL 1 M sulphuric acid was added to each well to stop the reaction.

The A450 was then recorded with and data were processed and transferred to Microsoft Excel for analysis.

Conclusions

Figure 4:
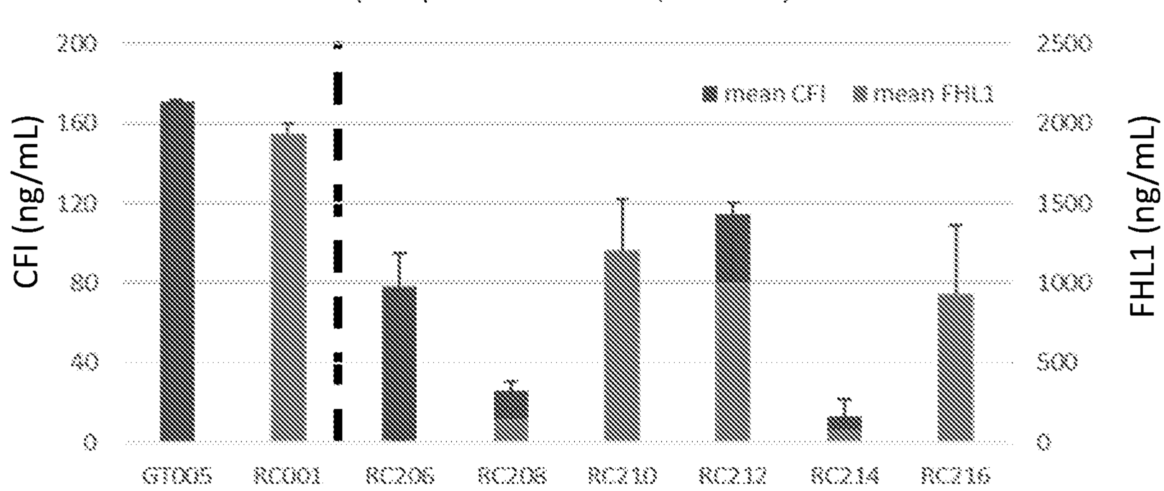
Figure 4:
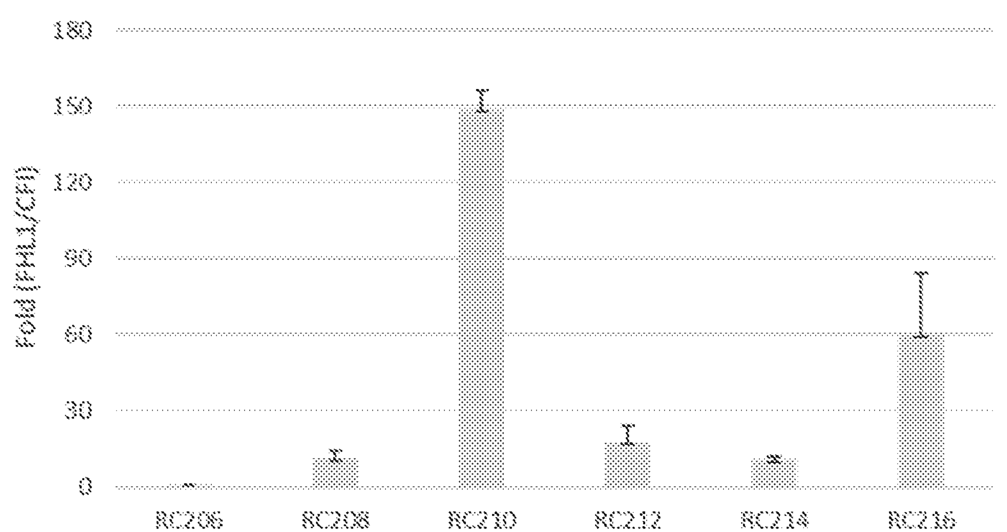

The results of the Western blot and ELISA studies are shown in FIGS. 3 and 4, respectively.

From the Western blot and ELISA analyses, it may be concluded that:

All candidates produce both CFI and FHL1 after transduction.

CFI and FHL1 codon optimisation increases protein levels.

RC206 and RC212 are optimal for CFI expression, however RC212 achieves optimal CFI: FHL1 molar ratio (>1:2).

RC212 is the best candidate based on CFI/FHL1 expression.

Vector Packaging

Alkaline Gel Analysis 24 μL of each undiluted sample and SRM control ($2.45\times10^{11}$ vg/mL; SRM #16-048) were loaded onto a 0.8% alkaline gel, which was then run for 19 hours at 20 V in a cold room in alkaline running buffer (40 ml 50× alkaline buffer+1960 mL MilliQ water).

The gel was then incubated in 3 gel vols of 0.1 M Tris pH 8.0 for 1 h at room temperature, then in 1 gel volume 0.1 M NaCl containing 4× SYBRGold nucleic acid stain for 2 h at room temperature (protected from light exposure), then rinsed twice in MilliQ water.

The gel was then visualised using SYBRGold UV transilluminator setting on a Chemidoc at 10 seconds exposure time.

Figure 5:
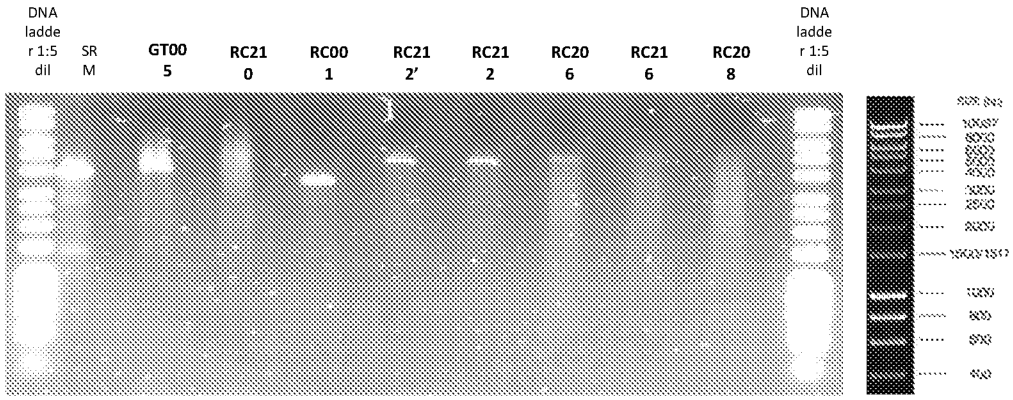
Figure 5:
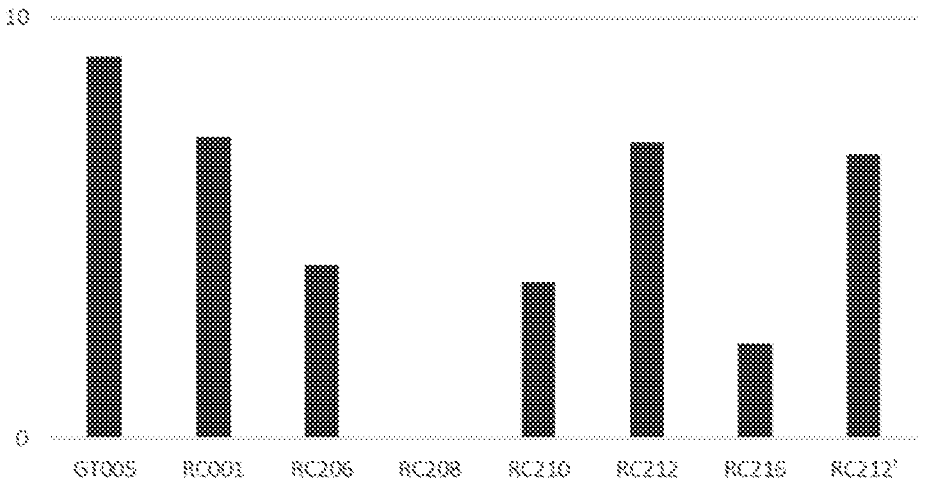

The result is shown in FIG. 5 (top panel).

Full: Empty Particle Ratio

The ratio of full to empty viral particles was analysed by comparing titres as calculated from qPCR (DNA titre) and capsid ELISA.

The result is shown in FIG. 5 (bottom panel).

Conclusions

From these analyses it may be concluded that:

Efficient packaging only with RC212.

There appears to be incomplete packaging of genomes>4.7 kb.

Full-empty particle ratio of RC212 is comparable to the control monocistronic vectors.

RC212 is the best candidate based on packaging analysis.

C3b Cleavage Assay

In the C3b cleavage assay, 1 mg of plasma purified C3b is incubated for 1 hour at 37° C. with transduced HEK293 supernatant samples.

Analyses were carried out using ELISA, or Western blot analysis (described as follows). 4× Laemmli buffer with β-mercaptoethanol was added to stop the reaction. Samples were diluted and loaded on a 10% precast polyacrylamide SDS PAGE gel (Bio-Rad). After transfer to a PVDF membrane (Bio-Rad) and blocking in blocking buffer (1×TBS pH 8 [Sigma]/0.05% Tween-20 and 5% dried skimmed milk powder [Marvel]), C3b cleavage was detected using goat anti-human C3 antibody (Biorad).

Figure 6:
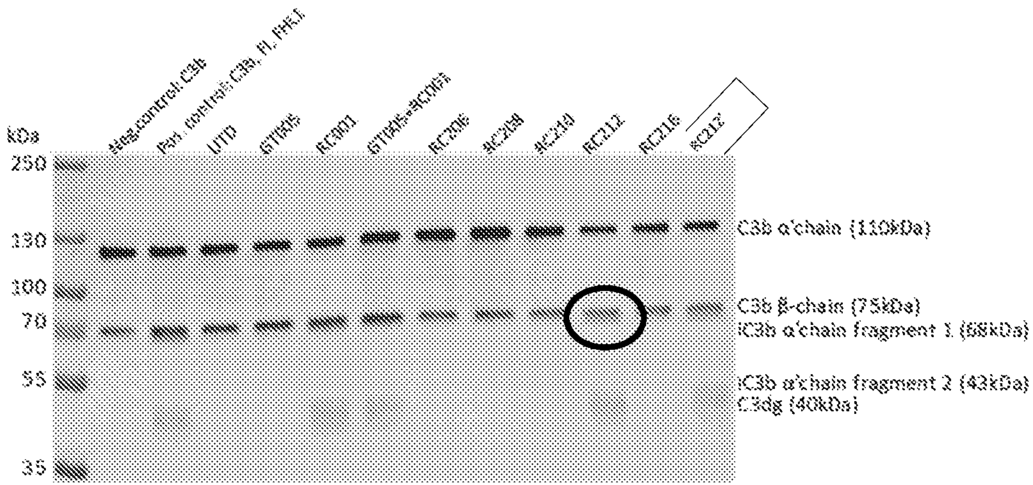
Figure 6:
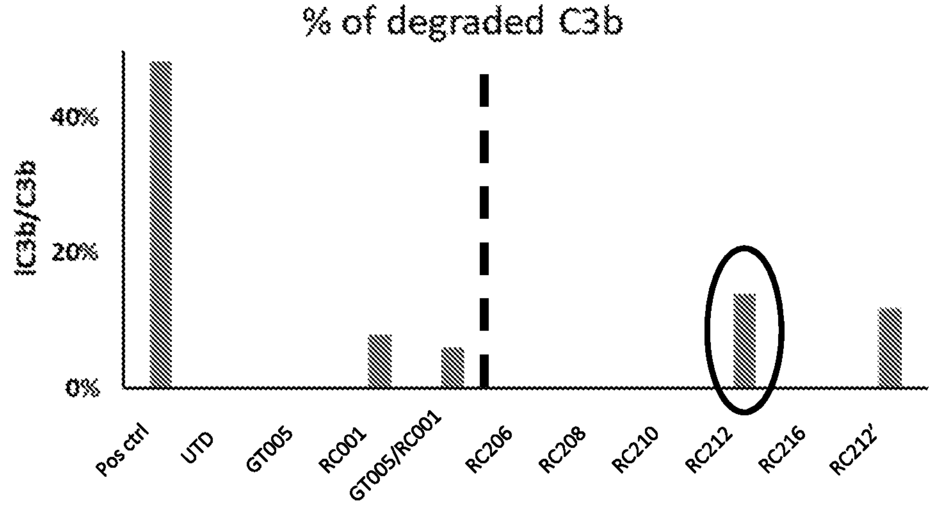

The results are shown in FIG. 6, form which is it possible to conclude that RC212 is the most potent.

Example 3—Additional Complement Down-Regulation on Addition of Multiple Complement Regulators Methods To measure functional activity of complement regulators, an LPS deposition assay was performed. Nunc Maxisorb plates were coated overnight at 4° C. with 1 μg/mL LPS (Sigma, *Escherichia coli* O26: B6) in diluted ELISA Coating Buffer (BioRad, BUF030B). Plates were washed with PBS-0.05% Tween 20. 25% Serum in alternative pathway buffer (PBS, 2 mM MgCl2 and 10 mM EGTA, pH 7.2) was prepared and supplemented with complement regulators. Dilutions were added to the LPS-coated plate and incubated for 1 hour at 37° C. 10 mM EDTA was added to a separate tube with serum to prevent complement activation and this sample was used to determine background signal in the assay. The plate was washed as before and complement activation measured by detecting C3 deposition on the plate (goat anti-C3d Abcam, ab17453; 1:20,000). After 1 hour incubation at ambient temperature, plates were washed and incubated for another hour with donkey anti-mouse HRP conjugated antibody (Jackson Immunoresearch, 715-035-150; 1:1,000). After four washes, the plates were incubated with 1-Step Ultra TMB-ELISA Substrate (Life Technologies) and the reaction was quenched with 1 M $H_2SO_4$. The OD at 450 nm was measured using a Varioskan plate reader (Thermo Fisher) and the IC50 was determined from 4PL fitted curves using GraphPad Prism. Complement preserved female human serum was used for these experiments.

Results

Figure 8:
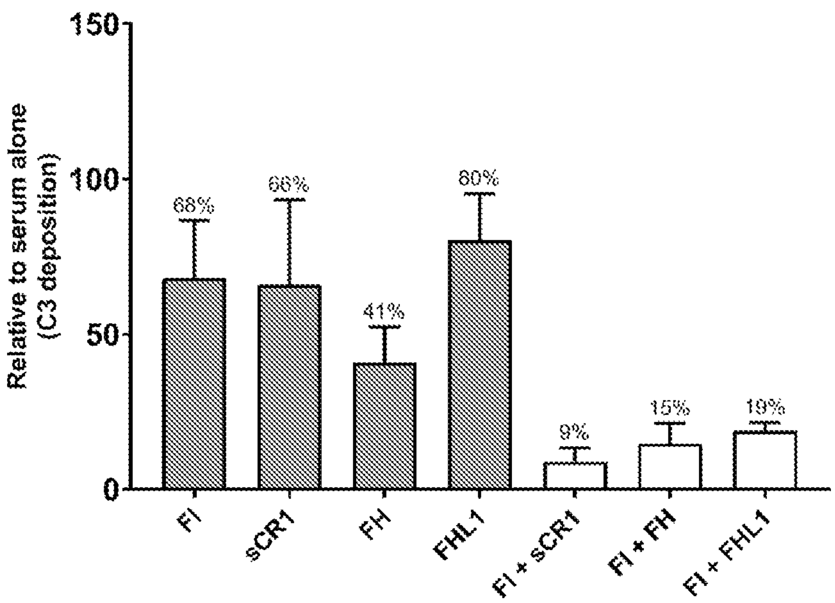

The IC50 concentration of complement regulator proteins, Complement Factor I, soluble complement receptor 1, Complement Factor H or Factor H-like 1, was determined in a separate experiment using the same assay platform. Here, results show (FIG. 8) that when the IC50 concentrations of regulator proteins is added, the alternative pathway (as measured by reduction of C3 deposition) is quenched (shaded columns). If Complement Factor I is co-supplemented with one of its cofactors (soluble complement receptor 1, complement Factor H or Factor H-like 1), additional quenching is observed (white columns), demonstrating that increasing the concentration of two complement regulators is superior to addition of either alone. These results indicate that conditions caused by an overreactive complement system might benefit from a dual administration of multiple complement regulators.

The IC50 concentrations of the individual regulators differ widely across the regulators tested (sCR1~10× more potent than FHL1 and ~50× more potent than CFH and CFI) but also in their molecular weight (sCR1=213 kDa, CFI=88 kDa, CFH=155 kDa and FHL1=49 kDa), molar concentrations were used for this direct comparison. Endogenous levels of proteins will also contribute to observed differences in potency; Factor H has a much higher plasma concentration than FHL1 or sCR1. By comparing the ability of regulators at their IC50 concentration to quench the alternative pathway, it was demonstrated that sCR1 is the most potent regulator because it requires the lowest molar concentration to achieve the IC50. Because CR1 is a membrane bound receptor on erythrocytes, which are abundant in blood but not serum/plasma, and only minute amounts of fluid CR1 (i.e. sCR1) are present in serum or plasma, this infers that sCR1 would be a very potent complement regulator and CFI cofactor at sites where erythrocytes are separated from plasma, such as the choroidal space, Bruch's membrane subretinal space and the glomerulus.

Example 4—Expression of Complement Factor I and Factor H-Like 1 In Vitro Expression Methods HEK-293 cells were transduced with one of the following rAAV vectors: AAV expressing CFI (GT005); AAV expressing FHL1 (RC001); or AAV expressing CFI and FHL1 (GT007). Supernatants were analysed by non-reducing western blot to determine relative protein expression. Goat anti human CFI (Comptech) and goat anti human FH (Quidel, A312) were used as primary antibodies to detect CFI and FHL1 protein.

Results

Figure 9:
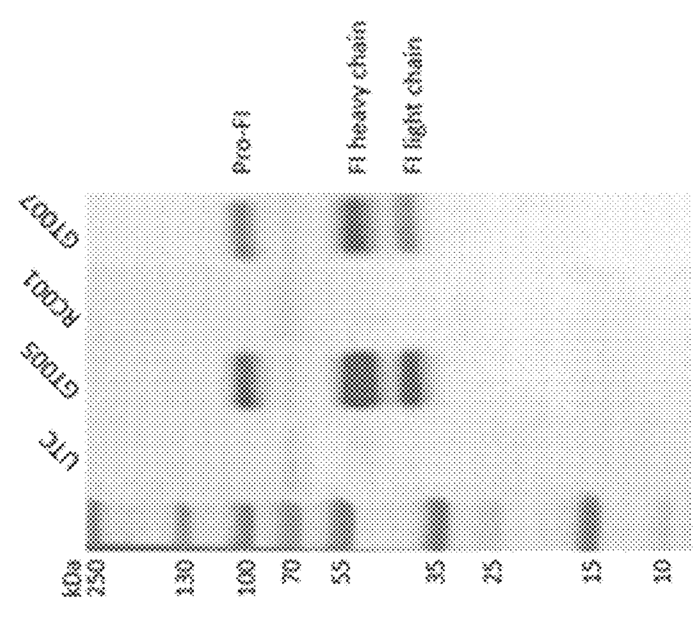
Figure 9:
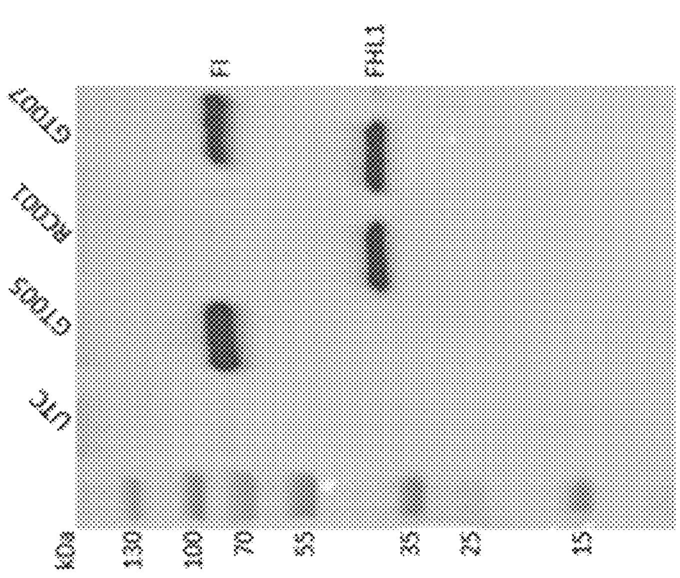

Western blot analysis showed that CFI and FHL1 protein were expressed and secreted into the culture medium from all three constructs (FIGS. 9A and B). To confirm this pattern of expression, supernatants were analysed by immunoblotting to visualise CFI protein to determine correct processing and secretion in the supernatant. As demonstrated in FIG. 9B, heavy and light chain CFI, as well as pro-CFI, are secreted from HEK-293 cells following transduction with GT007, confirming that CFI protein was translated, and that proteolytic processing has occurred. In mammalian cells transfected with plasmid encoding CFI cDNA, not all of the recombinant pro-CFI protein undergoes cleavage, resulting in secretion of pro-CFI (88 kDa) as well as the mature processed CFI, consisting of the 50 kDa heavy chain and the 38 kDa light chain.

Figure 10:
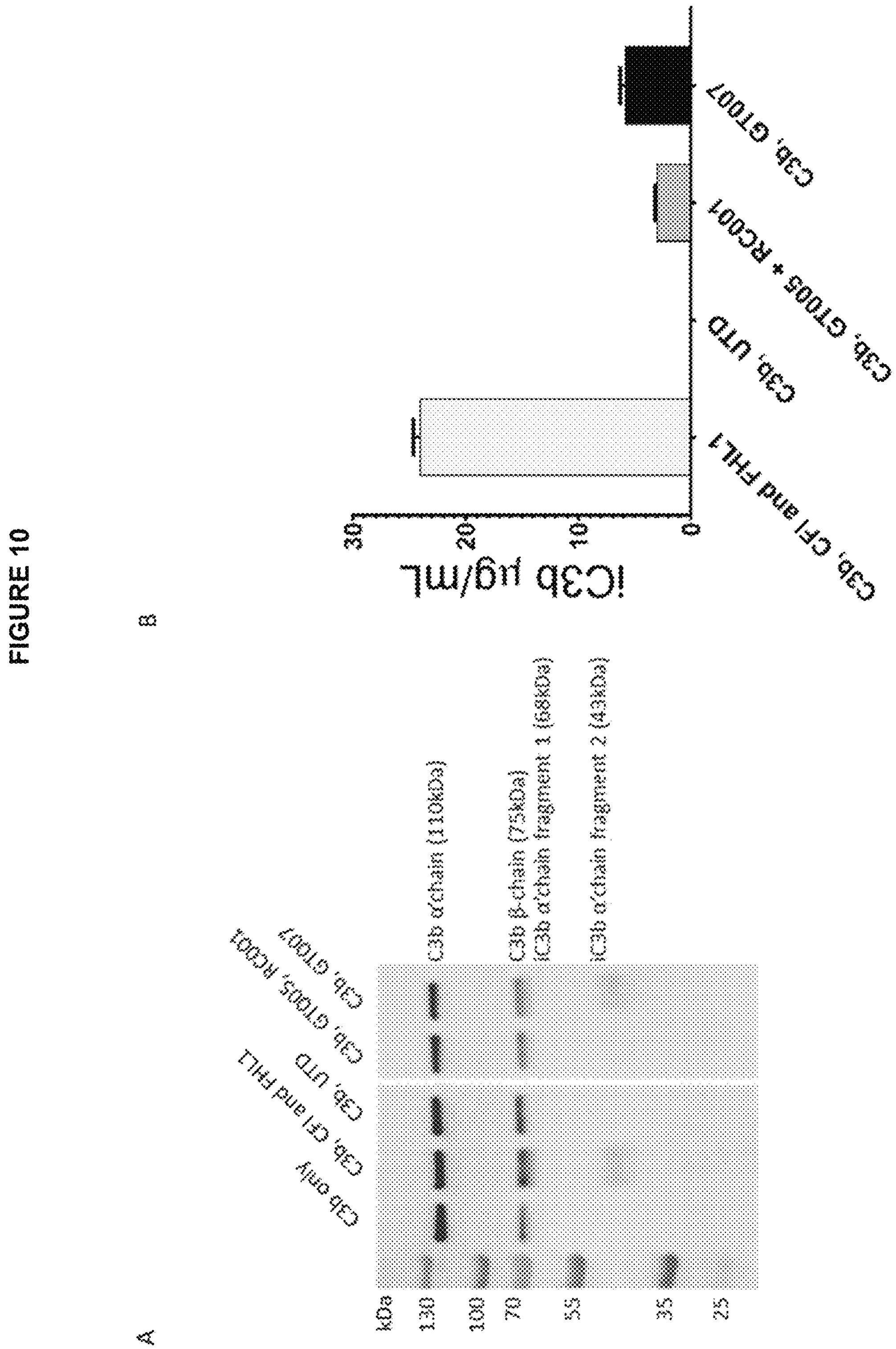
Figure 11:
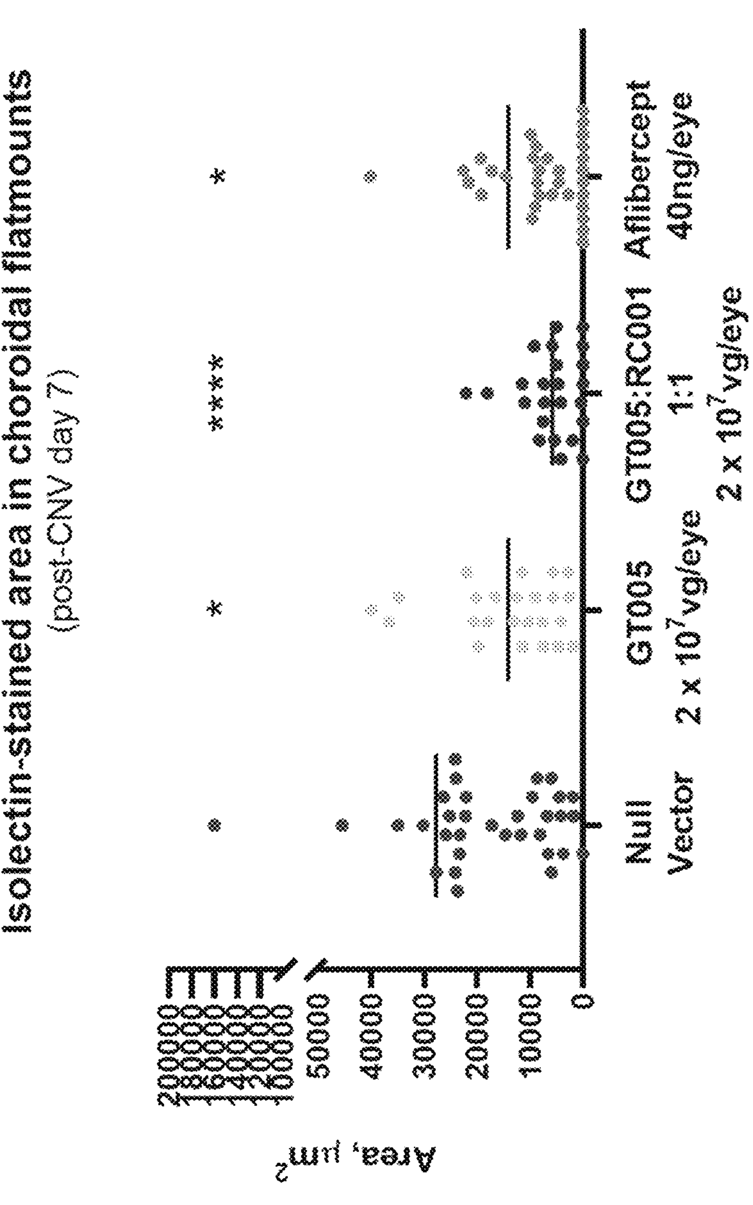

Example 5—Functionality of Complement Factor I and Factor H-Like 1 In Vitro Expression Methods To analyse functional activity of CFI and FHL1 secreted from transduced cells, conditioned supernatant from HEK-293 cells transduced with: AAV expressing CFI (GT005) alone; AAV2 expressing FHL1 (RC001) alone; co-transduced with both GT005 and RC001; or transduced with AAV expressing CFI and FHL1 (GT007) was tested in a C3b cleavage assay (FIG. 10). In this assay, C3b is mixed together with a source of CFI and FHL1 and incubated for 4 hours at 37° C. This incubation time was optimised for the concentrations of transgenes expressed from the transduced cells. The principle of this assay is based on the ability of CFI, in the presence of FHL1, to cleave C3b into iC3b and C3f. The assay is analysed by a C3b western blot, staining the C3b cleavage products, and by iC3b ELISA which quantifies the amount of the C3b breakdown product, iC3b.

Results

Results of both the C3 western blot and iC3b ELISA correlate and demonstrate functional activity of CFI and FHL1 expressed in vitro. In the C3b western blot (FIG. 10A), lane 1 shows C3b only, lane 2 shows C3b mixed with CFI and FHL1 (positive control) and lane 3 shows C3b mixed with conditioned supernatant from untransduced cells (UTD, negative control). Lane 4 shows C3b degradation when conditioned supernatant of cells co-transduced with GT005 (CFI) and RC001 (FHL1). Lane 5 shows conditioned supernatant of cells transduced with GT007 (expressing CFI and FHL1). The assay confirms that conditioned supernatant of GT007-transduced cells contains active CFI and FHL1 that degrade C3b into iC3b.

The iC3b ELISA (FIG. 10B) was performed using the same supernatant used for the C3b western blot and the amount of iC3b was quantified as a direct function of protein functionality. As before, C3b incubated with CFI and FHL1 acts as a positive control as does conditioned supernatant of GT005 and RC001 co-transduced cells. The supernatant of GT007-transduced cells shows C3b cleavage activity, confirming presence of active CFI and FHL1.

Example 6—In Vivo Efficacy in a Mouse Model of Choroidal Neovascularisation (CNV)

Methods

A laser-induced choroidal neovascularisation model was performed in mice. Mice (n=12-14 per group) received unilateral subretinal injections of AAV vectors 4 weeks prior to the CNV induction, or aflibercept (positive control) just after the CNV induction. The contralateral eye served as control. Mice were followed using in vivo imaging, fluorescein angiography (FA) and spectral-domain optical coherence tomography (SD-OCT), at days 4 and 7. At the end of the study period at the follow-up day 7 after the CNV induction, the mice were sacrificed by anaesthesia overdose, serum was collected and the eyes were enucleated. Neural retina was excised and fresh frozen in liquid nitrogen. Choroids were post-fixed and choroidal flatmounts were prepared. Histological analysis from choroidal flat mounts was used to quantify the area of isolectin B4 staining in the CNV lesions.

Results

The aflibercept group significantly affected the degree of CNV leakage compared to the Null vector control group at 4 days post-CNV induction ($P<0.0001$ compared to all other groups), but this was lost by Day 7, presumably due to drug washout over time. The area of CNV leakage was significantly decreased in aflibercept-treated eyes both at Day 4 ($P<0.0001$ for all group comparisons) and Day 7 ($P=0.019$ vs. null vector group).

Choroidal flat-mounts were co-stained with fluorescein-labelled isolectin. Isolectin B4 stains endothelial cells and is used to visualise CNV lesions. Data were non-normally distributed as assessed by Kolmogorov-Smirnov test ($P<0.05$) and therefore, statistical significance of the observed differences was determined using Generalized Linear Model (GLM) analysis. All treatment groups showed statistically significant reduction in the isolectin B4-stained area as compared to the null treatment group (GLM, $P<0.05$ for all). Co-administration of CFI and FHL1-expressing vectors (GT005: RC001) provided the most significant reduction.

All publications mentioned in the above specification are herein incorporated by reference. Various modifications and variations of the disclosed agents, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention is further described by the following numbered paragraphs:

1. A product comprising (i) Complement Factor H Like Protein 1 (FHL1) or Complement Factor H (CFH); and (ii) Complement Factor I (CFI), or nucleotide sequences encoding therefor, as a combined preparation for simultaneous, separate or sequential use in therapy.

2. A product comprising (i) Complement Factor H Like Protein 1 (FHL1) or Complement Factor H (CFH); and (ii) Complement Factor I (CFI), or nucleotide sequences encoding therefor, as a combined preparation for simultaneous, separate or sequential use in treating or preventing a complement-mediated disorder of the eye.

3. The product for use according to para 2, wherein the complement-mediated disorder is age-related macular degeneration (AMD) or diabetic retinopathy, preferably AMD.

4. The product for use according to para 3, wherein the AMD is dry AMD.

5. The product for use according to any preceding para, wherein the product provides (i) and (ii) to a subject in a (i): (ii) molar ratio of at least 2:1, preferably at least 3:1, more preferably at least 8:1, more preferably at least 15:1.

6. The product for use according to any preceding para, wherein the product provides (i) and (ii) to a subject in a (i): (ii) molar ratio of between 2:1 and 12:1, preferably between 3:1 and 10:1.

7. An isolated polynucleotide comprising nucleotide sequences encoding (i) Complement Factor H Like Protein 1 (FHL1) or Complement Factor H (CFH); and (ii) Complement Factor I (CFI).

8. The isolated polynucleotide of para 7, wherein the polynucleotide further comprises nucleotide sequences encoding:
- (a) a CMV promoter, optionally wherein the CMV promoter is upstream of the nucleotide sequences encoding the (i) and (ii);
- (b) a WPRE regulatory element, optionally wherein the WPRE regulatory element is downstream of the nucleotide sequences encoding the (i) and (ii); and/or
- (c) a poly-A signal, optionally a Bovine Growth Hormone poly-A signal, wherein the polyA signal is optionally downstream of the nucleotide sequences encoding the (i) and (ii).

9. The isolated polynucleotide of para 7 or 8, wherein the nucleotide sequence encoding (i) is upstream of the nucleotide sequence encoding (ii).

10. The isolated polynucleotide of any one of paras 7-9, wherein the polynucleotide further comprises one or more adeno-associated virus (AAV) inverted terminal repeats (ITRs).

11. The isolated polynucleotide of any one of paras 7-10, wherein the polynucleotide comprises an AAV ITR at its 5' end and an AAV ITR at its 3' end.

12. The isolated polynucleotide of any one of paras 7-11, wherein the polynucleotide comprises:
- (a) a 5' AAV ITR;
- (b) a CMV promoter;
- (c) a nucleotide sequence encoding FHL1 or CFH, preferably FHL1;
- (d) a linker, optionally wherein the linker is comprises or is defined by a Furin cleavage site, GSG, 11aa1D sequence and an F2A sequence;
- (e) a nucleotide sequence encoding CFI;
- (f) a WPRE regulatory element, optionally wherein the WPRE regulatory element is a WPRE3 regulatory element;
- (g) a Bovine Growth Hormone poly-A signal; and
- (h) a 3' AAV ITR.

13. The isolated polynucleotide of any one of paras 7-12, wherein the AAV ITRs are AAV2 or AAV8 ITRs.

14. The isolated polynucleotide of any one of paras 7-13, wherein the nucleotide sequences encoding FHL1 or CFH, and CFI are codon optimised.

15. The isolated polynucleotide of any one of paras 7-14, wherein: (a) the nucleotide sequence encoding FHL1 has at least 75% sequence identity to SEQ ID NO: 12; and/or (b) the nucleotide sequence encoding CFI has at least 75% sequence identity to SEQ ID NO: 10.

16. The isolated polynucleotide of any one of paras 7-15, wherein: (a) the nucleotide sequence encoding FHL1 is SEQ ID NO: 12; and/or (b) the nucleotide sequence encoding CFI is SEQ ID NO: 10.

17. The isolated polynucleotide of any one of paras 7-16, wherein the polynucleotide comprises the nucleotide sequence of SEQ ID NO: 22 or 23, or a nucleotide sequence that has at least 75% sequence identity thereto.

18. The isolated polynucleotide of any one of paras 7-17, wherein the polynucleotide is less than or equal to 4.7 kb.

19. A vector comprising the polynucleotide of any one of paras 7-18.

20 The vector of para 19, wherein the vector is an adeno-associated viral (AAV) vector.

21. The vector of para 19 or 20, wherein the vector is in the form of a viral vector particle.

22. The vector of para 21, wherein the AAV vector particle comprises an AAV2 or AAV8 genome, and AAV2 or AAV8 capsid proteins.

23. A cell comprising the polynucleotide of any one of paras 7-18.

24. A cell transduced with the vector of any one of paras 19-22.

25. A pharmaceutical composition comprising the polynucleotide, vector or cell of any one of paras 7-24 in combination with a pharmaceutically acceptable carrier, diluent or excipient.

26. The polynucleotide, vector or cell of any one of paras 7-24 for use in therapy.

27. The polynucleotide, vector or cell of any one of paras 7-24 for use in treating or preventing a complement-mediated disorder of the eye.

28. The polynucleotide, vector or cell for use according to para 27, wherein the complement-mediated disorder is age-related macular degeneration (AMD) or diabetic retinopathy, preferably AMD.

29. The polynucleotide, vector or cell for use according to para 28, wherein the AMD is dry AMD.

30. The polynucleotide, vector or cell for use according to any one of paras 26-29, wherein the formation of geographic atrophy is prevented or reduced, and/or the amount of geographic atrophy is reduced.

31. The polynucleotide, vector or cell for use according to any one of paras 26-30, wherein the progression of geographic atrophy is slowed.

32. The polynucleotide, vector or cell for use according to any one of paras 26-31, wherein there is at least a 10% reduction in the increase in geographic atrophy area over the 12 months following administration to a treated eye of a subject, relative to an untreated eye over the same period.

33. The polynucleotide, vector or cell for use according to any one of paras 26-32, wherein administration of the polynucleotide, vector or cell increases the level of C3b-inactivating and iC3b-degradation activity in a subject, or in an eye, such as in the retinal pigment epithelium (RPE), of a subject, optionally to a level that exceeds a normal level in a subject, or eye or RPE thereof.

34. The polynucleotide, vector or cell for use according to any one of paras 26-33, wherein the polynucleotide, vector or cell is administered intraocularly.

35. The polynucleotide, vector or cell for use according to any one of paras 26-34, wherein the polynucleotide, vector or cell is administered to the eye of a subject by subretinal, direct retinal, suprachoroidal or intravitreal injection.

36. The polynucleotide, vector or cell for use according to any one of paras 26-35, wherein the polynucleotide, vector or cell is administered to the eye of a subject by subretinal injection.

37. A method of treating or preventing a complement-mediated disorder of the eye comprising administering the polynucleotide, vector or cell of any one of paras 7-24 to a subject in need thereof.

38. A method of providing (i) Complement Factor H Like Protein 1 (FHL1) or Complement Factor H (CFH); and (ii) Complement Factor I (CFI) to a subject, comprising delivering the polynucleotide, vector or cell of any one of paras 7-24 to the eye of the subject.

The invention claimed is:

1. An isolated polynucleotide comprising nucleotide sequences encoding (i) a Complement Factor I (CFI) cofactor; and (ii) Complement Factor I (CFI), wherein the polynucleotide comprises:

a) a 5' AAV ITR;

b) a CMV promoter;

c) a codon-optimized nucleotide sequence encoding Complement Factor H Like Protein 1 (FHL1);

d) a linker comprising a self-cleaving 2A peptide sequence;

e) a codon-optimized nucleotide sequence encoding CFI;

f) a WPRE3 regulatory element;

g) a Bovine Growth Hormone poly-A signal; and h) a 3' AAV ITR;

wherein the polynucleotide comprises the nucleotide sequence of SEQ ID NO: 22 or 23, or a nucleotide sequence that has at least 95% sequence identity thereto.

2. The isolated polynucleotide of claim 1, wherein: (a) the nucleotide sequence encoding FHL1 is SEQ ID NO: 12; and/or (b) the nucleotide sequence encoding CFI is SEQ ID NO: 10.

3. The isolated polynucleotide of claim 1, wherein the polynucleotide comprises the nucleotide sequence of SEQ ID NO: 22 or 23.

4. The isolated polynucleotide of claim 1, wherein the polynucleotide is less than or equal to 4.7 kb.

5. A vector comprising the polynucleotide of claim 1.

6. The vector of claim 5, wherein the vector is an adeno-associated viral (AAV) vector.

7. The vector of claim 5, wherein the vector is in the form of a viral vector particle.

8. The vector of claim 7, wherein the AAV vector particle comprises AAV2 or AAV8 capsid proteins.

9. A cell comprising the polynucleotide of claim 1.

10. A cell transduced with the vector of claim 5.

11. A pharmaceutical composition comprising the polynucleotide of claim 1 in combination with a pharmaceutically acceptable carrier, diluent or excipient.

12. The isolated polynucleotide of claim 1, wherein: (a) the nucleotide sequence encoding FHL1 is SEQ ID NO: 12; and (b) the nucleotide sequence encoding CFI is SEQ ID NO: 10.

13. The isolated polynucleotide of claim 1, wherein the polynucleotide comprises the nucleotide sequence of SEQ ID NO: 22.

* * * * *

SEQUENCE LISTING

```
<160> NUMBER OF SEQ ID NOS: 27

<210> SEQ ID NO 1
<211> LENGTH: 583
<212> TYPE: PRT
<213> ORGANISM: Homo sapiens

<400> SEQUENCE: 1

Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Thr Gln Glu Glu Thr
    290                 295                 300

Glu Ile Leu Thr Ala Asp Met Asp Ala Glu Arg Arg Arg Ile Lys Ser
```

```
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
            420                 425                 430

Ile Glu Met Lys Lys Asp Gly Asn Lys Lys Asp Cys Glu Leu Pro Arg
        435                 440                 445

Ser Ile Pro Ala Cys Val Pro Trp Ser Pro Tyr Leu Phe Gln Pro Asn
    450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
            500                 505                 510

Thr Tyr Asp Gly Ser Ile Asp Ala Cys Lys Gly Asp Ser Gly Gly Pro
        515                 520                 525

Leu Val Cys Met Asp Ala Asn Asn Val Thr Tyr Val Trp Gly Val Val
    530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580
```

<210> SEQ ID NO 2
<211> LENGTH: 1752
<212> TYPE: DNA
<213> ORGANISM: Homo sapiens

<400> SEQUENCE: 2

```
atgaagcttc ttcatgtttt cctgttattt ctgtgcttcc acttaaggtt ttgcaaggtc     60

acttatacat ctcaagagga tctggtggag aaaaagtgct tagcaaaaaa atatactcac    120

ctctcctgcg ataaagtctt ctgccagcca tggcagagat gcattgaggg cacctgtgtt    180

tgtaaactac cgtatcagtg cccaaagaat ggcactgcag tgtgtgcaac taacaggaga    240

agcttcccaa catactgtca acaaaagagt ttggaatgtc ttcatccagg gacaaagttt    300

ttaaataacg gaacatgcac agccgaagga aagtttagtg tttccttgaa gcatggaaat    360

acagattcag agggaatagt tgaagtaaaa cttgtggacc aagataagac aatgttcata    420

tgcaaaagca gctggagcat gagggaagcc aacgtggcct gccttgacct tgggtttcaa    480

caaggtgctg atactcaaag aaggtttaag ttgtctgatc tctctataaa ttccactgaa    540
```

```
tgtctacatg tgcattgccg aggattagag accagtttgg ctgaatgtac ttttactaag    600

agaagaacta tgggttacca ggatttcgct gatgtggttt gttatacaca gaaagcagat    660

tctccaatgg atgacttctt tcagtgtgtg aatgggaaat acatttctca gatgaaagcc    720

tgtgatggta tcaatgattg tggagaccaa agtgatgaac tgtgttgtaa agcatgccaa    780

ggcaaaggct tccattgcaa atcgggtgtt tgcattccaa gccagtatca atgcaatggt    840

gaggtggact gcattacagg ggaagatgaa gttggctgtg caggctttgc atctgtggct    900

caagaagaaa cagaaatttt gactgctgac atggatgcag aaagaagacg gataaaatca    960

ttattaccta aactatcttg tggagttaaa aacagaatgc acattcgaag gaaacgaatt   1020

gtgggaggaa agcgagcaca actgggagac ctcccatggc aggtggcaat taaggatgcc   1080

agtggaatca cctgtggggg aatttatatt ggtggctgtt ggattctgac tgctgcacat   1140

tgtctcagag ccagtaaaac tcatcgttac caaatatgga caacagtagt agactggata   1200

caccccgacc ttaaacgtat agtaattgaa tacgtggata gaattatttt ccatgaaaac   1260

tacaatgcag gcacttacca aaatgacatc gctttgattg aaatgaaaaa agacggaaac   1320

aaaaaagatt gtgagctgcc tcgttccatc cctgcctgtg tcccctggtc tccttaccta   1380

ttccaaccta atgatacatg catcgtttct ggctggggac gagaaaaaga taacgaaaga   1440

gtcttttcac ttcagtgggg tgaagttaaa ctaataagca actgctctaa gttttacgga   1500

aatcgtttct atgaaaaaga aatggaatgt gcaggtacat atgatggttc catcgatgcc   1560

tgtaaagggg actctggagg ccccttagtc tgtatggatg ccaacaatgt gacttatgtc   1620

tggggtgttg tgagttgggg ggaaaactgt ggaaaaccag agttcccagg tgtttacacc   1680

aaagtggcca attattttga ctggattagc taccatgtag gaaggccttt tatttctcag   1740

tacaatgtat aa                                                       1752
```

```
<210> SEQ ID NO 3
<211> LENGTH: 1231
<212> TYPE: PRT
<213> ORGANISM: Homo sapiens

<400> SEQUENCE: 3

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160
```

```
Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575
```

```
His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
```

```
        995                 1000                1005

Lys Ala  Gly Glu Gln Val Thr  Tyr Thr Cys Ala Thr  Tyr Tyr Lys
    1010                 1015                1020

Met Asp  Gly Ala Ser Asn Val  Thr Cys Ile Asn Ser  Arg Trp Thr
    1025                 1030                1035

Gly Arg  Pro Thr Cys Arg Asp  Thr Ser Cys Val Asn  Pro Pro Thr
    1040                 1045                1050

Val Gln  Asn Ala Tyr Ile Val  Ser Arg Gln Met Ser  Lys Tyr Pro
    1055                 1060                1065

Ser Gly  Glu Arg Val Arg Tyr  Gln Cys Arg Ser Pro  Tyr Glu Met
    1070                 1075                1080

Phe Gly  Asp Glu Glu Val Met  Cys Leu Asn Gly Asn  Trp Thr Glu
    1085                 1090                1095

Pro Pro  Gln Cys Lys Asp Ser  Thr Gly Lys Cys Gly  Pro Pro Pro
    1100                 1105                1110

Pro Ile  Asp Asn Gly Asp Ile  Thr Ser Phe Pro Leu  Ser Val Tyr
    1115                 1120                1125

Ala Pro  Ala Ser Ser Val Glu  Tyr Gln Cys Gln Asn  Leu Tyr Gln
    1130                 1135                1140

Leu Glu  Gly Asn Lys Arg Ile  Thr Cys Arg Asn Gly  Gln Trp Ser
    1145                 1150                1155

Glu Pro  Pro Lys Cys Leu His  Pro Cys Val Ile Ser  Arg Glu Ile
    1160                 1165                1170

Met Glu  Asn Tyr Asn Ile Ala  Leu Arg Trp Thr Ala  Lys Gln Lys
    1175                 1180                1185

Leu Tyr  Ser Arg Thr Gly Glu  Ser Val Glu Phe Val  Cys Lys Arg
    1190                 1195                1200

Gly Tyr  Arg Leu Ser Ser Arg  Ser His Thr Leu Arg  Thr Thr Cys
    1205                 1210                1215

Trp Asp  Gly Lys Leu Glu Tyr  Pro Thr Cys Ala Lys  Arg
    1220                 1225                1230
```

```
<210> SEQ ID NO 4
<211> LENGTH: 3696
<212> TYPE: DNA
<213> ORGANISM: Homo sapiens

<400> SEQUENCE: 4

atgagacttc tagcaaagat tatttgcctt atgttatggg ctatttgtgt agcagaagat     60

tgcaatgaac ttcctccaag aagaaataca gaaattctga caggttcctg gtctgaccaa    120

acatatccag aaggcaccca ggctatctat aaatgccgcc ctggatatag atctcttgga    180

aatgtaataa tggtatgcag gaagggagaa tgggttgctc ttaatccatt aaggaaatgt    240

cagaaaaggc cctgtggaca tcctggagat actccttttg gtacttttac ccttacagga    300

ggaaatgtgt ttgaatatgg tgtaaaagct gtgtatacat gtaatgaggg gtatcaattg    360

ctaggtgaga ttaattaccg tgaatgtgac acagatggat ggaccaatga tattcctata    420

tgtgaagttg tgaagtgttt accagtgaca gcaccagaga atggaaaaat tgtcagtagt    480

gcaatggaac cagatcggga ataccatttt ggacaagcag tacggtttgt atgtaactca    540

ggctacaaga ttgaaggaga tgaagaaatg cattgttcag acgatggttt ttggagtaaa    600

gagaaaccaa agtgtgtgga aatttcatgc aaatccccag atgttataaa tggatctcct    660

atatctcaga agattattta taaggagaat gaacgatttc aatataaatg taacatgggt    720
```

-continued

```
tatgaataca gtgaaagagg agatgctgta tgcactgaat ctggatggcg tccgttgcct    780
tcatgtgaag aaaaatcatg tgataatcct tatattccaa atggtgacta ctcaccttta    840
aggattaaac acagaactgg agatgaaatc acgtaccagt gtagaaatgg tttttatcct    900
gcaacccggg gaaatacagc aaaatgcaca agtactggct ggatacctgc tccgagatgt    960
accttgaaac cttgtgatta tccagacatt aaacatggag gtctatatca tgagaatatg   1020
cgtagaccat actttccagt agctgtagga aaatattact cctattactg tgatgaacat   1080
tttgagactc cgtcaggaag ttactgggat cacattcatt gcacacaaga tggatggtcg   1140
ccagcagtac catgcctcag aaaatgttat tttccttatt tggaaaatgg atataatcaa   1200
aatcatggaa gaaagtttgt acagggtaaa tctatagacg ttgcctgcca tcctggctac   1260
gctcttccaa aagcgcagac cacagttaca tgtatggaga atggctggtc tcctactccc   1320
agatgcatcc gtgtcaaaac atgttccaaa tcaagtatag atattgagaa tgggtttatt   1380
tctgaatctc agtatacata tgccttaaaa gaaaaagcga aatatcaatg caaactagga   1440
tatgtaacag cagatggtga aacatcagga tcaattacat gtgggaaaga tggatggtca   1500
gctcaaccca cgtgcattaa atcttgtgat atcccagtat ttatgaatgc cagaactaaa   1560
aatgacttca catggtttaa gctgaatgac acattggact atgaatgcca tgatggttat   1620
gaaagcaata ctggaagcac cactggttcc atagtgtgtg gttacaatgg ttggtctgat   1680
ttacccatat gttatgaaag agaatgcgaa cttcctaaaa tagatgtaca cttagttcct   1740
gatcgcaaga aagaccagta taaagttgga gaggtgttga aattctcctg caaaccagga   1800
tttacaatag ttggacctaa ttccgttcag tgctaccact ttggattgtc tcctgacctc   1860
ccaatatgta aagagcaagt acaatcatgt ggtccacctc ctgaactcct caatgggaat   1920
gttaaggaaa aaacgaaaga agaatatgga cacagtgaag tggtggaata ttattgcaat   1980
cctagatttc taatgaaggg acctaataaa attcaatgtg ttgatggaga gtggacaact   2040
ttaccagtgt gtattgtgga ggagagtacc tgtggagata tacctgaact tgaacatggc   2100
tgggcccagc tttcttcccc tccttattac tatggagatt cagtggaatt caattgctca   2160
gaatcattta caatgattgg acacagatca attacgtgta ttcatggagt atggacccaa   2220
cttccccagt gtgtggcaat agataaactt aagaagtgca aatcatcaaa tttaattata   2280
cttgaggaac atttaaaaaa caagaaggaa ttcgatcata attctaacat aaggtacaga   2340
tgtagaggaa aagaaggatg gatacacaca gtctgcataa atggaagatg ggatccagaa   2400
gtgaactgct caatggcaca aatacaatta tgcccacctc cacctcagat tcccaattct   2460
cacaatatga caaccacact gaattatcgg gatggagaaa aagtatctgt tctttgccaa   2520
gaaaattatc taattcagga aggagaagaa attacatgca aagatggaag atggcagtca   2580
ataccactct gtgttgaaaa aattccatgt tcacaaccac ctcagataga acacggaacc   2640
attaattcat ccaggtcttc acaagaaagt tatgcacatg ggactaaatt gagttatact   2700
tgtgagggtg gtttcaggat atctgaagaa aatgaaacaa catgctacat gggaaaatgg   2760
agttctccac ctcagtgtga aggccttcct tgtaaatctc cacctgagat ttctcatggt   2820
gttgtagctc acatgtcaga cagttatcag tatggagaag aagttacgta caaatgtttt   2880
gaaggttttg gaattgatgg gcctgcaatt gcaaaatgct taggagaaaa atggtctcac   2940
cctccatcat gcataaaaac agattgtctc agtttaccta gctttgaaaa tgccataccc   3000
atgggagaga agaaggatgt gtataaggcg ggtgagcaag tgacttacac ttgtgcaaca   3060
tattacaaaa tggatggagc cagtaatgta acatgcatta atagcagatg gacaggaagg   3120
```

```
ccaacatgca gagacacctc ctgtgtgaat ccgcccacag tacaaaatgc ttatatagtg   3180

tcgagacaga tgagtaaata tccatctggt gagagagtac gttatcaatg taggagccct   3240

tatgaaatgt ttggggatga agaagtgatg tgtttaaatg gaaactggac ggaaccacct   3300

caatgcaaag attctacagg aaaatgtggg ccccctccac ctattgacaa tggggacatt   3360

acttcattcc cgttgtcagt atatgctcca gcttcatcag ttgagtacca atgccagaac   3420

ttgtatcaac ttgagggtaa caagcgaata acatgtagaa atggacaatg gtcagaacca   3480

ccaaaatgct tacatccgtg tgtaatatcc cgagaaatta tggaaaatta taacatagca   3540

ttaaggtgga cagccaaaca gaagctttat tcgagaacag gtgaatcagt tgaatttgtg   3600

tgtaaacggg gatatcgtct ttcatcacgt tctcacacat tgcgaacaac atgttgggat   3660

gggaaactgg agtatccaac ttgtgcaaaa agatag                              3696
```

<210> SEQ ID NO 5
<211> LENGTH: 934
<212> TYPE: DNA
<213> ORGANISM: Artificial Sequence
<220> FEATURE:
<223> OTHER INFORMATION: example promoter sequence

<400> SEQUENCE: 5

```
attgacgtca ataatgacgt atgttcccat agtaacgcca atagggactt tccattgacg     60

tcaatgggtg gagtatttac ggtaaactgc ccacttggca gtacatcaag tgtatcatat    120

gccaagtacg ccccctattg acgtcaatga cggtaaatgg cccgcctggc attatgccca    180

gtacatgacc ttatgggact ttcctacttg gcagtacatc tacgtattag tcatcgctat    240

taccatggtc gaggtgagcc ccacgttctg cttcactctc cccatctccc ccccctcccc    300

acccccaatt ttgtatttat ttatttttta attattttgt gcagcgatgg gggcgggggg    360

gggggggggg cgcgcgccag gcggggcggg gcggggcgag gggcggggcg gggcgaggcg    420

gagaggtgcg gcggcagcca atcagagcgg cgcgctccga aagtttcctt ttatggcgag    480

gcggcggcgg cggcggccct ataaaaagcg aagcgcgcgg cgggcgggag tcgctgcgcg    540

ctgccttcgc cccgtgcccc gctccgccgc cgcctcgcgc cgcccgcccc ggctctgact    600

gaccgcgtta ctcccacagg tgagcgggcg ggacggccct tctcctccgg gctgtaatta    660

gcgcttggtt taatgacggc ttgtttcttt tctgtggctg cgtgaaagcc ttgaggggct    720

ccgggagggc cctttgtgcg gggggagcgg ctcggggctg tccgcggggg gacggctgcc    780

ttcggggggg acggggcagg gcggggttcg gcttctggcg tgtgaccggc ggctctagag    840

cctctgctaa ccatgttcat gccttcttct ttttcctaca gctcctgggc aacgtgctgg    900

ttattgtgct gtctcatcat tttggcaaag aatt                                934
```

<210> SEQ ID NO 6
<211> LENGTH: 270
<212> TYPE: DNA
<213> ORGANISM: Artificial Sequence
<220> FEATURE:
<223> OTHER INFORMATION: Bovine Growth Hormone poly-A (bGH poly-A) signal sequence

<400> SEQUENCE: 6

```
tcgctgatca gcctcgactg tgccttctag ttgccagcca tctgttgttt gcccctcccc     60

cgtgccttcc ttgaccctgg aaggtgccac tcccactgtc ctttcctaat aaaatgagga    120

aattgcatcg cattgtctga gtaggtgtca ttctattctg gggggtgggg tggggcagga    180
```

```
cagcaagggg gaggattggg aagacaatag caggcatgct ggggatgcgg tgggctctat    240

ggcttctgag gcggaaagaa ccagctgggg                                     270


<210> SEQ ID NO 7
<211> LENGTH: 588
<212> TYPE: DNA
<213> ORGANISM: Artificial Sequence
<220> FEATURE:
<223> OTHER INFORMATION: example woodchuck hepatitis post-
      transcriptional regulatory element (WPRE) sequence

<400> SEQUENCE: 7

atcaacctct ggattacaaa atttgtgaaa gattgactgg tattcttaac tatgttgctc     60

cttttacgct atgtggatac gctgctttaa tgcctttgta tcatgctatt gcttcccgta    120

tggctttcat tttctcctcc ttgtataaat cctggttgct gtctctttat gaggagttgt    180

ggcccgttgt caggcaacgt ggcgtggtgt gcactgtgtt tgctgacgca acccccactg    240

gttggggcat tgccaccacc tgtcagctcc tttccgggac tttcgctttc cccctcccta    300

ttgccacggc ggaactcatc gccgcctgcc ttgcccgctg ctggacaggg gctcggctgt    360

tgggcactga caattccgtg gtgttgtcgg ggaaatcatc gtcctttcct tggctgctcg    420

cctgtgttgc cacctggatt ctgcgcggga cgtccttctg ctacgtccct tcggccctca    480

atccagcgga ccttccttcc cgcggcctgc tgccggctct gcggcctctt ccgcgtcttc    540

gccttcgccc tcagacgagt cggatctccc tttgggccgc ctccccgc                 588


<210> SEQ ID NO 8
<211> LENGTH: 1752
<212> TYPE: DNA
<213> ORGANISM: Artificial Sequence
<220> FEATURE:
<223> OTHER INFORMATION: codon-optimised nucleotide sequence encoding
      Complement Factor I

<400> SEQUENCE: 8

atgaagctgc tgcatgtctt tctgctgttt ctgtgcttcc atctgcggtt ctgtaaagtg     60

acctatacta gccaggagga tctggtggag aagaagtgtc tggccaagaa gtacacacac    120

ctgagctgcg acaaggtgtt ctgtcagcct tggcagcggt gcatcgaggg cacctgcgtg    180

tgcaagctgc cttaccagtg cccaaagaac ggcaccgccg tgtgcgccac aaatcggaga    240

tcttttccaa catattgcca gcagaagagc ctggagtgtc tgcaccccgg caccaagttc    300

ctgaacaatg gcacctgcac agccgagggc aagttttctg tgagcctgaa gcacggcaac    360

acagatagcg agggcatcgt ggaggtgaag ctggtggacc aggataagac catgttcatc    420

tgtaagagct cctggtccat gagggaggca aacgtggcat gcctggatct gggattccag    480

cagggagcag acacacagag gcgctttaag ctgtccgacc tgtctatcaa tagcaccgag    540

tgcctgcacg tgcactgtag ggcctggagg acatccctgg cagagtgcac cttcacaaag    600

cggagaacca tgggctacca ggactttgcc gacgtggtgt gctataccca gaaggccgat    660

agccccatgg acgatttctt tcagtgcgtg aacggcaagt atatctccca gatgaaggcc    720

tgcgacggca tcaatgactg tggcgatcag tctgacgagc tgtgctgtaa ggcctgtcag    780

ggcaagggct tccactgcaa gagcggcgtg tgcatccctt cccagtacca gtgcaacggc    840

gaggtggatt gtatcacagg agaggacgaa gtgggatgcg caggatttgc atctgtggca    900

caggaggaga cagagatcct gacagccgac atggatgccg agaggcgccg gatcaagtct    960
```

```
ctgctgccta agctgagctg tggcgtgaag aatcggatgc acatcagaag gaagcgcatc   1020

gtgggaggca agagggcaca gctgggcgat ctgccatggc aggtggccat caaggacgcc   1080

tctggcatca cctgcggcgg catctacatc ggaggatgtt ggatcctgac cgcagcacac   1140

tgcctgagag caagcaagac acacaggtat cagatctgga ccacagtggt ggattggatc   1200

cacccagacc tgaagagaat cgtgatcgag tacgtggata ggatcatctt tcacgagaac   1260

tacaatgccg gcacatatca gaacgacatc gccctgatcg agatgaagaa ggatggcaat   1320

aagaaggact gtgagctgcc cagatccatc cctgcatgcg tgccatggag cccctatctg   1380

ttccagccca acgatacctg catcgtgtcc ggatggggaa gggagaagga caatgagcgg   1440

gtgttttctc tgcagtgggg cgaggtgaag ctgatctcca actgttctaa gttctacggc   1500

aataggtttt atgagaagga gatggagtgc gccggcacct acgatggcag catcgacgcc   1560

tgtaagggcg attccggagg accactggtg tgcatggacg caaacaatgt gacatacgtg   1620

tggggagtgg tgtcctgggg agagaactgc ggcaagccag agttccccgg cgtatatacc   1680

aaggtggcca attattttga ttggatttcc taccacgtcg gcaggccctt tatttcccag   1740

tataatgtct aa                                                       1752


<210> SEQ ID NO 9
<211> LENGTH: 583
<212> TYPE: PRT
<213> ORGANISM: Homo sapiens

<400> SEQUENCE: 9

Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
```

```
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Ala Gln Glu Glu Thr
    290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
            420                 425                 430

Ile Glu Met Lys Lys Asp Gly Asn Lys Lys Asp Cys Glu Leu Pro Arg
        435                 440                 445

Ser Ile Pro Ala Cys Val Pro Trp Ser Pro Tyr Leu Phe Gln Pro Asn
    450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
            500                 505                 510

Thr Tyr Asp Gly Ser Ile Asp Ala Cys Lys Gly Asp Ser Gly Gly Pro
        515                 520                 525

Leu Val Cys Met Asp Ala Asn Asn Val Thr Tyr Val Trp Gly Val Val
    530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580


<210> SEQ ID NO 10
<211> LENGTH: 1752
<212> TYPE: DNA
<213> ORGANISM: Artificial Sequence
<220> FEATURE:
<223> OTHER INFORMATION: nucleotide sequence encoding Complement Factor
      I

<400> SEQUENCE: 10
```

```
atgaaactgc tgcatgtctt cctcctcttc ctgtgcttcc acctccgttt ctgtaaagtc     60

acctacacta gccaggagga tctggtggag aagaaatgcc tggccaagaa gtatacccac    120

ctgagctgcg acaaagtgtt ctgccagccc tggcaacgct gcattgaagg tacttgtgtg    180

tgcaagctgc cctaccagtg ccccaagaac ggcacggccg tgtgtgccac caacaggagg    240

agcttcccca cctactgcca gcagaagagc ctggaatgcc tccaccctgg caccaagttt    300

ctgaacaacg ggacctgcac agccgagggg aaattcagcg tctccctcaa gcacggcaat    360

acagactccg agggcattgt ggaagtgaag ctggtggacc aggacaagac catgttcatc    420

tgcaaaagca gctggtccat gcgggaggcc aatgtcgcct gcctggacct gggcttccag    480

cagggcgctg atacacagcg ccgctttaaa ctcagtgacc tcagcatcaa cagcactgag    540

tgtctgcacg tgcactgccg ggcctggag accagcctgg ctgagtgcac cttcaccaag     600

cgcaggacca tgggctacca ggattttgca gatgtggtct gctacaccca gaaggcagac    660

agccccatgg atgacttctt ccagtgtgtc aatggcaagt acatttccca gatgaaggct    720

tgtgacggga tcaatgattg cggggatcag agcgatgagc tctgctgcaa ggcctgccaa    780

gggaagggct ttcactgtaa gtctggggtg tgcatccctt ctcagtatca gtgcaacgga    840

gaggtggact gcatcactgg ggaggacgag gtgggctgtg ctggcttcgc ctctgtggcc    900

caggaggaga cagagatcct cacagctgac atggatgcag agcggcggcg catcaagagt    960

ctgctcccaa agctctcctg cggcgttaag aatcgcatgc acatccggag gaagcggatc   1020

gttggaggca aacgggctca gctgggggac ttgccgtggc aggtggccat caaagatgcc   1080

tccggaatca cctgtggtgg catctacatc ggcggctgct ggatcctgac cgccgcccac   1140

tgccttcggg ccagcaagac tcaccgctac cagatctgga ccaccgtggt ggattggatt   1200

caccccgacc tgaagaggat tgtcattgag tatgtcgacc gcatcatctt ccatgaaaac   1260

tacaatgccg ggacgtatca gaacgacatc gccctcatcg agatgaagaa ggatgggaac   1320

aagaaggact gtgagctgcc tcgctccatc cccgcctgtg taccatggtc tccgtacctg   1380

ttccagccaa atgacacatg catcgtgagc ggctggggcc gcgagaaaga caacgagagg   1440

gtcttctccc tgcagtgggg tgaagtcaag ctgatcagca actgctccaa gttctacggc   1500

aaccgcttct atgagaagga gatggagtgc gccggcacct atgacggcag cattgacgcg   1560

tgcaagggag acagtggggg cccccctggtc tgcatggacg ccaacaatgt gacctacgtg  1620

tggggagttg tgtcctgggg cgagaactgt ggcaagcctg agttcccggg cgtgtacaca   1680

aaggtggcaa actattttga ctggatctcc tatcacgttg gcaggccctt catttcacag   1740

tacaacgtat aa                                                       1752
```

<210> SEQ ID NO 11
<211> LENGTH: 449
<212> TYPE: PRT
<213> ORGANISM: Homo sapiens

<400> SEQUENCE: 11

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60
```

```
Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Ser Phe Thr
        435                 440                 445

Leu
```

<210> SEQ ID NO 12
<211> LENGTH: 1350
<212> TYPE: DNA

<213> ORGANISM: Artificial Sequence
<220> FEATURE:
<223> OTHER INFORMATION: nucleotide sequence encoding FHL1

<400> SEQUENCE: 12
atgcgcctcc tggccaagat catctgcctc atgctgtggg ccatctgcgt ggctgaggac 60
tgcaatgagc tgccgcccag gaggaacaca gagatcctga cagggagctg gtctgaccag 120
acctaccctg agggcaccca ggcgatctac aagtgccggc cgggctacag gagcctgggg 180
aacatcatca tggtgtgtag aaagggcgaa tgggtggccc tcaacccccct gaggaagtgc 240 cagaagcggc cctgtggcca ccccggggac acacccttcg ggaccttcac cctgaccggc 300
ggcaatgtgt ttgagtacgg cgtgaaggct gtctacacat gcaacgaggg gtaccagctg 360
ctgggcgaga ttaactaccg ggagtgtgac accgatgggt ggaccaacga cattcccatc 420
tgtgaggtgg tcaagtgtct ccccgtgaca gccccagaaa atggcaaaat cgtgagcagc 480
gccatggagc ctgaccgcga atatcacttt gggcaggccg tgaggtttgt gtgcaactcg 540
ggctacaaaa ttgaaggtga tgaggagatg cactgcagcg atgatggctt ctggtccaag 600
gagaagccca aatgtgtgga gatctcctgc aagtctcccg acgtgatcaa cggcagccca 660
atcagccaga agattattta caaagagaac gagcgcttcc agtacaagtg taacatgggc 720
tatgagtatt cagagagggg agatgccgtc tgcactgaga gcggctggag accactgcct 780
agctgcgagg aaaagagttg tgacaaccct tacatcccaa atggcgacta ctcccctctg 840
cggatcaaac accggaccgg ggatgaaatc acctatcagt gccgcaatgg attctacccg 900
gccacccgcg gcaacaccgc caaatgcacc agcacaggct ggatccccgc cccccgctgt 960
acgctgaagc cttgcgacta tccagacatc aagcacggag gcctgtacca cgaaaacatg 1020
cggcggcctt atttccctgt ggcagtgggg aagtactaca gctactactg cgacgagcac 1080
ttcgagaccc cctctggctc ctactgggac cacatccact gcacacagga cggctggtct 1140
ccagctgtgc cctgcctgag gaaatgctac ttcccctacc tggagaacgg atacaaccag 1200
aactatggcc gcaagttcgt gcagggcaag agcatcgatg tggcctgcca ccctggctac 1260
gccctgccca aggcccagac aactgtgacc tgcatggaga atggttggag ccccaccccg 1320
cgctgcatcc gggtgtcctt cacgctctga 1350

<210> SEQ ID NO 13
<211> LENGTH: 585
<212> TYPE: DNA
<213> ORGANISM: Artificial Sequence
<220> FEATURE:
<223> OTHER INFORMATION: cytomegalovirus (CMV) promoter sequence

<400> SEQUENCE: 13
ggagttccgc gttacataac ttacggtaaa tggcccgcct ggctgaccgc ccaacgaccc 60
ccgcccattg acgtcaataa tgacgtatgt tcccatagta acgccaatag ggactttcca 120
ttgacgtcaa tgggtggagt atttacggta aactgcccac ttggcagtac atcaagtgta 180
tcatatgcca agtacgcccc ctattgacgt caatgacggt aaatggcccg cctggcatta 240
tgcccagtac atgaccttat gggactttcc tacttggcag tacatctacg tattagtcat 300
cgctattacc atggtgatgc ggttttggca gtacatcaat gggcgtggat agcggtttga 360
ctcacgggga tttccaagtc tccaccccat tgacgtcaat gggagtttgt tttggcacca 420
aaatcaacgg gactttccaa aatgtcgtaa caactccgcc ccattgacgc aaatgggcgg 480
taggcgtgta cggtgggagg tctatataag cagagctcgt ttagtgaacc gtcagatcgc 540
ctggagacgc catccacgct gttttgacct ccatagaaga caccg 585

<210> SEQ ID NO 14
<211> LENGTH: 223
<212> TYPE: DNA
<213> ORGANISM: Artificial Sequence
<220> FEATURE:
<223> OTHER INFORMATION: Bovine Growth Hormone poly-A (bGH poly-A) signal sequence

<400> SEQUENCE: 14
gtgccttcta gttgccagcc atctgttgtt tgcccctccc ccgtgccttc cttgaccctg 60
gaaggtgcca ctcccactgt cctttcctaa taaaatgagg aaattgcatc gcattgtctg 120
agtaggtgtc attctattct ggggggtggg gtggggcagg acagcaaggg ggaggattgg 180
gaagacaata gcaggcatgc tggggatgcg gtgggctcta tgg 223

<210> SEQ ID NO 15
<211> LENGTH: 245
<212> TYPE: DNA
<213> ORGANISM: Artificial Sequence
<220> FEATURE:
<223> OTHER INFORMATION: WPRE3 sequence (shortened version of WPRE, contains only minimal gamma and alpha elements)

<400> SEQUENCE: 15
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttag ttcttgccac ggcggaactc 180
atcgccgcct gccttgcccg ctgctggaca ggggctcggc tgttgggcac tgacaattcc 240
gtggt 245

<210> SEQ ID NO 16
<211> LENGTH: 1350
<212> TYPE: DNA
<213> ORGANISM: Artificial Sequence
<220> FEATURE:
<223> OTHER INFORMATION: nucleotide sequence encoding Complement Factor H-like Protein 1 (FHL1)

<400> SEQUENCE: 16
atgagacttc tagcaaagat tatttgcctt atgttatggg ctatttgtgt agcagaagat 60
tgcaatgaac ttcctccaag aagaaataca gaaattctga caggttcctg gtctgaccaa 120
acatatccag aaggcaccca ggctatctat aaatgccgcc ctggatatag atctcttgga 180
aatataataa tggtatgcag gaagggagaa tgggttgctc ttaatccatt aaggaaatgt 240
cagaaaaggc cctgtggaca tcctggagat actccttttg gtacttttac ccttacagga 300
ggaaatgtgt ttgaatatgg tgtaaaagct gtgtatacat gtaatgaggg gtatcaattg 360
ctaggtgaga ttaattaccg tgaatgtgac acagatggat ggaccaatga tattcctata 420
tgtgaagttg tgaagtgttt accagtgaca gcaccagaga atggaaaaat tgtcagtagt 480
gcaatggaac cagatcggga ataccatttt ggacaagcag tacggtttgt atgtaactca 540
ggctacaaga ttgaaggaga tgaagaaatg cattgttcag acgatggttt ttggagtaaa 600
gagaaaccaa agtgtgtgga aatttcatgc aaatccccag atgttataaa tggatctcct 660
atatctcaga agattattta taaggagaat gaacgatttc aatataaatg taacatgggt 720
tatgaataca gtgaaagagg agatgctgta tgcactgaat ctggatggcg tccgttgcct 780

```
tcatgtgaag aaaaatcatg tgataatcct tatattccaa atggtgacta ctcaccttta     840

aggattaaac acagaactgg agatgaaatc acgtaccagt gtagaaatgg tttttatcct     900

gcaacccggg gaaatacagc aaaatgcaca agtactggct ggatacctgc tccgagatgt     960

accttgaaac cttgtgatta tccagacatt aaacatggag gtctatatca tgagaatatg    1020

cgtagaccat actttccagt agctgtagga aaatattact cctattactg tgatgaacat    1080

tttgagactc cgtcaggaag ttactgggat cacattcatt gcacacaaga tggatggtcg    1140

ccagcagtac catgcctcag aaaatgttat tttccttatt tggaaaatgg atataatcaa    1200

aattatggaa gaaagtttgt acagggtaaa tctatagacg ttgcctgcca tcctggctac    1260

gctcttccaa aagcgcagac cacagttaca tgtatggaga atggctggtc tcctactccc    1320

agatgcatcc gtgtcagctt taccctctga                                      1350
```

```
<210> SEQ ID NO 17
<211> LENGTH: 120
<212> TYPE: DNA
<213> ORGANISM: Artificial Sequence
<220> FEATURE:
<223> OTHER INFORMATION: linker sequence

<400> SEQUENCE: 17

cgaaggaaac gaggaagcgg agaagccaga cacaaacaga aaattgtggc accggtgaaa      60

cagactttga attttgacct tctcaagttg gcgggagacg tcgagtccaa ccctgggccc     120
```

```
<210> SEQ ID NO 18
<211> LENGTH: 121
<212> TYPE: DNA
<213> ORGANISM: Artificial Sequence
<220> FEATURE:
<223> OTHER INFORMATION: 5' adeno-associated virus (AAV) inverted
      terminal repeat (ITR) sequence

<400> SEQUENCE: 18

cgctcgctca ctgaggccgc ccgggcaaag cccgggcgtc gggcgacctt tggtcgcccg      60

gcctcagtga gcgagcgagc gcgcagagag ggagtggcca actccatcac taggggttcc     120

t                                                                     121
```

```
<210> SEQ ID NO 19
<211> LENGTH: 121
<212> TYPE: DNA
<213> ORGANISM: Artificial Sequence
<220> FEATURE:
<223> OTHER INFORMATION: 3' AAV ITR sequence

<400> SEQUENCE: 19

aggaacccct agtgatggag ttggccactc cctctctgcg cgctcgctcg ctcactgagg      60

ccgggcgacc aaaggtcgcc cgacgcccgg gctttgcccg ggcggcctca gtgagcgagc     120

g                                                                     121
```

```
<210> SEQ ID NO 20
<211> LENGTH: 57
<212> TYPE: DNA
<213> ORGANISM: Artificial Sequence
<220> FEATURE:
<223> OTHER INFORMATION: 5' ITR adjacent sequence

<400> SEQUENCE: 20

tgtagttaat gattaacccg ccatgctact tatctacgta gccatgctct aggtacc         57
```

<210> SEQ ID NO 21
<211> LENGTH: 85
<212> TYPE: DNA
<213> ORGANISM: Artificial Sequence
<220> FEATURE:
<223> OTHER INFORMATION: 3' ITR adjacent sequence

<400> SEQUENCE: 21
cttctgaggc ggaaagaacc agctggggct cgactagagc atggctacgt agataagtag 60
catggcgggt taatcattaa ctaca 85

<210> SEQ ID NO 22
<211> LENGTH: 4674
<212> TYPE: DNA
<213> ORGANISM: Artificial Sequence
<220> FEATURE:
<223> OTHER INFORMATION: polynucleotide sequence of the invention

<400> SEQUENCE: 22
cgctcgctca ctgaggccgc ccgggcaaag cccgggcgtc gggcgacctt tggtcgcccg 60
gcctcagtga gcgagcgagc gcgcagagag ggagtggcca actccatcac taggggttcc 120
ttgtagttaa tgattaaccc gccatgctac ttatctacgt agccatgctc taggtaccgg 180
agttccgcgt tacataactt acggtaaatg gcccgcctgg ctgaccgccc aacgaccccc 240
gcccattgac gtcaataatg acgtatgttc ccatagtaac gccaataggg actttccatt 300
gacgtcaatg ggtggagtat ttacggtaaa ctgcccactt ggcagtacat caagtgtatc 360
atatgccaag tacgccccct attgacgtca atgacggtaa atggcccgcc tggcattatg 420
cccagtacat gaccttatgg gactttccta cttggcagta catctacgta ttagtcatcg 480
ctattaccat ggtgatgcgg ttttggcagt acatcaatgg gcgtggatag cggtttgact 540
cacggggatt tccaagtctc caccccattg acgtcaatgg gagtttgttt tggcaccaaa 600
atcaacggga ctttccaaaa tgtcgtaaca actccgcccc attgacgcaa atgggcggta 660
ggcgtgtacg gtgggaggtc tatataagca gagctcgttt agtgaaccgt cagatcgcct 720
ggagacgcca tccacgctgt tttgacctcc atagaagaca ccgactagtg ccaccatgcg 780
cctcctggcc aagatcatct gcctcatgct gtgggccatc tgcgtggctg aggactgcaa 840
tgagctgccg cccaggagga acacagagat cctgacaggg agctggtctg accagaccta 900
ccctgagggc acccaggcga tctacaagtg ccggccgggc tacaggagcc tggggaacat 960
catcatggtg tgtagaaagg gcgaatgggt ggccctcaac cccctgagga agtgccagaa 1020
gcggccctgt ggccaccccg ggacacacc cttcgggacc ttcaccctga ccggcggcaa 1080
tgtgtttgag tacggcgtga aggctgtcta cacatgcaac gaggggtacc agctgctggg 1140
cgagattaac taccgggagt gtgacaccga tgggtggacc aacgacattc ccatctgtga 1200
ggtggtcaag tgtctccccg tgacagcccc agaaaatggc aaaatcgtga gcagcgccat 1260
ggagcctgac cgcgaatatc actttgggca ggccgtgagg tttgtgtgca actcgggcta 1320
caaaattgaa ggtgatgagg agatgcactg cagcgatgat ggcttctggt ccaaggagaa 1380
gcccaaatgt gtggagatct cctgcaagtc tcccgacgtg atcaacggca gcccaatcag 1440
ccagaagatt atttacaaag agaacgagcg cttccagtac aagtgtaaca tgggctatga 1500
gtattcagag aggggagatg ccgtctgcac tgagagcggc tggagaccac tgcctagctg 1560
cgaggaaaag agttgtgaca acccttacat cccaaatggc gactactccc ctctgcggat 1620

```
caaacaccgg accggggatg aaatcaccta tcagtgccgc aatggattct acccggccac   1680
ccgcggcaac accgccaaat gcaccagcac aggctggatc cccgccccc gctgtacgct   1740
gaagccttgc gactatccag acatcaagca cggaggcctg taccacgaaa acatgcggcg   1800
gccttatttc cctgtggcag tggggaagta ctacagctac tactgcgacg agcacttcga   1860
gaccccctct ggctcctact gggaccacat ccactgcaca caggacggct ggtctccagc   1920
tgtgccctgc ctgaggaaat gctacttccc ctacctggag aacggataca accagaacta   1980
tggccgcaag ttcgtgcagg gcaagagcat cgatgtggcc tgccaccctg gctacgccct   2040
gcccaaggcc cagacaactg tgacctgcat ggagaatggt tggagcccca ccccgcgctg   2100
catccgggtg tccttcacgc tccgaaggaa acgaggaagc ggagaagcca gacacaaaca   2160
gaaaattgtg gcaccggtga aacagacttt gaattttgac cttctcaagt tggcgggaga   2220
cgtcgagtcc aaccctgggc ccatgaaact gctgcatgtc ttcctcctct tcctgtgctt   2280
ccacctccgt ttctgtaaag tcacctacac tagccaggag gatctggtgg agaagaaatg   2340
cctggccaag aagtataccc acctgagctg cgacaaagtg ttctgccagc cctggcaacg   2400
ctgcattgaa ggtacttgtg tgtgcaagct gccctaccag tgccccaaga acggcacggc   2460
cgtgtgtgcc accaacagga ggagcttccc cacctactgc cagcagaaga gcctggaatg   2520
cctccaccct ggcaccaagt ttctgaacaa cgggacctgc acagccgagg ggaaattcag   2580
cgtctccctc aagcacggca atacagactc cgagggcatt gtggaagtga agctggtgga   2640
ccaggacaag accatgttca tctgcaaaag cagctggtcc atgcgggagg ccaatgtcgc   2700
ctgcctggac ctgggcttcc agcagggcgc tgatacacag cgccgcttta aactcagtga   2760
cctcagcatc aacagcactg agtgtctgca cgtgcactgc cggggcctgg agaccagcct   2820
ggctgagtgc accttcacca agcgcaggac catgggctac caggattttg cagatgtggt   2880
ctgctacacc cagaaggcag acagccccat ggatgacttc ttccagtgtg tcaatggcaa   2940
gtacatttcc cagatgaagg cttgtgacgg gatcaatgat tgcggggatc agagcgatga   3000
gctctgctgc aaggcctgcc aagggaaggg ctttcactgt aagtctgggg tgtgcatccc   3060
ttctcagtat cagtgcaacg gagaggtgga ctgcatcact ggggaggacg aggtgggctg   3120
tgctggcttc gcctctgtgg cccaggagga gacagagatc ctcacagctg acatggatgc   3180
agagcggcgg cgcatcaaga gtctgctccc aaagctctcc tgcggcgtta agaatcgcat   3240
gcacatccgg aggaagcgga tcgttggagg caaacgggct cagctggggg acttgccgtg   3300
gcaggtggcc atcaaagatg cctccggaat cacctgtggt ggcatctaca tcggcggctg   3360
ctggatcctg accgccgccc actgccttcg ggccagcaag actcaccgct accagatctg   3420
gaccaccgtg gtggattgga ttcaccccga cctgaagagg attgtcattg agtatgtcga   3480
ccgcatcatc ttccatgaaa actacaatgc cgggacgtat cagaacgaca tcgccctcat   3540
cgagatgaag aaggatggga acaagaagga ctgtgagctg cctcgctcca tccccgcctg   3600
tgtaccatgg tctccgtacc tgttccagcc aaatgacaca tgcatcgtga gcggctgggg   3660
ccgcgagaaa gacaacgaga gggtcttctc cctgcagtgg ggtgaagtca agctgatcag   3720
caactgctcc aagttctacg gcaaccgctt ctatgagaag gagatggagt gcgccggcac   3780
ctatgacggc agcattgacg cgtgcaaggg agacagtggg ggccccctgg tctgcatgga   3840
cgccaacaat gtgacctacg tgtggggagt tgtgtcctgg ggcgagaact gtggcaagcc   3900
tgagttcccg ggcgtgtaca caaaggtggc aaactatttt gactggatct cctatcacgt   3960
tggcaggccc ttcatttcac agtacaacgt ataactcgag aatcaacctc tggattacaa   4020
```

```
aatttgtgaa agattgactg gtattcttaa ctatgttgct ccttttacgc tatgtggata   4080
cgctgcttta atgcctttgt atcatgctat tgcttcccgt atggctttca ttttctcctc   4140
cttgtataaa tcctggttag ttcttgccac ggcggaactc atcgccgcct gccttgcccg   4200
ctgctggaca ggggctcggc tgttgggcac tgacaattcc gtggtgtgcc ttctagttgc   4260
cagccatctg ttgtttgccc ctcccccgtg ccttccttga ccctggaagg tgccactccc   4320
actgtccttt cctaataaaa tgaggaaatt gcatcgcatt gtctgagtag gtgtcattct   4380
attctggggg gtggggtggg gcaggacagc aagggggagg attgggaaga caatagcagg   4440
catgctgggg atgcggtggg ctctatggct tctgaggcgg aaagaaccag ctggggctcg   4500
actagagcat ggctacgtag ataagtagca tggcgggtta atcattaact acaaggaacc   4560
cctagtgatg gagttggcca ctccctctct gcgcgctcgc tcgctcactg aggccgggcg   4620
accaaaggtc gcccgacgcc cgggctttgc ccgggcggcc tcagtgagcg agcg         4674
```

<210> SEQ ID NO 23
<211> LENGTH: 4548
<212> TYPE: DNA
<213> ORGANISM: Artificial Sequence
<220> FEATURE:
<223> OTHER INFORMATION: polynucleotide sequence of the invention

<400> SEQUENCE: 23

```
cgctcgctca ctgaggccgc ccgggcaaag cccgggcgtc gggcgacctt tggtcgcccg     60
gcctcagtga gcgagcgagc gcgcagagag ggagtggcca actccatcac taggggttcc    120
tggcgcgccg gagttccgcg ttacataact tacggtaaat ggcccgcctg gctgaccgcc    180
caacgacccc cgcccattga cgtcaataat gacgtatgtt cccatagtaa cgccaatagg    240
gactttccat tgacgtcaat gggtggagta tttacggtaa actgcccact tggcagtaca    300
tcaagtgtat catatgccaa gtacgccccc tattgacgtc aatgacggta aatggcccgc    360
ctggcattat gcccagtaca tgaccttatg ggactttcct acttggcagt acatctacgt    420
attagtcatc gctattacca tggtgatgcg gttttggcag tacatcaatg ggcgtggata    480
gcggtttgac tcacggggat ttccaagtct ccaccccatt gacgtcaatg ggagtttgtt    540
ttggcaccaa aatcaacggg actttccaaa atgtcgtaac aactccgccc cattgacgca    600
aatgggcggt aggcgtgtac ggtgggaggt ctatataagc agagctcgtt tagtgaaccg    660
tcagatcgcc tggagacgcc atccacgctg ttttgacctc catagaagac accgactagt    720
gccaccatgc gcctcctggc caagatcatc tgcctcatgc tgtgggccat ctgcgtggct    780
gaggactgca atgagctgcc gcccaggagg aacacagaga tcctgacagg gagctggtct    840
gaccagacct accctgaggg cacccaggcg atctacaagt gccggccggg ctacaggagc    900
ctggggaaca tcatcatggt gtgtagaaag ggcgaatggg tggccctcaa ccccctgagg    960
aagtgccaga agcggccctg tggccacccc ggggacacac ccttcgggac cttcaccctg   1020
accggcggca atgtgtttga gtacggcgtg aaggctgtct acacatgcaa cgaggggtac   1080
cagctgctgg gcgagattaa ctaccgggag tgtgacaccg atgggtggac caacgacatt   1140
cccatctgtg aggtggtcaa gtgtctcccc gtgacagccc cagaaaatgg caaaatcgtg   1200
agcagcgcca tggagcctga ccgcgaatat cactttgggc aggccgtgag gtttgtgtgc   1260
aactcgggct acaaaattga aggtgatgag gagatgcact gcagcgatga tggcttctgg   1320
tccaaggaga agcccaaatg tgtggagatc tcctgcaagt ctcccgacgt gatcaacggc   1380
```

```
agcccaatca gccagaagat tatttacaaa gagaacgagc gcttccagta caagtgtaac   1440
atgggctatg agtattcaga gaggggagat gccgtctgca ctgagagcgg ctggagacca   1500
ctgcctagct gcgaggaaaa gagttgtgac aacccttaca tcccaaatgg cgactactcc   1560
cctctgcgga tcaaacaccg gaccggggat gaaatcacct atcagtgccg caatggattc   1620
tacccggcca cccgcggcaa caccgccaaa tgcaccagca caggctggat ccccgccccc   1680
cgctgtacgc tgaagccttg cgactatcca gacatcaagc acggaggcct gtaccacgaa   1740
aacatgcggc ggccttattt ccctgtggca gtggggaagt actacagcta ctactgcgac   1800
gagcacttcg agaccccctc tggctcctac tgggaccaca tccactgcac acaggacggc   1860
tggtctccag ctgtgccctg cctgaggaaa tgctacttcc cctacctgga gaacggatac   1920
aaccagaact atggccgcaa gttcgtgcag ggcaagagca tcgatgtggc ctgccaccct   1980
ggctacgccc tgcccaaggc ccagacaact gtgacctgca tggagaatgg ttggagcccc   2040
accccgcgct gcatccgggt gtccttcacg ctccgaagga aacgaggaag cggagaagcc   2100
agacacaaac agaaaattgt ggcaccggtg aaacagactt tgaattttga ccttctcaag   2160
ttggcgggag acgtcgagtc caaccctggg cccatgaaac tgctgcatgt cttcctcctc   2220
ttcctgtgct tccacctccg tttctgtaaa gtcacctaca ctagccagga ggatctggtg   2280
gagaagaaat gcctggccaa gaagtatacc cacctgagct gcgacaaagt gttctgccag   2340
ccctggcaac gctgcattga aggtacttgt gtgtgcaagc tgccctacca gtgccccaag   2400
aacggcacgg ccgtgtgtgc caccaacagg aggagcttcc ccacctactg ccagcagaag   2460
agcctggaat gcctccaccc tggcaccaag tttctgaaca acgggacctg cacagccgag   2520
gggaaattca gcgtctccct caagcacggc aatacagact ccgagggcat tgtggaagtg   2580
aagctggtgg accaggacaa gaccatgttc atctgcaaaa gcagctggtc catgcgggag   2640
gccaatgtcg cctgcctgga cctgggcttc cagcagggcg ctgatacaca gcgccgcttt   2700
aaactcagtg acctcagcat caacagcact gagtgtctgc acgtgcactg ccggggcctg   2760
gagaccagcc tggctgagtg caccttcacc aagcgcagga ccatgggcta ccaggatttt   2820
gcagatgtgg tctgctacac ccagaaggca gacagcccca tggatgactt cttccagtgt   2880
gtcaatggca agtacatttc ccagatgaag gcttgtgacg ggatcaatga ttgcggggat   2940
cagagcgatg agctctgctg caaggcctgc caagggaagg gctttcactg taagtctggg   3000
gtgtgcatcc cttctcagta tcagtgcaac ggagaggtgg actgcatcac tggggaggac   3060
gaggtgggct gtgctggctt cgcctctgtg gcccaggagg agacagagat cctcacagct   3120
gacatggatg cagagcggcg gcgcatcaag agtctgctcc caaagctctc ctgcggcgtt   3180
aagaatcgca tgcacatccg gaggaagcgg atcgttggag gcaaacgggc tcagctgggg   3240
gacttgccgt ggcaggtggc catcaaagat gcctccggaa tcacctgtgg tggcatctac   3300
atcggcggct gctggatcct gaccgccgcc cactgccttc gggccagcaa gactcaccgc   3360
taccagatct ggaccaccgt ggtggattgg attcaccccg acctgaagag gattgtcatt   3420
gagtatgtcg accgcatcat cttccatgaa aactacaatg ccgggacgta tcagaacgac   3480
atcgccctca tcgagatgaa gaaggatggg aacaagaagg actgtgagct gcctcgctcc   3540
atccccgcct gtgtaccatg gtctccgtac ctgttccagc caaatgacac atgcatcgtg   3600
agcggctggg gccgcgagaa agacaacgag agggtcttct ccctgcagtg gggtgaagtc   3660
aagctgatca gcaactgctc caagttctac ggcaaccgct tctatgagaa ggagatggag   3720
tgcgccggca cctatgacgg cagcattgac gcgtgcaagg gagacagtgg gggcccctg    3780
```

```
gtctgcatgg acgccaacaa tgtgacctac gtgtggggag ttgtgtcctg gggcgagaac   3840

tgtggcaagc ctgagttccc gggcgtgtac acaaaggtgg caaactattt tgactggatc   3900

tcctatcacg ttggcaggcc cttcatttca cagtacaacg tataactcga gaatcaacct   3960

ctggattaca aaatttgtga aagattgact ggtattctta actatgttgc tccttttacg   4020

ctatgtggat acgctgcttt aatgcctttg tatcatgcta ttgcttcccg tatggctttc   4080

attttctcct ccttgtataa atcctggtta gttcttgcca cggcggaact catcgccgcc   4140

tgccttgccc gctgctggac aggggctcgg ctgttgggca ctgacaattc cgtggtgtgc   4200

cttctagttg ccagccatct gttgtttgcc cctcccccgt gccttccttg accctggaag   4260

gtgccactcc cactgtcctt tcctaataaa atgaggaaat tgcatcgcat tgtctgagta   4320

ggtgtcattc tattctgggg ggtggggtgg ggcaggacag caagggggag gattgggaag   4380

acaatagcag gcatgctggg gatgcggtgg gctctatggg cggccgcagg aacccctagt   4440

gatggagttg gccactccct ctctgcgcgc tcgctcgctc actgaggccg ggcgaccaaa   4500

ggtcgcccga cgcccgggct ttgcccgggc ggcctcagtg agcgagcg                4548
```

```
<210> SEQ ID NO 24
<211> LENGTH: 2039
<212> TYPE: PRT
<213> ORGANISM: Artificial Sequence
<220> FEATURE:
<223> OTHER INFORMATION: example Complement Receptor 1 (CR1) sequence

<400> SEQUENCE: 24

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
    210                 215                 220
```

-continued

```
Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
        355                 360                 365

Arg Val Leu Phe Pro Val Asn Leu Gln Leu Gly Ala Lys Val Asp Phe
    370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Pro Val Ile Pro Asn Gly Arg His
            420                 425                 430

Thr Gly Lys Pro Leu Glu Val Phe Pro Phe Gly Lys Thr Val Asn Tyr
        435                 440                 445

Thr Cys Asp Pro His Pro Asp Arg Gly Thr Ser Phe Asp Leu Ile Gly
    450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
    530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
    610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
```

```
                645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
    690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
    770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
        835                 840                 845

Tyr Cys Val Leu Ala Gly Met Glu Ser Leu Trp Asn Ser Ser Val Pro
    850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
                885                 890                 895

Asn Tyr Thr Cys Asp Pro His Pro Asp Arg Gly Thr Ser Phe Asp Leu
            900                 905                 910

Ile Gly Glu Ser Thr Ile Arg Cys Thr Ser Asp Pro Gln Gly Asn Gly
        915                 920                 925

Val Trp Ser Ser Pro Ala Pro Arg Cys Gly Ile Leu Gly His Cys Gln
    930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
            980                 985                 990

Ser Ser Pro Lys Asp Val Cys Lys  Arg Lys Ser Cys Lys  Thr Pro Pro
        995                 1000                1005

Asp Pro  Val Asn Gly Met Val  His Val Ile Thr Asp  Ile Gln Val
    1010                 1015                 1020

Gly Ser  Arg Ile Asn Tyr Ser  Cys Thr Thr Gly His  Arg Leu Ile
    1025                 1030                 1035

Gly His  Ser Ser Ala Glu Cys  Ile Leu Ser Gly Asn  Thr Ala His
    1040                 1045                 1050

Trp Ser  Thr Lys Pro Pro Ile  Cys Gln Arg Ile Pro  Cys Gly Leu
    1055                 1060                 1065
```

```
Pro Pro  Thr Ile Ala Asn Gly  Asp Phe Ile Ser Thr  Asn Arg Glu
    1070                 1075                 1080

Asn Phe  His Tyr Gly Ser Val  Val Thr Tyr Arg Cys  Asn Leu Gly
    1085                 1090                 1095

Ser Arg  Gly Arg Lys Val Phe  Glu Leu Val Gly Glu  Pro Ser Ile
    1100                 1105                 1110

Tyr Cys  Thr Ser Asn Asp Asp  Gln Val Gly Ile Trp  Ser Gly Pro
    1115                 1120                 1125

Ala Pro  Gln Cys Ile Ile Pro  Asn Lys Cys Thr Pro  Pro Asn Val
    1130                 1135                 1140

Glu Asn  Gly Ile Leu Val Ser  Asp Asn Arg Ser Leu  Phe Ser Leu
    1145                 1150                 1155

Asn Glu  Val Val Glu Phe Arg  Cys Gln Pro Gly Phe  Val Met Lys
    1160                 1165                 1170

Gly Pro  Arg Arg Val Lys Cys  Gln Ala Leu Asn Lys  Trp Glu Pro
    1175                 1180                 1185

Glu Leu  Pro Ser Cys Ser Arg  Val Cys Gln Pro Pro  Pro Glu Ile
    1190                 1195                 1200

Leu His  Gly Glu His Thr Pro  Ser His Gln Asp Asn  Phe Ser Pro
    1205                 1210                 1215

Gly Gln  Glu Val Phe Tyr Ser  Cys Glu Pro Gly Tyr  Asp Leu Arg
    1220                 1225                 1230

Gly Ala  Ala Ser Leu His Cys  Thr Pro Gln Gly Asp  Trp Ser Pro
    1235                 1240                 1245

Glu Ala  Pro Arg Cys Ala Val  Lys Ser Cys Asp Asp  Phe Leu Gly
    1250                 1255                 1260

Gln Leu  Pro His Gly Arg Val  Leu Phe Pro Leu Asn  Leu Gln Leu
    1265                 1270                 1275

Gly Ala  Lys Val Ser Phe Val  Cys Asp Glu Gly Phe  Arg Leu Lys
    1280                 1285                 1290

Gly Ser  Ser Val Ser His Cys  Val Leu Val Gly Met  Arg Ser Leu
    1295                 1300                 1305

Trp Asn  Asn Ser Val Pro Val  Cys Glu His Ile Phe  Cys Pro Asn
    1310                 1315                 1320

Pro Pro  Ala Ile Leu Asn Gly  Arg His Thr Gly Thr  Pro Ser Gly
    1325                 1330                 1335

Asp Ile  Pro Tyr Gly Lys Glu  Ile Ser Tyr Thr Cys  Asp Pro His
    1340                 1345                 1350

Pro Asp  Arg Gly Met Thr Phe  Asn Leu Ile Gly Glu  Ser Thr Ile
    1355                 1360                 1365

Arg Cys  Thr Ser Asp Pro His  Gly Asn Gly Val Trp  Ser Ser Pro
    1370                 1375                 1380

Ala Pro  Arg Cys Glu Leu Ser  Val Arg Ala Gly His  Cys Lys Thr
    1385                 1390                 1395

Pro Glu  Gln Phe Pro Phe Ala  Ser Pro Thr Ile Pro  Ile Asn Asp
    1400                 1405                 1410

Phe Glu  Phe Pro Val Gly Thr  Ser Leu Asn Tyr Glu  Cys Arg Pro
    1415                 1420                 1425

Gly Tyr  Phe Gly Lys Met Phe  Ser Ile Ser Cys Leu  Glu Asn Leu
    1430                 1435                 1440

Val Trp  Ser Ser Val Glu Asp  Asn Cys Arg Arg Lys  Ser Cys Gly
    1445                 1450                 1455
```

```
Pro Pro Pro Glu Pro Phe Asn Gly Met Val His Ile Asn Thr Asp
    1460                1465                1470

Thr Gln Phe Gly Ser Thr Val Asn Tyr Ser Cys Asn Glu Gly Phe
    1475                1480                1485

Arg Leu Ile Gly Ser Pro Ser Thr Thr Cys Leu Val Ser Gly Asn
    1490                1495                1500

Asn Val Thr Trp Asp Lys Lys Ala Pro Ile Cys Glu Ile Ile Ser
    1505                1510                1515

Cys Glu Pro Pro Pro Thr Ile Ser Asn Gly Asp Phe Tyr Ser Asn
    1520                1525                1530

Asn Arg Thr Ser Phe His Asn Gly Thr Val Val Thr Tyr Gln Cys
    1535                1540                1545

His Thr Gly Pro Asp Gly Glu Gln Leu Phe Glu Leu Val Gly Glu
    1550                1555                1560

Arg Ser Ile Tyr Cys Thr Ser Lys Asp Asp Gln Val Gly Val Trp
    1565                1570                1575

Ser Ser Pro Pro Pro Arg Cys Ile Ser Thr Asn Lys Cys Thr Ala
    1580                1585                1590

Pro Glu Val Glu Asn Ala Ile Arg Val Pro Gly Asn Arg Ser Phe
    1595                1600                1605

Phe Thr Leu Thr Glu Ile Ile Arg Phe Arg Cys Gln Pro Gly Phe
    1610                1615                1620

Val Met Val Gly Ser His Thr Val Gln Cys Gln Thr Asn Gly Arg
    1625                1630                1635

Trp Gly Pro Lys Leu Pro His Cys Ser Arg Val Cys Gln Pro Pro
    1640                1645                1650

Pro Glu Ile Leu His Gly Glu His Thr Leu Ser His Gln Asp Asn
    1655                1660                1665

Phe Ser Pro Gly Gln Glu Val Phe Tyr Ser Cys Glu Pro Ser Tyr
    1670                1675                1680

Asp Leu Arg Gly Ala Ala Ser Leu His Cys Thr Pro Gln Gly Asp
    1685                1690                1695

Trp Ser Pro Glu Ala Pro Arg Cys Thr Val Lys Ser Cys Asp Asp
    1700                1705                1710

Phe Leu Gly Gln Leu Pro His Gly Arg Val Leu Leu Pro Leu Asn
    1715                1720                1725

Leu Gln Leu Gly Ala Lys Val Ser Phe Val Cys Asp Glu Gly Phe
    1730                1735                1740

Arg Leu Lys Gly Arg Ser Ala Ser His Cys Val Leu Ala Gly Met
    1745                1750                1755

Lys Ala Leu Trp Asn Ser Ser Val Pro Val Cys Glu Gln Ile Phe
    1760                1765                1770

Cys Pro Asn Pro Pro Ala Ile Leu Asn Gly Arg His Thr Gly Thr
    1775                1780                1785

Pro Phe Gly Asp Ile Pro Tyr Gly Lys Glu Ile Ser Tyr Ala Cys
    1790                1795                1800

Asp Thr His Pro Asp Arg Gly Met Thr Phe Asn Leu Ile Gly Glu
    1805                1810                1815

Ser Ser Ile Arg Cys Thr Ser Asp Pro Gln Gly Asn Gly Val Trp
    1820                1825                1830

Ser Ser Pro Ala Pro Arg Cys Glu Leu Ser Val Pro Ala Ala Cys
    1835                1840                1845

Pro His Pro Pro Lys Ile Gln Asn Gly His Tyr Ile Gly Gly His
```

```
    1850                1855                1860

Val Ser  Leu Tyr Leu Pro Gly  Met Thr Ile Ser Tyr  Ile Cys Asp
    1865                1870                1875

Pro Gly  Tyr Leu Leu Val Gly  Lys Gly Phe Ile Phe  Cys Thr Asp
    1880                1885                1890

Gln Gly  Ile Trp Ser Gln Leu  Asp His Tyr Cys Lys  Glu Val Asn
    1895                1900                1905

Cys Ser  Phe Pro Leu Phe Met  Asn Gly Ile Ser Lys  Glu Leu Glu
    1910                1915                1920

Met Lys  Lys Val Tyr His Tyr  Gly Asp Tyr Val Thr  Leu Lys Cys
    1925                1930                1935

Glu Asp  Gly Tyr Thr Leu Glu  Gly Ser Pro Trp Ser  Gln Cys Gln
    1940                1945                1950

Ala Asp  Asp Arg Trp Asp Pro  Pro Leu Ala Lys Cys  Thr Ser Arg
    1955                1960                1965

Thr His  Asp Ala Leu Ile Val  Gly Thr Leu Ser Gly  Thr Ile Phe
    1970                1975                1980

Phe Ile  Leu Leu Ile Ile Phe  Leu Ser Trp Ile Ile  Leu Lys His
    1985                1990                1995

Arg Lys  Gly Asn Asn Ala His  Glu Asn Pro Lys Glu  Val Ala Ile
    2000                2005                2010

His Leu  His Ser Gln Gly Gly  Ser Ser Val His Pro  Arg Thr Leu
    2015                2020                2025

Gln Thr  Asn Glu Glu Asn Ser  Arg Val Leu Pro
    2030                2035
```

<210> SEQ ID NO 25
<211> LENGTH: 6120
<212> TYPE: DNA
<213> ORGANISM: Artificial Sequence
<220> FEATURE:
<223> OTHER INFORMATION: nucleotide sequence encoding CR1

<400> SEQUENCE: 25

```
atgggggcct cttctccaag aagcccggag cctgtcgggc cgccggcgcc cggtctcccc     60

ttctgctgcg gaggatccct gctggcggtt gtggtgctgc ttgcgctgcc ggtggcctgg    120

ggtcaatgca atgccccaga atggcttcca tttgccaggc ctaccaacct aactgatgaa    180

tttgagtttc ccattgggac atatctgaac tatgaatgcc gccctggtta ttccggaaga    240

ccgttttcta tcatctgcct aaaaaactca gtctggactg gtgctaagga caggtgcaga    300

cgtaaatcat gtcgtaatcc tccagatcct gtgaatggca tggtgcatgt gatcaaaggc    360

atccagttcg gatcccaaat taaatattct tgtactaaag gataccgact cattggttcc    420

tcgtctgcca catgcatcat ctcaggtgat actgtcattt gggataatga aacacctatt    480

tgtgacagaa ttccttgtgg gctacccccc accatcacca atggagattt cattagcacc    540

aacagagaga attttcacta tggatcagtg gtgacctacc gctgcaatcc tggaagcgga    600

gggagaaagg tgtttgagct tgtgggtgag ccctccatat actgcaccag caatgacgat    660

caagtgggca tctggagcgg ccccgcccct cagtgcatta tacctaacaa atgcacgcct    720

ccaaatgtgg aaaatggaat attggtatct gacaacagaa gcttattttc cttaaatgaa    780

gttgtggagt ttaggtgtca gcctggcttt gtcatgaaag gaccccgccg tgtgaagtgc    840

caggccctga acaaatggga gccggagcta ccaagctgct ccagggtatg tcagccacct    900

ccagatgtcc tgcatgctga gcgtacccaa agggacaagg acaacttttc acctgggcag    960
```

-continued

```
gaagtgttct acagctgtga gcccggctac gacctcagag gggctgcgtc tatgcgctgc   1020
acaccccagg gagactggag ccctgcagcc cccacatgtg aagtgaaatc ctgtgatgac   1080
ttcatgggcc aacttcttaa tggccgtgtg ctatttccag taaatctcca gcttggagca   1140
aaagtggatt ttgtttgtga tgaaggattt caattaaaag gcagctctgc tagttactgt   1200
gtcttggctg gaatggaaag cctttggaat agcagtgttc cagtgtgtga acaaatcttt   1260
tgtccaagtc ctccagttat tcctaatggg agacacacag gaaaacctct ggaagtcttt   1320
ccctttggga aaacagtaaa ttacacatgc gacccccacc cagacagagg gacgagcttc   1380
gacctcattg gagagagcac catccgctgc acaagtgacc ctcaagggaa tggggtttgg   1440
agcagccctg cccctcgctg tggaattctg ggtcactgtc aagccccaga tcattttctg   1500
tttgccaagt tgaaaaccca aaccaatgca tctgactttc ccattgggac atctttaaag   1560
tacgaatgcc gtcctgagta ctacgggagg ccattctcta tcacatgtct agataacctg   1620
gtctggtcaa gtcccaaaga tgtctgtaaa cgtaaatcat gtaaaactcc tccagatcca   1680
gtgaatggca tggtgcatgt gatcacagac atccaggttg gatccagaat caactattct   1740
tgtactacag ggcaccgact cattggtcac tcatctgctg aatgtatcct ctcgggcaat   1800
gctgcccatt ggagcacgaa gccgccaatt tgtcaacgaa ttccttgtgg gctacccccc   1860
accatcgcca atggagattt cattagcacc aacagagaga attttcacta tggatcagtg   1920
gtgacctacc gctgcaatcc tggaagcgga gggagaaagg tgtttgagct tgtgggtgag   1980
ccctccatat actgcaccag caatgacgat caagtgggca tctggagcgg cccggcccct   2040
cagtgcatta tacctaacaa atgcacgcct ccaaatgtgg aaaatggaat attggtatct   2100
gacaacagaa gcttattttc cttaaatgaa gttgtggagt ttaggtgtca gcctggcttt   2160
gtcatgaaag gaccccgccg tgtgaagtgc caggccctga acaaatggga gccggagcta   2220
ccaagctgct ccagggtatg tcagccacct ccagatgtcc tgcatgctga gcgtacccaa   2280
agggacaagg acaacttttc acccgggcag gaagtgttct acagctgtga gcccggctat   2340
gacctcagag gggctgcgtc tatgcgctgc acaccccagg gagactggag ccctgcagcc   2400
cccacatgtg aagtgaaatc ctgtgatgac ttcatgggcc aacttcttaa tggccgtgtg   2460
ctatttccag taaatctcca gcttggagca aaagtggatt ttgtttgtga tgaaggattt   2520
caattaaaag gcagctctgc tagttattgt gtcttggctg gaatggaaag cctttggaat   2580
agcagtgttc cagtgtgtga acaaatcttt tgtccaagtc ctccagttat tcctaatggg   2640
agacacacag gaaaacctct ggaagtcttt ccctttggaa aagcagtaaa ttacacatgc   2700
gacccccacc cagacagagg gacgagcttc gacctcattg gagagagcac catccgctgc   2760
acaagtgacc ctcaagggaa tggggtttgg agcagccctg cccctcgctg tggaattctg   2820
ggtcactgtc aagccccaga tcattttctg tttgccaagt tgaaaaccca aaccaatgca   2880
tctgactttc ccattgggac atctttaaag tacgaatgcc gtcctgagta ctacgggagg   2940
ccattctcta tcacatgtct agataacctg gtctggtcaa gtcccaaaga tgtctgtaaa   3000
cgtaaatcat gtaaaactcc tccagatcca gtgaatggca tggtgcatgt gatcacagac   3060
atccaggttg gatccagaat caactattct tgtactacag ggcaccgact cattggtcac   3120
tcatctgctg aatgtatcct ctcaggcaat actgcccatt ggagcacgaa gccgccaatt   3180
tgtcaacgaa ttccttgtgg gctacccccca accatcgcca atggagattt cattagcacc   3240
aacagagaga attttcacta tggatcagtg gtgacctacc gctgcaatct tggaagcaga   3300
```

```
gggagaaagg tgtttgagct tgtgggtgag ccctccatat actgcaccag caatgacgat   3360
caagtgggca tctggagcgg ccccgcccct cagtgcatta tacctaacaa atgcacgcct   3420
ccaaatgtgg aaaatggaat attggtatct gacaacagaa gcttattttc cttaaatgaa   3480
gttgtggagt ttaggtgtca gcctggcttt gtcatgaaag gaccccgccg tgtgaagtgc   3540
caggccctga acaaatggga gccagagtta ccaagctgct ccagggtgtg tcagccgcct   3600
ccagaaatcc tgcatggtga gcatacccca agccatcagg acaacttttc acctgggcag   3660
gaagtgttct acagctgtga gcctggctat gacctcagag ggctgcgtc tctgcactgc    3720
acaccccagg gagactggag ccctgaagcc ccgagatgtg cagtgaaatc ctgtgatgac   3780
ttcttgggtc aactccctca tggccgtgtg ctatttccac ttaatctcca gcttggggca   3840
aaggtgtcct ttgtctgtga tgaagggttt cgcttaaagg gcagttccgt tagtcattgt   3900
gtcttggttg gaatgagaag cctttggaat aacagtgttc ctgtgtgtga acatatcttt   3960
tgtccaaatc ctccagctat ccttaatggg agacacacag gaactccctc tggagatatt   4020
ccctatggaa aagaaatatc ttacacatgt gacccccacc cagacagagg gatgaccttc   4080
aacctcattg gggagagcac catccgctgc acaagtgacc ctcatgggaa tggggtttgg   4140
agcagccctg cccctcgctg tgaactttct gttcgtgctg gtcactgtaa aaccccagag   4200
cagtttccat ttgccagtcc tacgatccca attaatgact ttgagtttcc agtcgggaca   4260
tctttgaatt atgaatgccg tcctgggtat tttgggaaaa tgttctctat ctcctgccta   4320
gaaaacttgg tctggtcaag tgttgaagac aactgtagac gaaaatcatg tggacctcca   4380
ccagaaccct tcaatggaat ggtgcatata aacacagata cacagtttgg atcaacagtt   4440
aattattctt gtaatgaagg gtttcgactc attggttccc catctactac ttgtctcgtc   4500
tcaggcaata atgtcacatg ggataagaag gcacctattt gtgagatcat atcttgtgag   4560
ccacctccaa ccatatccaa tggagacttc tacagcaaca atagaacatc ttttcacaat   4620
ggaacggtgg taacttacca gtgccacact ggaccagatg gagaacagct gtttgagctt   4680
gtgggagaac ggtcaatata ttgcaccagc aaagatgatc aagttggtgt ttggagcagc   4740
cctcccccte ggtgtatttc tactaataaa tgcacagctc cagaagttga aaatgcaatt   4800
agagtaccag gaaacaggag tttctttacc ctcactgaga tcatcagatt tagatgtcag   4860
cccgggtttg tcatggtagg gtcccacact gtgcagtgcc agaccaatgg cagatggggg   4920
cccaagctgc cacactgctc cagggtgtgt cagccgcctc cagaaatcct gcatggtgag   4980
cataccctaa gccatcagga caacttttca cctgggcagg aagtgttcta cagctgtgag   5040
cccagctatg acctcagagg ggctgcgtct ctgcactgca cgccccaggg agactggagc   5100
cctgaagccc ctagatgtac agtgaaatcc tgtgatgact tcctgggcca actccctcat   5160
ggccgtgtgc tacttccact taatctccag cttggggcaa aggtgtcctt tgtttgcgat   5220
gaagggttcc gattaaaagg caggtctgct agtcattgtg tcttggctgg aatgaaagcc   5280
ctttggaata gcagtgttcc agtgtgtgaa caaatctttt gtccaaatcc tccagctatc   5340
cttaatggga gacacacagg aactcccttt ggagatattc cctatggaaa agaaatatct   5400
tacgcatgcg acacccaccc agacagaggg atgaccttca acctcattgg ggagagctcc   5460
atccgctgca caagtgaccc tcaagggaat ggggtttgga gcagccctgc ccctcgctgt   5520
gaactttctg ttcctgctgc ctgcccacat ccacccaaga tccaaaacgg gcattacatt   5580
ggaggacacg tatctctata tcttcctggg atgacaatca gctacatttg tgaccccggc   5640
tacctgttag tgggaaaggg cttcattttc tgtacagacc agggaatctg gagccaattg   5700
```

```
gatcattatt gcaaagaagt aaattgtagc ttcccactgt ttatgaatgg aatctcgaag   5760

gagttagaaa tgaaaaaagt atatcactat ggagattatg tgactttgaa gtgtgaagat   5820

gggtatactc tggaaggcag tccctggagc cagtgccagg cggatgacag atgggaccct   5880

cctctggcca aatgtacctc tcgtacacat gatgctctca tagttggcac tttatctggt   5940

acgatcttct ttattttact catcattttc ctctcttgga taattctaaa gcacagaaaa   6000

ggcaataatg cacatgaaaa ccctaaagaa gtggctatcc atttacattc tcaaggaggc   6060

agcagcgttc atccccgaac tctgcaaaca aatgaagaaa atagcagggt ccttccttga   6120
```

```
<210> SEQ ID NO 26
<211> LENGTH: 392
<212> TYPE: PRT
<213> ORGANISM: Artificial Sequence
<220> FEATURE:
<223> OTHER INFORMATION: example Membrane Cofactor Protein (MCP)
      sequence

<400> SEQUENCE: 26

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285
```

```
Pro Ser Ser Thr Lys Pro Pro Ala Leu Ser His Ser Val Ser Thr Ser
    290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
            340                 345                 350

Ala Ile Val Val Gly Val Ala Val Ile Cys Val Val Pro Tyr Arg Tyr
        355                 360                 365

Leu Gln Arg Arg Lys Lys Lys Gly Thr Tyr Leu Thr Asp Glu Thr His
    370                 375                 380

Arg Glu Val Lys Phe Thr Ser Leu
385                 390
```

<210> SEQ ID NO 27
<211> LENGTH: 1179
<212> TYPE: DNA
<213> ORGANISM: Artificial Sequence
<220> FEATURE:
<223> OTHER INFORMATION: nucleotide sequence encoding MCP

<400> SEQUENCE: 27

```
atggagcctc ccggccgccg cgagtgtccc tttccttcct ggcgctttcc tgggttgctt     60

ctggcggcca tggtgttgct gctgtactcc ttctccgatg cctgtgagga gccaccaaca    120

tttgaagcta tggagctcat tggtaaacca aaaccctact atgagattgg tgaacgagta    180

gattataagt gtaaaaaagg atacttctat atacctcctc ttgccaccca tactatttgt    240

gatcggaatc atacatggct acctgtctca gatgacgcct gttatagaga aacatgtcca    300

tatatacggg atcctttaaa tggccaagca gtccctgcaa atgggactta cgagtttggt    360

tatcagatgc actttatttg taatgagggt tattacttaa ttggtgaaga aattctatat    420

tgtgaactta aaggatcagt agcaatttgg agcggtaagc cccaatatg tgaaaaggtt     480

ttgtgtacac cacctccaaa aataaaaaat ggaaaacaca cctttagtga agtagaagta    540

tttgagtatc ttgatgcagt aacttatagt tgtgatcctg cacctggacc agatccattt    600

tcacttattg gagagagcac gatttattgt ggtgacaatt cagtgtggag tcgtgctgct    660

ccagagtgta aagtggtcaa atgtcgattt ccagtagtcg aaaatggaaa acagatatca    720

ggatttggaa aaaaatttta ctacaaagca acagttatgt ttgaatgcga taagggtttt    780

tacctcgatg gcagcgacac aattgtctgt gacagtaaca gtacttggga tcccccagtt    840

ccaaagtgtc ttaaagtgct gcctccatct agtacaaaac ctccagcttt gagtcattca    900

gtgtcgactt cttccactac aaaatctcca gcgtccagtg cctcaggtcc taggcctact    960

tacaagcctc cagtctcaaa ttatccagga tatcctaaac ctgaggaagg aatacttgac   1020

agtttggatg tttgggtcat tgctgtgatt gttattgcca tagttgttgg agttgcagta   1080

atttgtgttg tcccgtacag atatcttcaa aggaggaaga agaaaggcac atacctaact   1140

gatgagaccc acagagaagt aaaatttact tctctctga                          1179
```